（12) United States Patent
Ellington et al.

(10) Patent No.: US 11,807,901 B2
(45) Date of Patent: Nov. 7, 2023

US011807901B2

(54) METHODS AND KITS FOR USING RECOMBINANT MICROORGANISMS AS DIRECT REAGENTS IN BIOLOGICAL APPLICATIONS

(71) Applicant: BOARD OF REGENTS, THE UNIVERSITY OF TEXAS SYSTEM, Austin, TX (US)

(72) Inventors: Andrew Ellington, Austin, TX (US); Sanchita Bhadra, Austin, TX (US); Jared Ellefson, Tucson, AZ (US); Jimmy Gollihar, Boston, MA (US); Arti Pothukuchy, Austin, TX (US); Michelle Byrom, Austin, TX (US); Raghav Shroff, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 100 days.

(21) Appl. No.: 16/764,642

(22) PCT Filed: Nov. 15, 2018

(86) PCT No.: PCT/US2018/061247
§ 371 (c)(1),
(2) Date: May 15, 2020

(87) PCT Pub. No.: WO2019/099644
PCT Pub. Date: May 23, 2019

(65) Prior Publication Data
US 2020/0399679 A1    Dec. 24, 2020

Related U.S. Application Data

(60) Provisional application No. 62/586,606, filed on Nov. 15, 2017.

(51) Int. Cl.
*C12Q 1/686*    (2018.01)

(52) U.S. Cl.
CPC .................................. *C12Q 1/686* (2013.01)

(58) Field of Classification Search
None
See application file for complete search history.

(56) References Cited

U.S. PATENT DOCUMENTS

| 2002/0081565 | A1* | 6/2002 | Barnea | ..................... | C12N 1/04 |
| | | | | | 435/252.1 |
| 2004/0023207 | A1* | 2/2004 | Polansky | ............. | A61K 48/005 |
| | | | | | 435/5 |
| 2013/0059290 | A1 | 3/2013 | Armes et al. | | |
| 2014/0011235 | A1* | 1/2014 | Wang | ..................... | C12P 21/00 |
| | | | | | 435/252.33 |
| 2016/0076083 | A1 | 3/2016 | Ellington et al. | | |
| 2016/0312312 | A1 | 10/2016 | Pardee et al. | | |
| 2017/0292138 | A1* | 10/2017 | Blake | ............. | C12Y 207/04001 |
| 2020/0255891 | A1* | 8/2020 | Ellington | ............... | C12Q 1/686 |

OTHER PUBLICATIONS

Miyamoto-Shinohara, Y. et al., Survival curves for microbial species stored by freeze-drying, Cryobiology, vol. 52, pp. 27-32 (Year: 2006).*
Weiner, M.P. et al., Kits and their unique role in molecular biology: a brief retrospective, Biotechniques, vol. 44, pp. 701-704 (Year: 2008).*
Lion, M.B. et al., The Effect of Oxygen on Freeze-dried *Escherichia coli*, J. Gen. Microbiol., vol. 34, pp. 191-200 (Year: 1961).*
International Search Report and Written Opinion in PCT/US2018/061247. dated Feb. 15, 2019. 9 pages.
Smith, et al. "Lyophilized *Escherichia Coli*-Based Cell-Free Systems for Robust, High-Density, Long-Term Storage," Bio Techniques, Apr. 30, 2014 (Apr. 30, 2014), vol. 56, pp. 186-193. entire document.
Bhadra et al. "Cellular Reagents for Diagnostics and Synthetic Biology," PLoS One, Aug. 15, 2018 (Aug. 15,2018), vol. 13, No. 8, e0201681, pp. 1-24. entire document.
Rohrman et al. "A Paper and Plastic Device for Performing Recombinase Polymerase Amplification of HIV DNA," Lab Chip, Sep. 7, 2012 (Sep. 7, 2012), vol. 12, No. 17, pp. 3082-3088, entire document.

* cited by examiner

*Primary Examiner* — Teresa E Strzelecka
(74) *Attorney, Agent, or Firm* — Meunier Carlin & Curfman LLC

(57) ABSTRACT

Disclosed herein is a method of utilizing an enzyme in a nucleic acid manipulation process, the method comprising: a) transforming a microorganism with a non-native enzyme; b) inducing expression of the enzyme in the microorganism, thereby producing the non-native enzyme; c) adding the microorganism of step b) directly to a non-naturally occurring nucleic acid manipulation process, wherein the non-native enzyme is not purified from the microorganism prior to addition to the nucleic acid manipulation process; and carrying out the nucleic acid manipulation process using the enzyme. Importantly, this method can be carried out without the need to purify the enzyme from the cell producing it before it is used in the nucleic acid manipulation method. Also disclosed herein is a kit for carrying out a nucleic acid manipulation process, the kit comprising a) a microorganism expressing a non-native enzyme; b) nucleic acids of interest; and c) reagents for use in the nucleic acid manipulation process.

12 Claims, 36 Drawing Sheets
Specification includes a Sequence Listing.

| Copies | Cq | | |
| --- | --- | --- | --- |
| | Bst LF | Bst 2.0 | Bst (BR) #3 |
| 6000000 | 7.3 | 2.73 | 3.77 |
| 600000 | 8.36 | 3.03 | 4.23 |
| 60000 | 9.45 | 2.97 | 4.73 |
| 6000 | 13.11 | 3.64 | 5.04 |
| 600 | 12.58 | 4.65 | 6.7 |
| 60 | - | 23.76 | 8.26 |
| 6 | - | - | - |
| 0 | - | - | - |

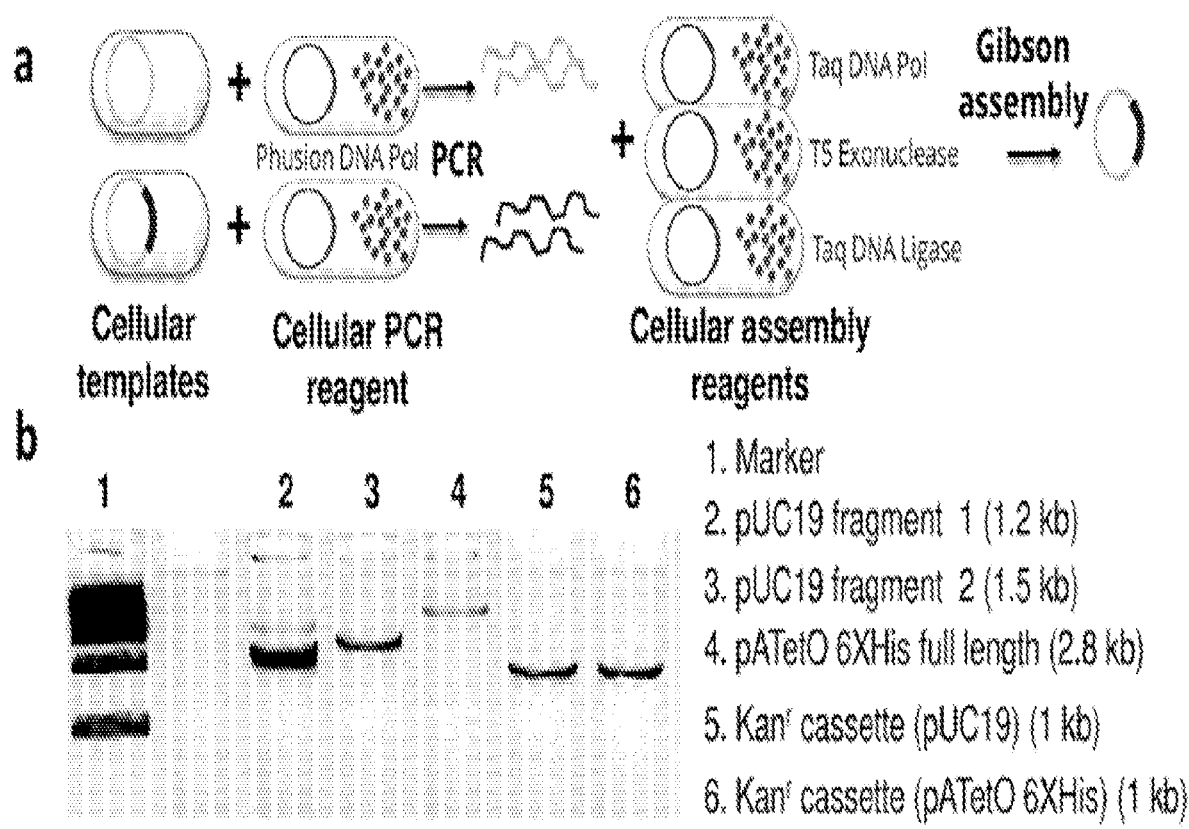
FIGURE 7A-B

C

| Assembly | Cellular (reagent Gibson) | Pure enzyme Gibson | Negative (water) |
|---|---|---|---|
| Gel-purified cellular PCR products | | | |
| pATetO 6XHis + Kan' | 61 | 884 | 4 |
| Puc19 Fragment 1 + pUC19 Fragment 2 + Kan' | 28 | 47 | 0 |
| Unpurified cellular PCR products | | | |
| pATetO 6XHis + Kan' | 8 | 138 | 4 |
| Puc19 Fragment 1 + pUC19 Fragment 2 + Kan' | 2 | 4 | 1 |

SEQUENCE LISTING

<160> NUMBER OF SEQ ID NOS: 33

<210> SEQ ID NO 1
<211> LENGTH: 18
<212> TYPE: DNA
<213> ORGANISM: Artificial Sequence
<220> FEATURE:
<223> OTHER INFORMATION: Synthetic Construct

<400> SEQUENCE: 1
tagtggcgga agggttag                                                    18

<210> SEQ ID NO 2
<211> LENGTH: 18
<212> TYPE: DNA
<213> ORGANISM: Artificial Sequence
<220> FEATURE:
<223> OTHER INFORMATION: Synthetic Construct

<400> SEQUENCE: 2
cgtcatagcc ttggtagg                                                    18

<210> SEQ ID NO 3
<211> LENGTH: 499
<212> TYPE: DNA
<213> ORGANISM: Artificial Sequence
<220> FEATURE:
<223> OTHER INFORMATION: Synthetic Construct

<400> SEQUENCE: 3
cgccaagctt ggtaccgagc tcggatccac tagtaacggc cgccagtgtg ctggaattct        60
aatacgactc actatagggc aattgtttag tggcggaagg gttagtaatg catagataat      120
ttgtccttaa cttgggaata acggttggaa acggccgcta ataccgaatg tggcgatatt      180
tgggcatccg agtaacgtta aagaagggga tcttaggacc tttcggttaa gggagagtct      240
atgtgatatc agctagttgg tggggtaaag gcctaccaag gctatgacgt ctaggcggat      300
tgagagattg ccgccaaca ctgggactga gacactgccc agactcctac gggaggctgc       360
agtcgagaat ctttcgcaat ggacggaagt ctgacgaagc gacgccgcgt gtgtgatgaa      420
ggctctaggg ttgtaaagga attctgcaga tatccatcac actggcggcc gctcgagcat      480
gcatctagag ggcccaatt                                                   499

<210> SEQ ID NO 4
<211> LENGTH: 25
<212> TYPE: DNA
<213> ORGANISM: Artificial Sequence
<220> FEATURE:
<223> OTHER INFORMATION: Synthetic Construct

<400> SEQUENCE: 4
ggtagatcca ttgtggtccc ttgcc                                            25

<210> SEQ ID NO 5
<211> LENGTH: 28
<212> TYPE: DNA
<213> ORGANISM: Artificial Sequence
<220> FEATURE:
<223> OTHER INFORMATION: Synthetic Construct

<400> SEQUENCE: 5
ccacaccatg agcatgtcct cagtagtc                                         28

<210> SEQ ID NO 6
<211> LENGTH: 370
<212> TYPE: DNA
<213> ORGANISM: Artificial Sequence
<220> FEATURE:
<223> OTHER INFORMATION: Synthetic Construct

<400> SEQUENCE: 6

```
ctagtaacgg ccgccagtgt gctggaattc ggtagatcca ttgtggtccc ttgccgccac    60
caagatgaat tgattggccg agcccgtgta tcaccagggg caggatggag cattcggag    120 actgcctgtc tagcaaaatc atatgcacag atgtggcagc ttctttactt ccacagaaga   180
gaccttcgac tgatggccaa tgctatttgt tcggctgtgc cagttgactg ggtaccaacc   240
gggagaacca cctggtcaat ccacggaaag ggagaatgga tgactactga ggacatgctc   300
atggtgtgga atagagtgtg gattgaggag gaattctgca gatatccatc acactggcgg   360
ccgctcgagc                                                          370
```

<210> SEQ ID NO 7
<211> LENGTH: 18
<212> TYPE: DNA
<213> ORGANISM: Artificial Sequence
<220> FEATURE:
<223> OTHER INFORMATION: Synthetic Construct

<400> SEQUENCE: 7

```
gccacccaga agactgtg                                                  18
```

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8

```
tggcaggttt ttctagacgg                                                20
```

<210> SEQ ID NO 9
<211> LENGTH: 39
<212> TYPE: DNA
<213> ORGANISM: Artificial Sequence
<220> FEATURE:
<223> OTHER INFORMATION: Synthetic Construct

<400> SEQUENCE: 9

```
cgccagtaga ggcagggatg agggaaactg tggcgtgat                           39
```

<210> SEQ ID NO 10
<211> LENGTH: 40
<212> TYPE: DNA
<213> ORGANISM: Artificial Sequence
<220> FEATURE:
<223> OTHER INFORMATION: Synthetic Construct

<400> SEQUENCE: 10

```
ggtcatccct gagctgaacg gtcaggtcca ccactgacac                          40
```

<210> SEQ ID NO 11
<211> LENGTH: 22
<212> TYPE: DNA
<213> ORGANISM: Artificial Sequence
<220> FEATURE:
<223> OTHER INFORMATION: Synthetic Construct

<400> SEQUENCE: 11
tgttctggag agccccgcgg cc                                          22

<210> SEQ ID NO 12
<211> LENGTH: 36
<212> TYPE: DNA
<213> ORGANISM: Artificial Sequence
<220> FEATURE:
<223> OTHER INFORMATION: Synthetic Construct

<400> SEQUENCE: 12
ctcactggca tggccttccg tgtccccact gccaac                            36

<210> SEQ ID NO 13
<211> LENGTH: 25
<212> TYPE: DNA
<213> ORGANISM: Artificial Sequence
<220> FEATURE:
<223> OTHER INFORMATION: Synthetic Construct

<400> SEQUENCE: 13
ggacacggaa ggccatgcca gtgag                                       25

<210> SEQ ID NO 14
<211> LENGTH: 482
<212> TYPE: DNA
<213> ORGANISM: Artificial Sequence
<220> FEATURE:
<223> OTHER INFORMATION: Synthetic Construct

<400> SEQUENCE: 14
ctagtaacgg ccgccagtgt gctggaattc ccacagtcca tgccatcact gccacccaga    60
agactgtgga tggcccctcc gggaaactgt ggcgtgatgg ccgcggggct ctccagaaca   120
tcatccctgc ctctactggc gctgccaagg ctgtgggcaa ggtcatccct gagctgaacg   180
ggaagctcac tggcatggcc ttccgtgtcc ccactgccaa cgtgtcagtg gtggacctga   240
cctgccgtct agaaaaacct gccaaatatg atgacatcaa gaaggtggtg aagcaggcgt   300
cggagggccc cctcaagggc atcctgggct acactgagca ccaggtggtc tcctctgact   360
tcaacagcga cacccactcc tccacctttg acgctggggc tggcattgcc ctcaacgacc   420
actttgtcaa gctcatttcc tggaattctg cagatatcca tcacactggc ggccgctcga   480
gc                                                                482

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
ctgtggcatg aacccaatag                                             20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
atcccataga gcaccactcc                                             20

```
<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
ccacgctcca gctgcaaagg                                                      20

<210> SEQ ID NO 18
<211> LENGTH: 105
<212> TYPE: DNA
<213> ORGANISM: Artificial Sequence
<220> FEATURE:
<223> OTHER INFORMATION: Synthetic Construct

<400> SEQUENCE: 18
gggaccatct gtggcatgaa cccaatagcc atacccttttg cagctggagc gtggtacgtg         60
tatgtgaaga ctggaaaaag gagtggtgct ctatgggatg tgcct                         105

<210> SEQ ID NO 19
<211> LENGTH: 40
<212> TYPE: DNA
<213> ORGANISM: Artificial Sequence
<220> FEATURE:
<223> OTHER INFORMATION: Synthetic Construct

<400> SEQUENCE: 19
gcgcccttcg atgtgatggt gatggtgatg cgatcctctg                                40

<210> SEQ ID NO 20
<211> LENGTH: 46
<212> TYPE: DNA
<213> ORGANISM: Artificial Sequence
<220> FEATURE:
<223> OTHER INFORMATION: Synthetic Construct

<400> SEQUENCE: 20
tgataattgc ctctgccaaa attctgtcct caagcgtttt agttcg                         46

<210> SEQ ID NO 21
<211> LENGTH: 65
<212> TYPE: DNA
<213> ORGANISM: Artificial Sequence
<220> FEATURE:
<223> OTHER INFORMATION: Synthetic Construct

<400> SEQUENCE: 21
gatcgcatca ccatcaccat cacatcgaag ggcgcgctga aagccaattc tgattagaaa          60
aactc                                                                      65

<210> SEQ ID NO 22
<211> LENGTH: 57
<212> TYPE: DNA
<213> ORGANISM: Artificial Sequence
<220> FEATURE:
<223> OTHER INFORMATION: Synthetic Construct

<400> SEQUENCE: 22
gaggacagaa ttttggcaga ggcaattatc agatcctttg atctcacgtt gtgtctc             57
```

```
<210> SEQ ID NO 23
<211> LENGTH: 31
<212> TYPE: DNA
<213> ORGANISM: Artificial Sequence
<220> FEATURE:
<223> OTHER INFORMATION: Synthetic Construct

<400> SEQUENCE: 23
gatccccggg taccgagctc gaattcactg g                             31

<210> SEQ ID NO 24
<211> LENGTH: 32
<212> TYPE: DNA
<213> ORGANISM: Artificial Sequence
<220> FEATURE:
<223> OTHER INFORMATION: Synthetic Construct

<400> SEQUENCE: 24
ctctagagtc gacctgcagg catgcaagct tg                            32

<210> SEQ ID NO 25
<211> LENGTH: 32
<212> TYPE: DNA
<213> ORGANISM: Artificial Sequence
<220> FEATURE:
<223> OTHER INFORMATION: Synthetic Construct

<400> SEQUENCE: 25
gacagttacc aatgcttaat cagtgaggca cc                            32

<210> SEQ ID NO 26
<211> LENGTH: 32
<212> TYPE: DNA
<213> ORGANISM: Artificial Sequence
<220> FEATURE:
<223> OTHER INFORMATION: Synthetic Construct

<400> SEQUENCE: 26
ggtgcctcac tgattaagca ttggtaactg tc                            32

<210> SEQ ID NO 27
<211> LENGTH: 62
<212> TYPE: DNA
<213> ORGANISM: Artificial Sequence
<220> FEATURE:
<223> OTHER INFORMATION: Synthetic Construct

<400> SEQUENCE: 27
caagcttgca tgcctgcagg tcgactctag aggctgaaag ccaattctga ttagaaaaac    60
tc                                                                  62

<210> SEQ ID NO 28
<211> LENGTH: 57
<212> TYPE: DNA
<213> ORGANISM: Artificial Sequence
<220> FEATURE:
<223> OTHER INFORMATION: Synthetic Construct

<400> SEQUENCE: 28
ccagtgaatt cgagctcggt acccggggat cgatcctttg atctcacgtt gtgtctc       57

<210> SEQ ID NO 29
<211> LENGTH: 60
<212> TYPE: DNA
<213> ORGANISM: Artificial Sequence
```

```
<220> FEATURE:
<223> OTHER INFORMATION: Synthetic Construct

<400> SEQUENCE: 29
taatacgact cactataggg tggtttctgg ggtgaccggg ttgattctca gcccttcgca    60

<210> SEQ ID NO 30
<211> LENGTH: 60
<212> TYPE: DNA
<213> ORGANISM: Artificial Sequence
<220> FEATURE:
<223> OTHER INFORMATION: Synthetic Construct

<400> SEQUENCE: 30
aggggttggt tggatgaata tagggattg cgaagggctg agaatcaacc cggtcacccc    60

<210> SEQ ID NO 31
<211> LENGTH: 330
<212> TYPE: DNA
<213> ORGANISM: Artificial Sequence
<220> FEATURE:
<223> OTHER INFORMATION: Synthetic Construct

<400> SEQUENCE: 31
ctagtaacgg ccgccagtgt gctggaattc taatacgact cactataggg atgtcgctgt    60
ttggagacac aattgcctac ttgctttcat taacagaaga tggagaaggc aaagcagaac   120
tagcagaaaa gttacactgt tggtttggtg ggaaagaatt tgacctagac tcagccttgg   180
aatggataaa aaacaaaaga tgcttaactg atatacaaaa agcactaatt ggtgcctcta   240
tatgcttttt aaaacccaaa gaccaggaaa gaaaaagaag attcatcaca gaattctgca   300
gatatccatc acactggcgg ccgctcgagc                                    330

<210> SEQ ID NO 32
<211> LENGTH: 30
<212> TYPE: DNA
<213> ORGANISM: Artificial Sequence
<220> FEATURE:
<223> OTHER INFORMATION: Synthetic Construct

<400> SEQUENCE: 32
ctagtaacgg ccgccagtgt gctggaattc                                     30

<210> SEQ ID NO 33
<211> LENGTH: 30
<212> TYPE: DNA
<213> ORGANISM: Artificial Sequence
<220> FEATURE:
<223> OTHER INFORMATION: Synthetic Construct

<400> SEQUENCE: 33
ccgccagtgt gatggatatc tgcagaattc                                     30
```

METHODS AND KITS FOR USING RECOMBINANT MICROORGANISMS AS DIRECT REAGENTS IN BIOLOGICAL APPLICATIONS

CROSS-REFERENCE TO RELATED APPLICATIONS

This application claims priority to and is a United State National Phase Patent Application of International Patent Application Number PCT/US2018/061247 filed on Nov. 15, 2018, which claims priority to U.S. Patent Application No. 62/586,606, filed Nov. 15, 2017, incorporated herein by reference in its entirety.

STATEMENT REGARDING FEDERALLY FUNDED RESEARCH

This invention was made with government support under Grant no. FA9550-14-1-0089 awarded by the Air Force Office of Scientific Research and Grant no. HR0011-12-2-0001 awarded by the Defense Advanced Research Projects Agency (DARPA). The government has certain rights in the invention.

BACKGROUND

Most molecular biology techniques commonly used in research, biotechnology, healthcare, and education rely heavily on purified functional protein reagents (Rittie 2008; Treacy 2011). For instance, nucleic acid amplification (Garibyan 2013; Zhao 2015) and editing (Casini 2015), cornerstones of molecular diagnostics and synthetic biology (Buchan 2014; Smanski 2016), typically depend on the activities of purified DNA and RNA polymerases, nucleases, and ligases. However, purification of these protein reagents requires substantial investment of time, expertise, equipment and infrastructure (Ersson 2011; Scopes 1994), which at this point is primarily performed at the industrial scale. For instance, large batches (hundreds of milliliters to liters) of protein-expressing bacterial cultures need to be cultivated and subsequently processed using a complex set of procedures to lyse the bacteria and separate the proteins of interest from unwanted bacterial and extraction buffer contents (Ward 2012; Burden 1995). To facilitate these pipelines for production, proteins often must be modified with tags for chromatographic separation that are then removed following processing, adding additional steps and complexity to the purification procedure (Arnau 2006; Goh 2017; Guan 2014). Furthermore, most desired proteins need to be maintained in a constant cold chain (4° C. to −80° C.), which not only raises the infrastructure cost for purification and storage, but also creates requirements for shipping and storage at points of use.

As a result, the affordability and accessibility of protein reagents can be significantly limited, especially in resource poor or remote settings (Zhang 2016; Lianidou 2014) What is needed in the art is a simplification of the production, transportation, and storage of these enzymes and proteins that reduce the cost, time, expertise, and infrastructure needed for application and thereby increase accessibility.

SUMMARY

The present invention relates to a method of utilizing an enzyme in a nucleic acid manipulation process, the method comprising: a) transforming a microorganism with a non-native enzyme; b) inducing expression of the enzyme in the microorganism, thereby producing the non-native enzyme; c) adding the microorganism of step b) directly to a non-naturally occurring nucleic acid manipulation process, wherein the non-native enzyme is not purified from the microorganism prior to addition to the nucleic acid manipulation process; and carrying out the nucleic acid manipulation process using the enzyme. Importantly, this method can be carried out without the need to purify the enzyme from the cell producing it before it is used in the nucleic acid manipulation method.

Also disclosed herein is a kit for carrying out a nucleic acid manipulation process, the kit comprising a) a microorganism expressing a non-native enzyme; b) nucleic acids of interest; and c) reagents for use in the nucleic acid manipulation process.

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are exemplary and explanatory only and are not restrictive of the disclosure.

BRIEF DESCRIPTION OF THE FIGURES

The accompanying drawings, which are incorporated in and constitute a part of this specification, illustrate certain examples of the present disclosure and together with the description, serve to explain, without limitation, the principles of the disclosure. Like numbers represent the same elements throughout the figures.

FIG. 7A-B shows PCR and Gibson assembly using cellular reagents. (a) Schematic depicting cellular PCR followed by cellular Gibson assembly for constructing new plasmids. Bacteria harboring target plasmids are mixed with polymerase-expressing cellular reagents and PCR is initiated by adding appropriate primers, buffer, and dNTP. The resulting PCR products are incubated with cellular reagents expressing Gibson assembly enzymes—Taq DNA polymerase, Taq DNA ligase, and T5 exonuclease—to assemble the new construct. (b) Cellular PCR amplification of vector and insert fragments directly from *E. coli* bacteria bearing target DNA plasmids using $2\times10^7$ cells of Phusion cellular reagents. Assembly parts include: (i) "pATetO 6×His full length" vector for two part assembly with Kan$^r$ cassette bearing appropriate overlapping ends, and (ii) "pUC19 Fragments 1 and 2" for three part assembly with Kan$^r$ cassette whose ends overlap with pUC19 vector fragments. (c) Gibson assembly of agarose gel purified and unpurified cellular PCR products using pure or cellular Gibson assembly reagents. In "negative control" samples the PCR products were incubated in Gibson reaction buffer without pure or cellular Gibson enzymes. "pATetO 6×His+Kan$^r$" represents a two part Gibson assembly while "Puc19 Fragment 1+pUC19 Fragment 2+Kan$^r$" represents a three-part Gibson assembly. Representative number of clones recovered in each case in the presence of both ampicillin and kanamycin are reported.

DETAILED DESCRIPTION

Figure 1A:
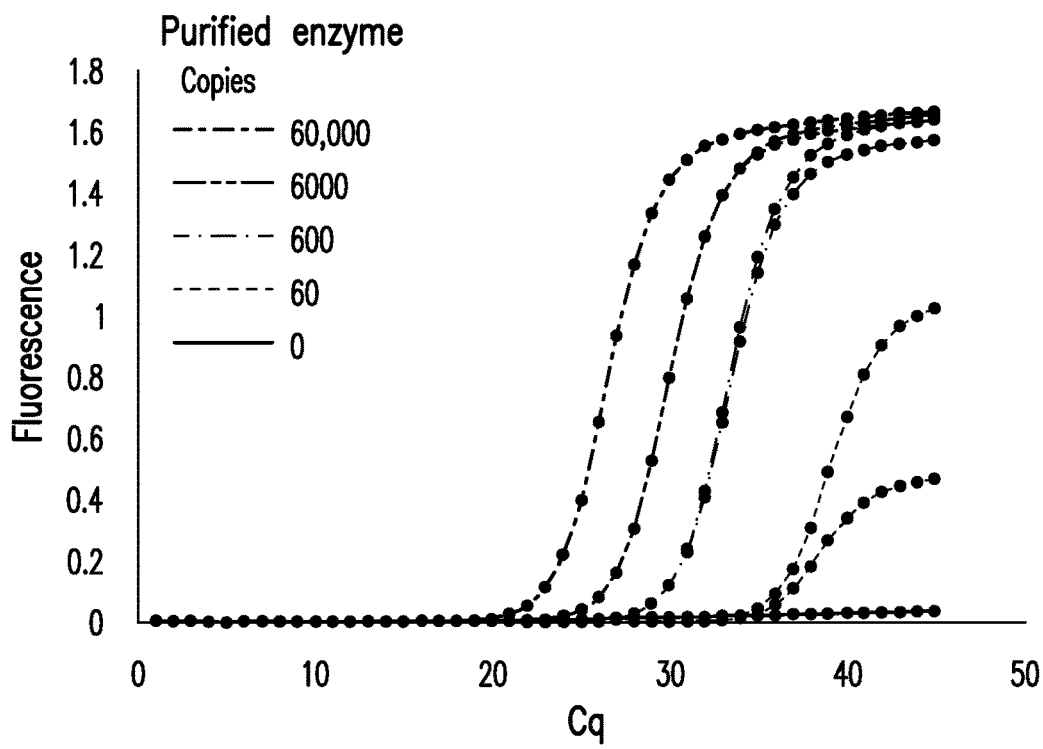
FIG. 1A-D shows TaqMan qPCR analysis using lyophilized Taq DNA polymerase cellular reagents. Indicated copies of synthetic DNA templates derived from Zika virus genomic sequence were amplified using 2.5 units of pure commercial Taq DNA polymerase (panels a and b) or $2 \times 10^7$ cells of rehydrated cellular reagents expressing Taq DNA polymerase (panels c and d). Amplification was assessed in real-time by measuring increase in TaqMan probe fluorescence over time. Representative amplification curves generated using the "Abs quant" analysis in the LightCycler 96 software are depicted in panels a and c. These curves depict the real-time kinetics of PCR amplification mediated by pure versus cellular reagents. The corresponding standard curve analyses performed using the "Abs quant" protocol in the LightCycler 96 software are depicted in panels b and d, respectively. Standard curve analyses data for comparing amplification efficiency, linearity, and error are tabulated as insets.
Figure 1B:
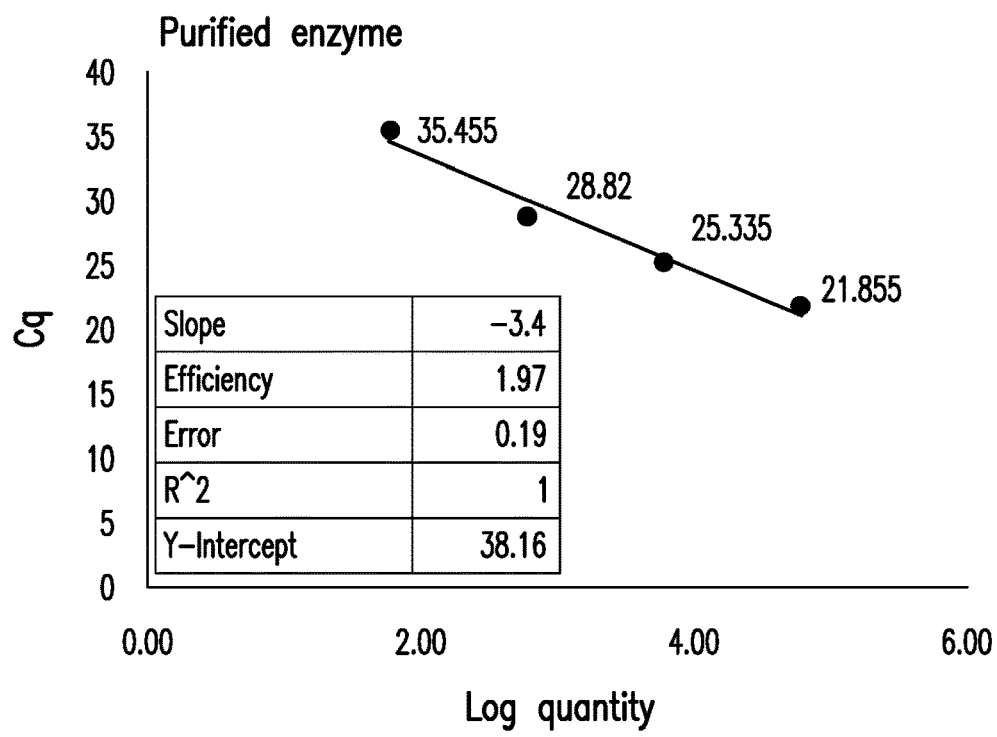
Figure 1C:
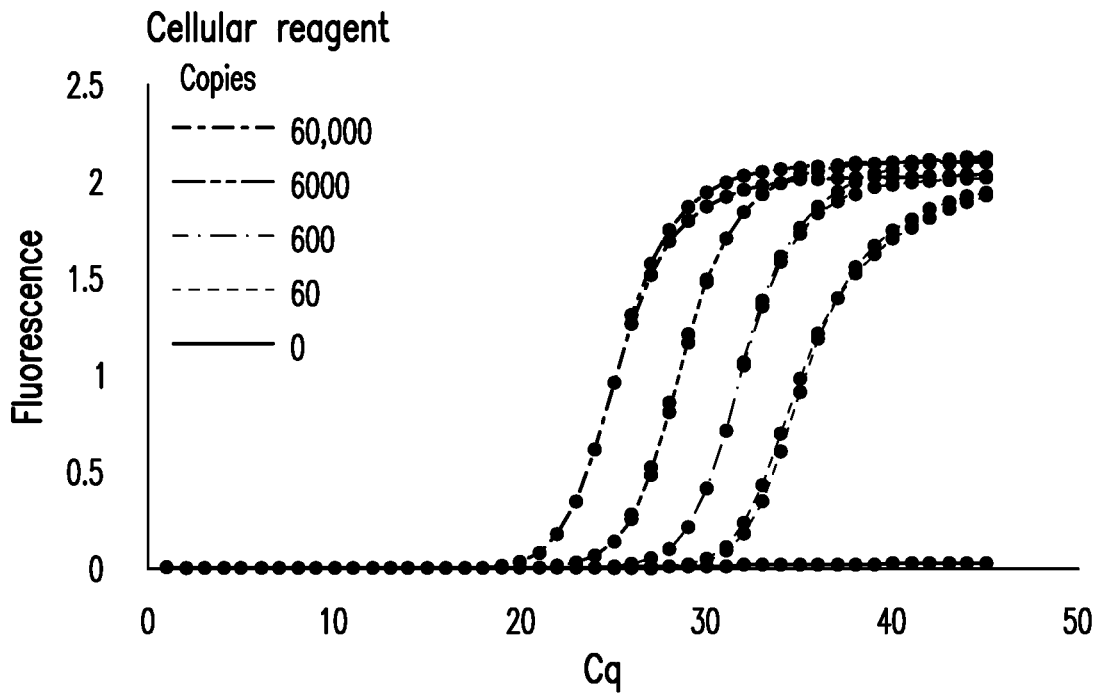
Figure 1D:
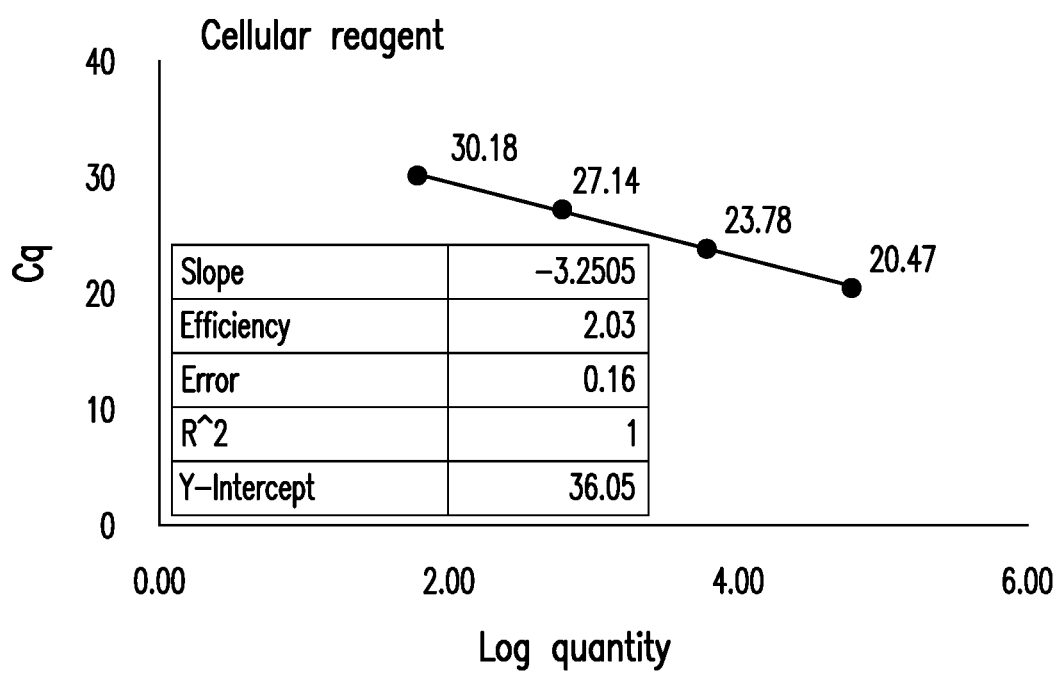

The following description of the disclosure is provided as an enabling teaching of the disclosure in its best, currently known embodiment. To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Definitions

In this specification and in the claims which follow, reference will be made to a number of terms which shall be defined to have the following meanings:

As used herein, the singular forms "a," "an" and "the" include plural referents unless the context clearly dictates otherwise. Thus, for example, reference to a "metal" includes examples having two or more such "metals" unless the context clearly indicates otherwise.

Ranges can be expressed herein as from "about" one particular value, and/or to "about" another particular value. When such a range is expressed, another example includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the terms "cloning vector" and "cloning vector plasmid" are used interchangeably to refer to a circular DNA molecule minimally containing an Origin of Replication, a means for positive selection of host cells harboring the plasmid such as an antibiotic-resistance gene; and a multiple cloning site.

As used herein, the term "Origin of Replication" (ORI) refers to nucleotide sequences that direct replication or duplication of a plasmid within a host cell As used herein, the term "multiple cloning site" refers to nucleotide sequences comprising restriction sites for the purpose of cloning DNA fragments into a cloning vector plasmid.

As used herein, the term "cloning" refers to the process of ligating a DNA molecule into a plasmid and transferring it an appropriate host cell for duplication during propagation of the host.

As used herein, the term "DNA construct" refers to a DNA molecule synthesized by consecutive cloning steps within a cloning vector plasmid, and is commonly used to direct gene expression in any appropriate cell host such as cultured cells in vitro.

As used herein, the terms "restriction endonuclease" or "restriction enzyme" refers to a member or members of a classification of catalytic molecules that bind a cognate sequence of DNA and cleave the DNA molecule at a precise location within that sequence.

As used herein, the term "DNA fragment" refers to any isolated molecule of DNA, including but not limited to a protein-coding sequence, reporter gene, promoter, enhancer, intron, exon, poly-A tail, multiple cloning site, nuclear localization signal, or mRNA stabilization signal, or any other naturally occurring or synthetic DNA molecule. Alternatively, a DNA fragment may be completely of synthetic origin, produced in vitro. Furthermore, a DNA fragment may comprise any combination of isolated naturally occurring and/or synthetic fragments.

As used herein, the terms "gene promoter" or "promoter" (P) refer to a nucleotide sequence required for expression of a gene.

As used herein, the term "enhancer region" refers to a nucleotide sequence that is not required for expression of a target gene, but will increase the level of gene expression under appropriate conditions.

As used herein, the term "reporter gene" refers to a nucleotide sequences encoding a protein useful for monitoring the activity of a particular promoter of interest.

As used herein, the term "poly-A tail" refers to a sequence of adenine (A) nucleotides commonly found at the end of messenger RNA (mRNA) molecules. A Poly-A tail signal is incorporated into the 3' ends of DNA constructs or transgenes to facilitate expression of the gene of interest.

As used herein, the term "intron" refers to the nucleotide sequences of a non-protein-coding region of a gene found between two protein-coding regions or exons.

As used herein, the term "untranslated region" (UTR) refers to nucleotide sequences encompassing the non-protein-coding region of an mRNA molecule. These untranslated regions can reside at the 5' end (5' UTR) or the 3' end (3' UTR) an mRNA molecule.

As used herein, the term "tag sequence" (TAG) refers to nucleotide sequences encoding a unique protein region that allows it to be detected, or in some cases, distinguished from any endogenous counterpart.

As used herein, the term "primer site" refers to nucleotide sequences that serve as DNA templates onto which single-stranded DNA oligonucleotides can anneal for the purpose of initiating DNA sequencing, PCR amplification, and/or RNA transcription.

The term "gene" as used in this specification refers to a segment of deoxyribonucleotides (DNA) possessing the information required for synthesis of a functional biological product such as a protein or ribonucleic acid (RNA).

The term "genetic engineering" is used to indicate various methods involved in gene manipulation including isolation, joining, introducing of gene(s) as well as methods to isolate select organisms containing the manipulated gene(s).

As specified herein, the term "DNA construct" refers to a sequence of deoxyribonucleotides including deoxyribonucleotides obtained from one or more sources.

The term "gene expression" refers to efficient transcription and translation of genetic information contained in concerned genes.

The term "recombinant" cells or population of cells refers to cells or population of cells into which an exogenous nucleic acid sequence is introduced using a delivery vehicle such as a plasmid.

The term "microorganism" mentioned herein refers to one or more forms/species of bacteria or yeast.

The term "nucleic acid" as used herein means natural and synthetic DNA, RNA, oligonucleotides, oligonucleosides, and derivatives thereof. For ease of discussion, such nucleic acids are at times collectively referred to herein as "constructs," "plasmids," or "vectors."

The term "shelf-stable" as used herein refers to the bioactivity (e.g., gene expression level, enzyme activity, or biosynthetic activity upon re-hydration) of the compositions described herein changing no more than 30% upon storage at room temperature (i.e., about 20° C. to 24° C.) and relative humidity of no more than 10% for two weeks. Stated another way, if the bioactivity of the shelf-stable composition re-hydrated on the day it's lyophilized (referred to as the first-day bioactivity herein) is set as 100%, then after two-week storage, the bioactivity of the composition is no less than 70%. A shelf-stable composition can also mean a composition that can regain at least 3% of the first-day bioactivity after storage for about 3 months, preferably at least 5%, at least 10%>, at least 12%, at least 15%, at least 18%, at least 20%, at least 25%, at least 30%, at least 35%, at least 40%, at least 45%, at least 50%, at least 55%, at least 60%, at least 65%, at least 70%, at least 75%, at least 80%, at least 85% o, at least 90%>, at least 95% or more of the first-day bioactivity. At a maximum, the shelf-stable composition is stored in an environment with relative humidity of 60%. Preferably, the shelf-stable composition is stored in an environment with relative humidity of less than 50%>, less than 40%>, less than 30%>, less than 20%>, less than 10%, less than 5%, less than 1%, or less than 0.1%. In one embodiment, the shelf-stable composition is stored in a humidity-controlled environment (e.g., a desiccator or a containing comprising a desiccant). Preferably, the shelf-stable composition is stored in an environment comprising nitrogen gas greater than 79% by volume, greater than 85% by volume, greater than 90% by volume, or greater than 95% by volume.

As used herein, the term "substantially free of water" means that the water content in a composition is no more than 5% by weight. The term encompasses, for example, a water content of no more than 4%, no more than 3%, no more than 2%, no more than 1%, no more than 0.5%, or no more than 0.1% by weight.

The term "nucleic acid manipulation" is used herein to refer to any reaction that results in the synthesis of one or more biological compounds (e.g., DNA, RNA, proteins, monosaccharides, polysaccharides, etc.). For example, a transcription reaction is a biosynthetic reaction because RNA is produced. Other examples of biosynthetic reactions include, but are not limited to, translation reactions, coupled transcription and translation reactions, DNA synthesis, and polymerase chain reactions.

As used herein, the terms "nucleic acid," "polynucleotide," and "oligonucleotide" are used interchangeably to generally refer to any polyribonucleotide or poly-deoxyribonucleotide, and includes unmodified RNA, unmodified DNA, modified RNA, and modified DNA. Polynucleotides include, without limitation, single- and double-stranded DNA and RNA polynucleotides. The term "nucleic acid" embraces chemically, enzymatically or metabolically modified forms of polynucleotides, as well as the naturally occurring chemical forms of DNA and RNA found in or characteristic of viruses and cells, including for example, simple (prokaryotic) and complex (eukaryotic) cells. A nucleic acid polynucleotide or oligonucleotide as described herein retains the ability to hybridize to its cognate complimentary strand. An oligonucleotide is not necessarily physically derived from any existing or natural sequence, but can be generated in any manner, including chemical synthesis, DNA replication, DNA amplification, in vitro transcription, reverse transcription or any combination thereof.

The term "template-directed synthetic reaction" is used herein to refer to a synthetic reaction for which a nucleic acid template guides the pattern of nucleic acid or amino acid addition to a nucleic acid or polypeptide polymer. DNA replication and transcription are template-directed synthetic reactions that produce DNA or RNA products, respectively using a DNA template. Reverse transcription produces a DNA product using an RNA template. Translation is a template-directed synthetic reaction that produces a polypeptide or protein using an RNA template.

The terms "active" or "activated" are used interchangeably herein to refer to the readiness of a shelf-stable composition described herein or a portion thereof to perform an innate function or task. Reaction components lyophilized on a solid support are "activated" by addition of water or an aqueous sample, regaining transcription and/or translation activities. In some embodiments, the composition or a portion thereof performs the function or task when it's active or activated. In other embodiments, the composition or a portion thereof does not perform the function or task when it's active or activated, but is ready to do so when an external factor (an analyte or trigger as non-limiting examples) is provided. At a minimum, a lyophilized reaction/component mixture that regains at least 3% of its original activity upon re-hydration is considered "active." Preferably the mixture regains at least 10%, at least 12%, at least 15%, at least 18%, at least 20%, at least 25%, at least 30%, at least 35%, at least 40%, at least 45%, at least 50%, at least 55%, at least 60%, at least 65%, at least 70%, at least 75%, at least 80%>, at least 85%, at least 90%>, at least 95% or more of its original activity (i.e., activity just prior to lyophilization). The regained activity is comparable to the original activity when the difference between the two is no more than 20%.

As used herein, the term "sample," means any sample comprising or being tested for the presence of one or more analytes. Such samples include, without limitation, those derived from or containing cells, organisms (bacteria, viruses), lysed cells or organisms, cellular extracts, nuclear extracts, components of cells or organisms, extracellular fluid, media in which cells or organisms are cultured in vitro, blood, plasma, serum, gastrointestinal secretions, ascites, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, pleural fluid, nipple aspirates, breast milk, external secretions of the skin, respiratory, intestinal, and genitourinary tracts, and prostatic fluid. A sample can be a viral or bacterial sample, a sample obtained from an environmental source, such as a body of polluted water, an air sample, or a soil sample, as well as a food industry sample. A sample can be a biological sample which refers to the fact that it is derived or obtained from a living organism. The organism can be in vivo (e.g. a whole organism) or can be in vitro (e.g., cells or organs grown in culture). A sample can be a biological product. In one embodiment, a "biological sample" also refers to a cell or population of cells or a quantity of tissue or fluid from a subject. Often, a "biological sample" will contain cells from a subject, but the term can also refer to non-cellular biological material, such as non-cellular fractions of blood, saliva, or urine, that can be used to measure analyte or enzyme activity levels, for example, upon rehydration. Biological samples also include explants and primary and/or transformed cell cultures derived from patient tissues. A biological sample can be provided by removing a sample of cells from subject, but can also be accomplished by using previously isolated cells or cellular extracts {e.g., isolated by another person, at another time, and/or for another purpose). Archival tissues, such as those having treatment or outcome history can also be used. Biological samples include, but are not limited to, tissue biopsies, scrapes {e.g. buccal scrapes), urine, or cell culture. Biological samples also include tissue biopsies, cell culture. The term "sample" also includes untreated or pretreated (or pre-processed) samples. For example, a sample can be pretreated to increase analyte concentration.

The term "analyte" is used herein to refer to a substance or chemical constituent in a sample (e.g., a biological or industrial fluid) that can be analyzed (e.g., detected and quantified) and monitored using the sensors described herein. Examples of an analyte include, but are not limited to, a small inorganic or organic molecule, an ion, a nucleic acid (e.g., DNA, RNA), a polypeptide, a peptide, a monosaccharide, a polysaccharide, a metabolic product, a hormone, an antigen, an antibody, a biological cell, a virus, and a liposome.

As used herein, the term "small molecule" refers to a natural or synthetic molecule having a molecular mass of less than about 5 kD, organic or inorganic compounds having a molecular mass of less than about 5 kD, less than about 2 kD, or less than about 1 kD.

As used herein, the term "portable" refers to a device or system that can be held by a person of ordinary strength in one or two hands, without the need for any special carriers, or which has applicability in the field or away from a standard lab. A portable device can be configured to be used outside of a laboratory setting. In certain embodiments, a portable device is, e.g., battery powered. Also disclosed is a portable system, meaning the system can be used outside of a traditional laboratory.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular electrode is disclosed and discussed and a number of modifications that can be made to the electrode are discussed, specifically contemplated is each and every combination and permutation of the electrode and the modifications that are possible unless specifically indicated to the contrary. Thus, if a class of electrodes A, B, and C are disclosed as well as a class of electrodes D, E, and F and an example of a combination electrode, or, for example, a combination electrode comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

General Description

Disclosed herein are methods, compositions, and kits for enhancing affordability and application of molecular biology reagents worldwide. This is achieved by employing methodologies and tools that simplify reagent production by eliminating protein purification. Disclosed herein are methods and compositions that make use of lyophilized bacteria as cellular packets of reagents ("cellular reagents", also referred to herein as "superior reagents"). These cellular reagents not only perform extremely well compared to their purified counterparts, but also are stable for long periods at ambient temperatures. In addition, most standard operating procedures for molecular biology are minimally perturbed—the pure protein reagent can be simply replaced by an optimal amount of the corresponding rehydrated, lyophilized cellular reagent.

To prove the general feasibility of this approach, several cellular reagents have been used for multiple molecular biology and diagnostics applications. These include DNA polymerases, such as KlenTaq (Barnes 1994), Taq (Chien 1976), Bst-LF (Phang 1995), Phusion (Wang 2004; Uemori 1993), and RTX, an engineered thermostable reverse transcriptase (Ellefson 2016). The cellular reagents perform on par with purified reagents in analytical procedures such as qPCR, reverse transcription qPCR, endpoint PCR analyzed by agarose gel electrophoresis, and loop-mediated isothermal amplification (LAMP) with fluorogenic strand displacement (OSD) probes (Jiang 2015). Amplification efficiency, detection limits, and time to result were comparable to the same reactions performed with pure enzymes. Cellular reagents were also used to demonstrate the synthesis of plasmids by Gibson assembly (Gibson 2009).

Compared to the current technologies for production and distribution of purified protein reagents, bacterial reagents present the following advantages—(i) significantly lower production time and cost due to elimination of protein purification, (ii) robust production process optimized to use culture density (measured as A600) as a convenient metric for ensuring uniformity of performance (ii) favorable production scale or yield per culture volume (1 ml culture=150 qPCR or isothermal amplification reactions), (iii) cheaper storage and transport without cold chain, (iv) seamless integration of ready-to-use lyophilized bacterial reagents with current molecular and synthetic biology and nucleic acid diagnostic technologies without decline in performance and outcomes. Furthermore, the bacterial reagent production process involves considerably fewer procedures and equipment thus making it easier to adopt for local production.

Specifically, disclosed herein is a method of utilizing an enzyme in a nucleic acid manipulation process, the method comprising: a) transforming a microorganism with a non-native enzyme; b) inducing expression of the enzyme in the microorganism, thereby producing the non-native enzyme; c) adding the microorganism of step b) directly to a non-naturally occurring nucleic acid manipulation process, wherein the non-native enzyme is not purified from the microorganism prior to addition to the nucleic acid manipulation process; and carrying out the nucleic acid manipulation process using the enzyme. Importantly, this method can be carried out without the need to purify the enzyme from the cell producing it before it is used in the nucleic acid manipulation method.

Transformation, in the context of the current invention, is the process by which exogenous nucleic acid is inserted into a bacterium, causing the bacterium to change its genotype and/or phenotype. Such a change in genotype or phenotype may be transient or otherwise. Exogenous nucleic acid (such as that encoding the enzymes disclosed herein) is any nucleic acid, whether naturally occurring or otherwise, from any source that is capable of being inserted into any organism. Preferably, exogenous nucleic acid is any nucleic acid, whether naturally occurring or otherwise, from any source that is capable of being inserted into a microorganism.

The transformed microorganism used to produce the enzyme can be a cell, such as a eukaryotic or prokaryotic cell. The methods disclosed herein are useful in additional cellular environments such as those offered by eukaryotes. For instance, protein production agents including but not limited to yeasts such as *Pichia pastoris* and *Saccharomyces cerevisiae* can be employed to produce enzymes, including those that are post-translationally modified.

The nucleic acid manipulation process can be any process known to those of skill in the art to manipulate nucleic acids. An example of nucleic acid manipulation is nucleic acid amplification. Examples of nucleic acid amplification include thermocycled processes, such as polymerase chain reaction (PCR), as well as isothermal methods, such as ligase chain reaction (LCR), self-sustained sequence replication (SSR), nucleic acid sequence-based amplification (NASBA), loop-mediated isothermal amplification (LAMP), amplification with Qb-replicase, or the like.

In some embodiments, the nucleic acid manipulation is strand displacement amplification reaction (SDA). In some embodiments, the nucleic acid manipulation is multiple displacement amplification (MDA). In one embodiment, the nucleic acid manipulation is the rolling circle amplification (RCA) method. Rolling circle amplification that could be used may be a linear RCA (LRCA) or it may be an exponential RCA (ERCA). In another embodiment, multiply primed rolling circle amplification (MPRCA) is employed for amplifying the nucleic acid. Examples of types of nucleic acid amplification useful with the disclosed methods can be found in Fakruddin et al. (J Pharm Bioallied Sci. 2013 October-December; 5(4): 245-252), hereby included in its totality for its teaching concerning nucleic acid amplification.

Other types of nucleic acid manipulation can also be used with the present methods and kits. Examples include, but are not limited to cloning, such as in vitro cloning, cleavage, ligation, transcription, and splicing.

Accordingly, the enzyme produced by the microorganism can be necessary for the nucleic acid manipulation process to proceed. In other words, the nucleic acid manipulation process can be reliant upon the enzyme produced from the cell. The enzyme can comprise, for example, polymerase, reverse transcriptase, methylase, nuclease, cleavase, phosphatase, kinase, nickase, pyrophosphatase, DNA glycosylase, recombinase, helicase, topoisomerase, methyltransferase, capping enzyme, deadenylase, or ligase. It is noted that this list is exemplary and not exhaustive, and any enzyme that is useful in a nucleic acid manipulation process can be used with the methods and kits disclosed herein.

The entire microorganism can be used in the nucleic acid manipulation process. For example, if the nucleic acid manipulation process is amplification, and the microorganism has been transformed so that it is producing a polymerase, the entire microorganism can be used in place of the polymerase. In other words, one of skill in the art would readily understand what reagents are needed to carry out amplification. Instead of adding a purified polymerase to the reaction mixture, however, the entire, lysed microorganism (which is producing a polymerase) can be added to the mix in order to expose the reagents to the polymerase.

To simplify usage, cellular reagents can be preserved on a solid support for later use. The solid support can be in any form including, but is not limited to, a well, a tube, a planar substrate (e.g., a chip or a plate), a sphere, a porous substrate (e.g., a mesh or a foam), a 3D scaffold, a patterned surface (e.g., nano-patterns, or micro-patterns, or both), a porous or solid bead, a hydrogel, a channel (e.g., a microfluidic channel), a smooth surface, and a rough surface. In a preferred embodiment, the solid support is hydrophilic and preferably porous.

A patterned surface can be physically or chemically patterned, or both. A physically patterned surface is textured, and can comprise nano-patterns, micro-patterns, or both. A chemically patterned surface typically comprises hydrophilic molecules and/or hydrophobic molecules attached to the surface in a desired pattern. For example, a hydrophobic surface can be patterned with hydrophilic molecules to render certain regions hydrophilic. Methods of producing physically or chemically patterned surfaces are known in the art.

The solid support can comprise a matrix capable of high capillary action. High capillary action enables even distribution of a small volume of liquid over a large surface area without the use of a pump. Preferably, the matrix capable of high capillary action is porous and hydrophilic.

The solid support can comprise paper. Papers applicable in the technology described herein can include, but not limited to, printing paper, wrapping paper, writing paper, drawing paper, specialty paper (for example, chromatography paper, filter paper, e.g., Whatman™ filter paper), handmade paper, or blotting paper. The use of paper confers several advantages: low cost, light weight, and thin cross section. Additionally, white paper can act as a surface for displaying optical signals (e.g., fluorescence, luminescence, or visible color).

In one embodiment, the paper is hydrophilic and preferably porous. In one embodiment, the paper is hydrophobic. For example, hydrophobic paper can become hydrophilic after treatment by a laser, therefore one can create hydrophilic regions on hydrophobic paper by selective laser scanning. In one embodiment, the solid support comprises quartz micro fiber, mixed esters of cellulose, cellulose acetate, silk, porous aluminum oxide (e.g., nanopore membrane), or regenerated membrane.

In one embodiment, the shelf-stable cellular reagent is lyophilized in a tube/micro-chamber and then transferred to a high capillary material upon re-hydration.

In one embodiment, the solid support comprises a sticky component, thereby allowing the shelf-stable composition to stay on surfaces.

In one embodiment, the solid support comprises 1, 2, 3, 4, 5, 6, 7, 8, 9, 10, 20, or more spatially distinct reaction regions where different cellular reagents are confined. The area that contains the cellular reagents is herein referred to as "a reaction region." By way of example only, reaction regions can be created by a chemical process such as using hydrophobic barriers on a piece of paper. The hydrophobic barriers are minimally permeable by water. When an aqueous solution comprising the cellular reagents/whole cell is added to a reaction region, due to the presence of the hydrophobic barrier, the solution is confined within the reaction regions. The hydrophobic barrier can comprise hydrophobic materials such as hydrophobic polymer or wax. The hydrophobic barrier can be patterned by any existing patterning method (e.g., micro-contact printing, or dip pen lithography, photolithography, e-beam lithography, laser printing, inject printing, or a micro-arrayer). Methods of creating hydrophobic patterns on paper are known in the art; see for example, WO2009121041 and WO2008/049083, the contents of each of which are incorporated by reference for the hydrophobic patterning methods.

The reaction regions can be arranged in a random or pre-determined pattern (e.g., linear, periodic, or pseudo-periodic). The reaction regions can be patterned on the solid support using a patterning device (e.g., a laser printer, an inject printer or a micro-arrayer). The reaction regions can also be created by a physical process such as producing wells on the solid support.

In one embodiment, the solid support comprises one or more fluidic channels (e.g., microfluidic channels) that connect reaction regions with an area for adding an aqueous sample. In this embodiment, when an aqueous sample is added to the area, the fluid is wicked away to the reaction regions, thereby a plurality of reaction regions can be activated by the same sample.

In one particular embodiment, the cellular reagent can be dehydrated or freeze-drying in individual-use portions (WO2008155524A1 and EP3077551A1, both incorporated by reference in their entirety for their teaching concerning preserving cellular reagents.) This can be done in a variety of manners, including, but not limited to, freeze-drying the cellular reagents directly on glass fiber filter paper. These dry reagent-saturated filter paper pieces can be then directly dropped into their appropriate reaction mixtures, such as a PCR or a LAMP assay, to rehydrate the cellular reagents and recuperate enzyme activity. In one example, large-scale production can use filter paper sheets printed with a grid of individual use excisable pieces. Using automated liquid handlers, appropriate amount of cellular reagents are dispensed and freeze-dried in each individual unit of the grid. These sheets are sealed in foil and can be supplied independently for use in user-customized assays. These paper-based cellular reagents can also be included in diagnostic or educational kits containing primers, probes, and nucleic acid templates for specific targets. They can also be used in point-of-care diagnostics and in rapid assays in the field.

Unlike the bulk powder-form of cellular reagents, paper-based reagents are easier to store and ship due to their flatter profile (compared to tubes of bulk cellular reagents). They also reduce the number of user-required steps to simply excision from larger sheet of reagent paper and addition of the small stub of reagent paper directly into individual reaction master mixes. Presence of the paper pieces during nucleic acid amplification and readout do not adversely affect the outcome The lyophilized reagents can be shelf-stable, and are capable of long-term storage at ambient temperatures. The reagents can be substantially free of water.

Lyophilization, also known as freeze-drying, is a dehydration process that involves freezing a material and then reducing the surrounding pressure to allow water to sublimate. Parameters such as freezing temperature, rate of temperature change, and pressure are variables for different lyophilization process. Accordingly, the lyophilization processes used in the methods and compositions herein are not limited to a specific set of parameters. It should be apparent to a skilled artisan that preferred lyophilization processes would yield a shelf-stable composition with a long shelf life. Instruments for performing lyophilization are commercially available through vendors such as Cole-Parmer and Millrock Technology.

In some embodiments, more than one enzyme can be transformed into the microorganism. In other words, two, three, four, or more different enzymes can be produced by the same cell. Those of skill in the art will understand how to transform the same microorganism with multiple, different enzymes. In other embodiments, different microorganisms can be used in the same method, so that multiple, different microorganisms, transformed to express either the same or different enzymes, are used in the same nucleic acid manipulation method. The enzyme can be non-native to the microorganism into which it is inserted for production. In other words, the enzyme produced by the microorganism in the disclosed methods is not naturally produced by that microorganism. Alternatively, the microorganism may naturally produce the enzyme, but not in sufficient quantities for the nucleic acid manipulation process.

The nucleic acid manipulation process can further comprise components (reagents) needed to carry out the molecular process. Examples include any substance that is needed to carry out an enzymatic reaction. For example, in the case of nucleic acid amplification, if the enzyme provided by the microorganism is a polymerase, the further components can include, but are not limited to, DNA template, primers, and nucleotides. Some, or all, of the further components can be provided naturally by the microorganism, so that they do not need to be added exogenously. In the case of ancillary enzymes that are needed for nucleic acid manipulation, they can be simultaneously produced by transformation of a host microorganism, along with the polymerase or other primary enzyme. The necessary components for nucleic acid manipulation can also be added exogenously to the reaction.

In some embodiments, the cell (microorganism) can be lysed prior to addition to the nucleic acid manipulation process. Examples of cell lysis include, but are not limited to, physical methods, such as heating, lyophilizing, grinding, sonicating, and homogenizing. The microorganism can also be treated to chemical or enzymatic methods for lysing a cell. Such methods are known to those of skill in the art.

Also disclosed herein is a kit for carrying out a nucleic acid manipulation process, the kit comprising a) a microorganism expressing a non-native enzyme; b) nucleic acids of interest; and c) reagents for use in the nucleic acid manipulation process. Specifically, the nucleic acids of interest can be any nucleic useful in a nucleic acid manipulation process. Examples include, but are not limited to, template and primers. The microorganism can be any cellular organism that is capable of being transformed with a non-native enzyme, and induced to express the enzyme. Alternatively, the enzyme can be native to the microorganism, but not expressed in sufficient quantities to be useful in the subsequent nucleic acid manipulation process. The reagents can be any components necessary to carry out the nucleic acid manipulation process. Examples include, but aren't limited to, chemical reagents or other enzymes. One of skill in the art will understand that this includes any material necessary for the nucleic acid manipulation process, other than the enzyme produced by the transformed microorganism.

Further disclosed is a portable system for carrying out nucleic acid manipulation, wherein the portable system comprises a cellular reagent lyophilized on a substrate. The cellular reagent can be on paper, for example, and can be reconstituted for use in a cellular manipulation reaction, such as amplification.

It is understood that the methods and kits of the present disclosure can be used in combination with the various compositions, methods, products, and applications disclosed herein.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. Efforts have been made to ensure accuracy with respect to numbers (e.g., amounts, temperatures, etc.); however, some errors and deviations should be accounted for. Unless indicated otherwise, temperature is ° C. or is at ambient temperature, and pressure is at or near atmospheric. There are numerous variations and combinations of process conditions that can be used to optimize product quality and performance. Only reasonable and routine experimentation are required to optimize such process conditions.

Example 1: Cellular Reagents for Diagnostics and Molecular Biology

1) Introduction

It has been discovered that the overproduction of enzymes in bacteria followed by their lyophilization leads to 'cellular reagents' that can be directly used to carry out numerous molecular biology reactions. Herein, it is the use of cellular reagents in a variety of molecular diagnostics is demonstrated, such as TaqMan qPCR with no diminution in sensitivity, and in synthetic biology cornerstones such as the Gibson assembly of DNA fragments, where new plasmids can be constructed solely based on adding cellular reagents. Cellular reagents have significantly reduced complexity and cost of production, storage and implementation, features that should facilitate accessibility and use in resource-poor conditions.

2) Materials and Methods i. Chemicals and Reagents

All chemicals were of analytical grade and were purchased from Sigma-Aldrich (St. Louis, Mo., U.S.A.) unless otherwise indicated. Bacterial growth media were purchased from Thermo Fisher Scientific (Waltham, Mass.). Bacterial strains and all pure enzymes and related buffers were purchased from New England Biolabs (NEB, Ipswich, Mass.) unless otherwise indicated. KlenTaq1 was purchased from DNA Polymerase Technologies (St. Louis, Mo.). All oligonucleotides and gene blocks were obtained from Integrated DNA Technologies (IDT, Coralville, Iowa, U.S.A.). Oligonucleotide and gene block sequences are summarized in Table 1.

ii. Plasmids and Cloning

PCR amplification of sequences for subsequent cloning was performed using Phusion DNA polymerase. Standard Gibson assembly techniques were used for all cloning unless otherwise noted. Coding sequences for shuffle-optimized KlenTaq DNA polymerase (Milligan 2018), Bst LF DNA polymerase (Milligan 2018), Taq DNA ligase (UniProtKB—B7A6G7), T5 Exonuclease (UniProtKB—P06229), MMLV reverse transcriptase (UniProtKB—P03355), Taq DNA polymerase (Lawyer 1986), Phusion DNA polymerase (Wang 2004; Uemori 1993) and RTX thermostable reverse transcriptase (Ellefson 2016) were cloned into pATetO 6×His plasmid. This is an in-house designed plasmid based on the pASK-IBA37plus vector (IBA GmbH) from which the multiple cloning site, and Rop gene have been removed to improve plasmid copy number (Milligan 2018). The plasmid also features a modified pAtetO promoter with a single point mutation to make it unidirectional. All enzyme coding sequences introduced into this vector were placed immediately downstream of the Factor X cleavage site. For some experiments, the coding sequences for wildtype and exonuclease deficient versions of RTX were cloned downstream of the T7 promoter in the pET21 vector (Sigma- Aldrich) (Ellefson 2016). Assembled plasmids were transformed into chemically competent Top10 *E. coli* and verified by Sanger sequencing at the Institute of Cellular and Molecular Biology Core DNA Sequencing Facility.

iii. Production of Lyophilized Cellular Reagents

Top10, BL21 and BL21 DE3 strains of *E. coli* were used to prepare lyophilized cellular reagents. Chemically competent BL21 and BL21 DE3 bacteria were freshly transformed with pATetO and pET21 constructs, respectively, prior to each instance of cellular reagent preparation. Top10 strains transformed with pATetO constructs and stored as glycerol stocks at −80° C. were used to inoculate fresh cultures for cellular reagent preparation. Overnight 3 ml cultures of transformed bacterial strains were grown in 2×YT broth containing 100 µg/ml ampicillin. Subsequently, 50 ml sub-cultures at 1:200 dilution, unless otherwise specified, were initiated in Superior Broth™ (Athena Environmental Sciences, Inc., Baltimore, Md., USA) containing 100 µg/ml ampicillin. Sub-cultures were incubated in 250 ml conical flasks at 37° C. and constant 225 rpm agitation. Bacterial growth was monitored by measuring absorbance of 600 nm wavelength light.

Protein production was initiated by inducing transcription from the pATetO and the pT7 promoters by adding 200 ng/ml anhydrotetracycline (aTC) or 1 mM isopropyl β-D-1-thiogalactopyranoside (IPTG) to logarithm phase (typical A600=0.4 to 0.7) cultures. The pATetO promoter was induced for 3 h at 37° C., unless otherwise indicated. The pT7 promoter was induced for 18 h at 18° C.

After induction, bacteria were collected by centrifugation followed by washing once in cold 1×PBS (137 mM NaCl, 2.7 mM KCl, 4.3 mM $Na_2HPO_4$, 1.47 mM $KH_2PO_4$, pH 7.4). The bacterial pellets were resuspended in cold 1×PBS at a density of A600=3.5 to 6.5. Some $2 \times 10^8$ aTC-induced bacteria and $2 \times 10^7$ IPTG-induced bacteria (estimated from the A600 value using the relation 0.5 optical density=$5 \times 10^8$ bacteria/ml) were aliquoted into individual 0.2 ml PCR tubes and frozen at −80° C. overnight prior to lyophilization for 3 h at 197 mTorr and −108° C. using the automated settings in a VirTis Benchtop Pro lyophilizer (SP Scientific, Warminster, Pa., USA). Lyophilized cellular reagents were stored with desiccant at room temperature, 37° C., or 42° C. until use.

iv. Purification of RTX Reverse Transcriptase

RTX Exo-polymerase was expressed and purified in house following the protocol of Ellefson et al (2016). Briefly, BL21 DE3 bacteria harboring the pET21-RTX Exo-polymerase containing plasmid was grown overnight in Superior Broth™ at 37° C. Cells were then diluted 1:200, and protein production was induced with 1 mM IPTG during mid-log phase at 18° C. for 16-18 hrs. Harvested cells were flash-frozen and lysed by sonication in 10 mM phosphate, 100 mM NaCl, 0.1 mM EDTA, 1 mM DTT, 10% glycerol, pH 7 buffer containing protease inhibitor (Sigma-Aldrich). Cell lysate was then centrifuged at 40,000 g for 45 min at 4° C. Cleared cell lysates were heated at 85° C. for 25 min, cooled on ice for 20 min, and spun again at 20,000 g for 15 min. Supernatant obtained after centrifugation was filtered using 0.2 nm filters. The filtrate was then passed over an equilibrated heparin column (GE Life Sciences, Pittsburgh, Pa., USA), and eluted along a sodium chloride gradient. Polymerase fractions were collected and dialyzed into Buffer A (Ellefson 2016). Enzymes were further purified using an SP column (GE Life Sciences) and again eluted along a salt gradient. Pooled fractions were then applied to a Sephadex 16/60 size exclusion column (GE Life Sciences), concentrated, and dialyzed into storage buffer (50 mM Tris-HCl, 50 mM KCl, 0.1 mM EDTA, 1 mM DTT, 0.1% Nonidet P40, 0.1% Tween-20, 50% glycerol, pH 8.0). Purified RTX Exo-polymerase was quantified by Pierce BCA protein assay kit (Thermo Fisher Scientific).

v. Overlap Extension Assay Using Taq DNA Polymerase

Taq DNA polymerase-expressing Top10 *E. coli* cells were cultured and processed as cellular reagents as described above. Prior to freeze drying, an aliquot containing $2 \times 10^8$ of these freshly cultured cells was resuspended in 30 µL 1×PBS and centrifuged for 1 min at 13,000 rpm. The resulting supernatant was collected in a fresh tube while the cell pellet was resuspended in 30 µL water. Taq DNA polymerase activities were measured in 3 µL aliquots of the supernatant and in $2 \times 10^7$ prepared cells (contained in 3 µL aliquots) using overlap extension assays executed as follows. Forty seven microliter reactions containing 2 µM each of overlapping oligonucleotides OE.FWD and OE.REV, 1× Thermopol buffer (NEB) (20 mM Tris-HCl, 10 mM $(NH_4)_2SO_4$, 10 mM KCl, 2 mM $MgSO_4$, 0.1% Triton®-X-100, pH 8.8), and 0.2 mM deoxyribonucleotides (dNTPs) were assembled and heated to 95° C. for 1 min followed by cooling on ice for 2 min. Then, 3 µL supernatant or 3 µL cells ($2 \times 10^7$) were added to the reactions, which were then incubated for 1 h at 37° C., 42° C., 65° C., or 75° C. Negative control reactions were performed in the same manner with the exception that water was used instead of OE.FWD and OE.REV oligonucleotide templates. A second aliquot of $2 \times 10^8$ cells was first frozen in 1×PBS at −80° C. prior to testing for Taq DNA polymerase activity in cells and supernatant as described above. A third aliquot of $2 \times 10^8$ cells was frozen in 1×PBS and then lyophilized prior to rehydration with 30 µL water and testing for Taq DNA polymerase activity in oligonucleotide extension assays. Supernatant could not be separated from this rehydrated sample under the centrifugation conditions described above. All oligonucleotide extension products were analyzed by ethidium bromide agarose gel electrophoresis.

vi. Endpoint PCR Using Fresh Broth Culture of Cellular Reagents

BL21 DE3 bacteria transformed with RTX Exo-polymerase expression plasmid were grown to logarithm phase in Superior Broth™ and induced with 1 mM IPTG. One milliliter culture of induced cells was centrifuged at 16,000 g for 1 min. Supernatant was removed and bacteria were resuspended in 1 ml PBS. 1 µl of this neat or 1:10 diluted bacterial suspension was added to a 20 µl PCR reaction containing 10 ng ($1 \times 10^8$ copies) of *Chlamydia trachomatis* 16s rDNA templates in 1×PCR proof reading assay buffer (60 mM Tris-HCl (pH8.4), 25 mM $(NH_4)_2SO_4$, 10 mM KCl and 1 mM $MgSO_4$) supplemented with 0.5 mM dNTPs and 400 nM each of forward (CT.F) and reverse (CT.R) primers. In positive control PCR reactions, RTX Exo-expressing bacterial suspension was replaced with 1 µl of purified RTX Exo-polymerase (0.2 mg/ml stock) or with commercially available KOD DNA polymerase (Sigma Aldrich, St. Louis, Mo.). Reactions were incubated at 95° C. for 5 min followed by 25 cycles of 20 sec at 95° C., 20 sec at 55° C., and 20 sec at 68° C. PCR products were analyzed by electrophoresis through a 1.5% agarose gel prepared in 1×TAE Buffer (22 mM Tris, 180 mM-borate, 5 mM EDTA pH 8.3). Some 0.5 µg/ml of ethidium bromide was included in the gel to visualize the DNA bands under UV light. After running the gel at 80 Volts for 30 min, bands were visualized using ChemiDoc Imager (Bio-Rad).

vii. Endpoint PCR Using Taq DNA Polymerase Lyophilized Cellular Reagents

Endpoint PCR reactions were assembled in 50 µL volumes containing zero or 10 ng of a pCR2.1-FluB plasmid template along with a final concentration of 500 nM each of pCR.FWD and pCR.REV primers Amplification was performed in 1× Thermopol buffer (NEB) containing 0.2 mM dNTPs and 3 µL ($2\times10^7$ cells) of Taq DNA polymerase cellular reagent rehydrated in 30 µL water immediately prior to use. Following an initial 10 min incubation at 95° C., the reactions were subjected to 30 thermal cycles of 30 sec at 95° C., 30 sec at 55° C., and 1 min at 72° C. Ten microliters of the resultant PCR products were analyzed by agarose gel electrophoresis.

viii. Real-Time LAMP-OSD

LAMP-OSD reaction mixtures were prepared in 25 µl volume containing indicated amounts of human glyceraldehyde-3-phosphate dehydrogenase (gapd) DNA templates along with a final concentration of 1.6 µM each of BIP and FIP primers, 0.4 µM each of B3 and F3 primers, and 0.8 µM of the loop primer. Amplification was performed in 1× isothermal buffer (NEB) (20 mM Tris-HCl, 10 mM $(NH_4)_2SO_4$, 10 mM KCl, 2 mM $MgSO_4$, 0.1% Triton X-100, pH 8.8) containing 0.8 M betaine, 0.8 mM dNTPs, 2 mM additional $MgSO_4$, 16 units of pure Bst 2.0 DNA polymerase, and 100 nM of OSD reporter. Reporters were prepared for use in LAMP assays by annealing 100 nM fluorophore-labeled OSD strands with a 5-fold excess of the quencher-labeled OSD strands by incubation at 95° C. for 1 min followed by cooling at the rate of 0.1° C./sec to 25° C.). In some LAMP-OSD assays commercial Bst 2.0 was substituted either with 16 units of commercial Bst-LF DNA polymerase or with 3 µl ($2\times10^7$ cells) of Bst-LF expressing lyophilized BL21 cellular reagents (rehydrated prior to use in 30 µl water). For real-time signal measurement these LAMP-OSD reactions were transferred into a 96-well PCR plate, which was incubated in a LightCycler 96 real-time PCR machine (Roche, NC, U.S.A.) maintained at 65° C. for 90 min. Fluorescence signals were recorded every 3 min and analyzed using the LightCycler 96 software.

ix. Quantitative PCR

KlenTaq DNA polymerase qPCR reactions were prepared in 25 µl volume containing indicated amounts of *Chlamydia trachomatis* 16S DNA templates along with a final concentration of 0.4 µM each of forward (CT.F) and reverse (CT.R) primers. Amplification was performed in 1× KlenTaq1 buffer (DNA Polymerase Technology) (50 mM Tris-Cl pH 9.2, 16 mM ammonium sulfate, 0.05% Brij 58, and 3.5 mM magnesium chloride) containing 0.4 mM dNTPs, 0.2 µl of pure KlenTaq1 DNA polymerase, and 1× EvaGreen intercalating dye (Biotium, Freemont, Calif.). In some qPCR assays, commercial KlenTaq1 was substituted with 3 µl ($2\times10^7$ cells) of KlenTaq expressing lyophilized BL21 cellular reagents (rehydrated prior to use in 30 µl water). For real-time signal measurement these qPCR reactions were transferred into a LightCycler 96 real-time PCR machine and subjected to 10 min at 95° C. followed by 45 cycles of 10 sec at 95° C. (denaturation), 30 sec at 55° C. (annealing) and 30 sec at 72° C. (extension). Fluorescence signals were recorded during the extension step in each cycle. Following qPCR amplicon melting curve analysis was performed. All data were analyzed using the LightCycler 96 software.

Taq DNA polymerase TaqMan qPCR reactions were prepared in 25 µl volume containing indicated amounts of Zika virus NS5 DNA templates along with a final concentration of 0.32 µM each of forward (Zika-4481_F) and reverse (Zika-4552c) primers (Waggoner 2016) Amplification was performed in 1× Thermopol buffer (NEB) containing 0.4 mM dNTPs, 2.5 units of Taq DNA polymerase, and 80 nM TaqMan probe (Zika-4507c-FAM) (Waggoner 2016). In some assays commercial Taq DNA polymerase was substituted with 3 µl ($2\times10^7$ cells) of Taq DNA polymerase expressing lyophilized BL21 cellular reagents (rehydrated prior to use in 30 µL water). For real-time signal measurement these TaqMan qPCR reactions were transferred into a LightCycler 96 real-time PCR machine and subjected to 10 min at 95° C. followed by 45 cycles of 15 sec at 95° C. (denaturation) and 30 sec at 55° C. (annealing and extension). Fluorescence signals were recorded during the annealing/extension step in each cycle. All data were analyzed using the LightCycler 96 software.

RTX reverse transcriptase qPCR reactions were prepared in 20 µl volume containing indicated amounts of *Chlamydia trachomatis* or Zika virus-derived DNA templates along with a final concentration of 200 nM each of forward and reverse primers (CT.F/R and Zika-255-F/Zika-256-R, respectively) Amplification was performed in 1×PCR proof reading assay buffer (60 mM Tris-HCl (pH8.4), 25 mM $(NH_4)_2SO_4$, 10 mM KCl and 1 mM $MgSO_4$) containing 0.5 mM dNTPs, 1.5 M Betaine, 1× EvaGreen dye and 80 ng of RTX Exo-polymerase. In some assays, purified RTX polymerase was substituted with 5 µl ($2\times10^6$ cells) of lyophilized cellular reagent (rehydrated prior to use in 50 µl water). For real-time signal measurement these qPCR reactions were transferred into a LightCycler 96 real-time PCR machine and subjected to 5 min at 95° C. followed by 45 cycles of PCR. *Chlamydia trachomatis* template was cycled through 20 sec at 95° C., 20 sec at 55° C. and 20 sec at 68° C. while Zika template was cycled through 30 sec at 95° C., 30 sec at 55° C. and 30 sec at 68° C. Fluorescence signals were recorded during the extension (68° C.) step in each cycle. All data were analyzed using the LightCycler 96 software.

x. Two-Step Quantitative Reverse Transcription (RT) PCR

Indicated amounts of in vitro transcribed and polyacrylamide gel purified Zika virus NS5 RNA templates were mixed with 10 µM reverse (Zika-4552c) primers and 1 mM dNTP in a total volume of 10 Primer template annealing was performed by incubating the solutions at 65° C. for 5 min followed by 2 min on ice. Reverse transcription was initiated by adding a 10 µl solution containing 2×MMLV RT buffer (NEB) (100 mM Tris-HCl, 20 mM DTT, 150 mM KCl, 6 mM $MgCl_2$, pH 8.3), 8 units of RNase inhibitor and 3 µl ($2\times10^7$ cells) of MMLV reverse transcriptase expressing lyophilized cellular reagents (rehydrated prior to use in 30 µl water). Following 1 h of reverse transcription at 42° C., 5 µl of the resulting cDNA-containing solution was analyzed by TaqMan qPCR using Taq DNA polymerase expressing lyophilized BL21 cellular reagents as described above.

xi. One Pot Quantitative Reverse Transcription (RT) PCR Using RTX Polymerase

One-pot RT-qPCR reactions using pure or cellular RTX Exo-reagent and indicated copies of Zika virus-derived RNA templates were assembled using the same procedure as RTX qPCR described above but with the addition of 10 mM DTT. For real-time signal measurement these RT-qPCR reactions were transferred into a LightCycler 96 real-time PCR machine and subjected to 68° C. for 30 min followed by 5 min at 95° C. prior to 45 cycles of 30 sec at 95° C., 30 sec at 55° C. and 30 sec at 68° C. Fluorescence signals were recorded during the extension (68° C.) step in each cycle. All data were analyzed using the LightCycler 96 software.

xii. Cellular PCR (cPCR) Using Lyophilized Phusion Cellular Reagents

Bacteria containing target DNA sequences were grown overnight at 37° C. and 250 rpm in 3 ml 2×YT broth containing the appropriate antibiotics for selective pressure. Following overnight growth, cultures with A600 of 5 to 6 were diluted 1:10 in sterile water. Two microliters of this diluted culture was added to cPCR reaction to initiate amplification. cPCR reactions were assembled in a total volume of 50 µl containing 1×HF buffer (NEB), 0.2 mM dNTP mix, 0.2 µM each of forward and reverse primers and 3 µl of Phusion cellular reagent (prepared by rehydrating $2 \times 10^8$ lyophilized Top10 E. coli expressing Phusion DNA polymerase in 30 µl water). cPCR reactions were incubated at 95° C. for 10 min followed by 30 cycles of 30 sec at 95° C., 30 sec at 60° C., and 5 min at 72° C. cPCR products were analyzed by agarose gel electrophoresis and used directly for Gibson assembly. A portion of cPCR products were subjected to agarose gel purification using Wizard SV gel purification kit (Promega, Madison, Wis., USA) prior to use in Gibson assembly.

xiii. Gibson Assembly and Transformation of Chemically Competent Bacteria

Twenty microliters Gibson assembly reactions were assembled by mixing vectors and inserts in 1× Gibson assembly buffer (0.1 M Tris-HCl, pH 7.5, 0.01 M $MgCl_2$, 0.2 mM dGTP, 0.2 mM dATP, 0.2 mM dTTP, 0.2 mM dCTP, 0.01 M DTT, 5% (w/v) PEG-8000, 1 mM NAD) supplemented with pure enzymes or with cellular reagents. Assemblies using pure enzymes contained 0.08 units of T5 exonuclease (NEB), 0.5 units of Phusion DNA polymerase (NEB) and 80 units of Taq DNA ligase (NEB). For Gibson assemblies using cellular reagents the pure enzymes were substituted with individual Top10 E. coli cellular reagents expressing Taq DNA Ligase, Taq DNA polymerase, and T5 exonuclease.

Lyophilized cellular reagents were prepared as follows for use in Gibson assemblies. $2 \times 10^8$ Top10 lyophilized cellular reagents expressing Taq DNA polymerase, T5 exonuclease, or Taq DNA ligase were rehydrated using 30 µl of water. The rehydrated T5 exonuclease cellular reagent was diluted 1:100 in water followed by addition of 1.5 µl aliquot per Gibson reaction. Rehydrated Taq DNA polymerase and Taq DNA Ligase cellular reagents were incubated at 75° C. for 10 min. Three microliters of the heat-treated cellular Taq DNA Ligase was directly added to cellular Gibson assemblies. Heat-treated Taq DNA polymerase cellular reagents were diluted 1:10 in water prior to addition of 1.5 µl aliquot per Gibson assembly.

Linearized vectors and inserts for Gibson assemblies were mixed in the following ratios: Two part assemblies of double stranded gene block (gBlock) inserts (IDT) and linearized vector (agarose gel purified PCR product) contained equimolar ratio of vector (30 ng) and gBlock (3 ng). Two part assemblies of cPCR-amplified vectors and inserts contained 2.5 µl each of unpurified or gel-purified vector and insert cPCR products. Three-part cPCR vector and insert assemblies contained 1.5 µl of cPCR vector fragment 1, 1.5 µl of cPCR vector fragment 2 and 2 µl of insert cPCR.

Negative controls for Gibson assemblies included vectors and inserts in 1× Gibson buffer without any pure enzymes or cellular reagents. All Gibson assemblies were incubated at 50° C. for 1 h prior to transformation.

One microliter of each Gibson assembly was transformed directly into chemically-competent Top10 E. coli bacteria. Briefly, 50 µl home-made competent bacteria (Green 2013) were mixed with the Gibson assembly and incubated on ice for 15 min. Following a 30 sec heat-shock at 42° C. and a 2 min incubation on ice bacteria were allowed to recover for 1 h in 250 µl SOC medium (0.5% Yeast Extract, 2% Tryptone, 10 mM NaCl, 2.5 mM KCl, 10 mM $MgCl_2$, 10 mM $MgSO_4$, 20 mM Glucose) at 37° C. on a rotator. All bacteria were collected by centrifugation and plated on 2×YT agar plates containing appropriate antibiotic selection. Following 18 h at 37° C. bacterial colonies were counted to determine efficiency of Gibson assembly. Representative colonies were verified by Sanger sequencing.

xiv. Statistical Analysis

A minimum of three biological replicates with duplicate or triplicate embedded technical replicates were performed. ANOVA testing was used to determine whether cellular reagents significantly affect the Cq value of a reaction. Two different ANOVA tests were performed. One for PCR like reactions and one for LAMP based reactions. For LAMP based reactions, cellular Bst-LF was compared to purified Bst-2.0. Effect sizes were determined using linear regression. The Cq response was modeled as a function of template copy number, the reaction type (e.g. RTX-qPCR, EVG-qPCR KlenTaq, etc.), and reagent type (purified or cellular). The effect size of cellular reagents on Cq value was determined using the "effects" package from the Comprehensive R Archive Network (CRAN) repository. Reactions with either zero template copies or no observed Cq values were omitted from analysis. All models were built using RStudio version 1.0.136.

3) Results i. Development of Cellular Reagents for PCR

Figure 8:
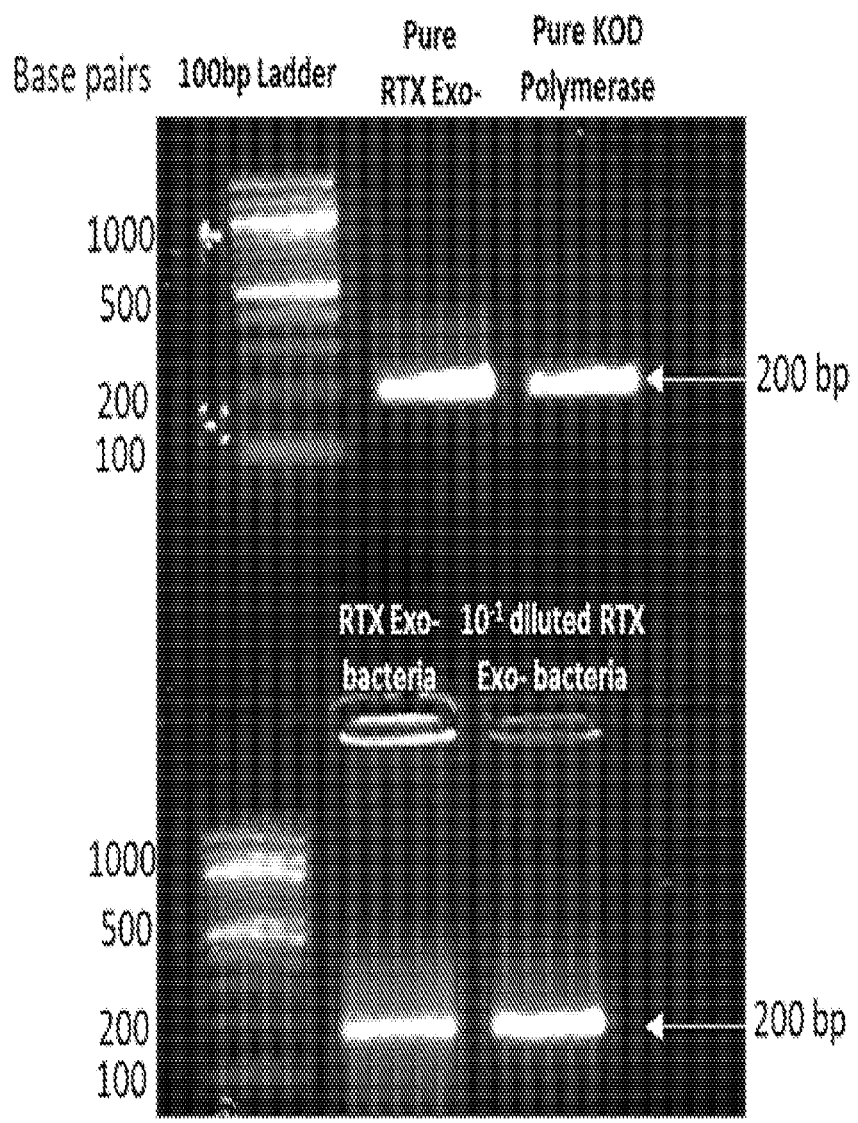
FIG. 8 shows endpoint PCR analysis using fresh culture of RTX Exo-polymerase expressing cellular reagents. Control PCR amplifications performed using pure RTX Exo-polymerase and KOD polymerase are shown in the top panel. Bottom panel depicts PCR products generated using fresh (non-lyophilized) cellular reagents.

To determine the feasibility of using bacteria that express heterologous proteins directly as reagents in molecular biology reactions, PCR using fresh cultures of bacteria expressing RTX Exo-polymerase was carried out. Bands of the expected size (~200 bp), similar to a positive control that contained purified RTX Exo-polymerase or KOD DNA polymerase, were observed (FIG. 8). These results suggest that bacteria expressing a polymerase enzyme could indeed be directly used as reagents without requiring prior purification of the polymerase.

Figure 9A:
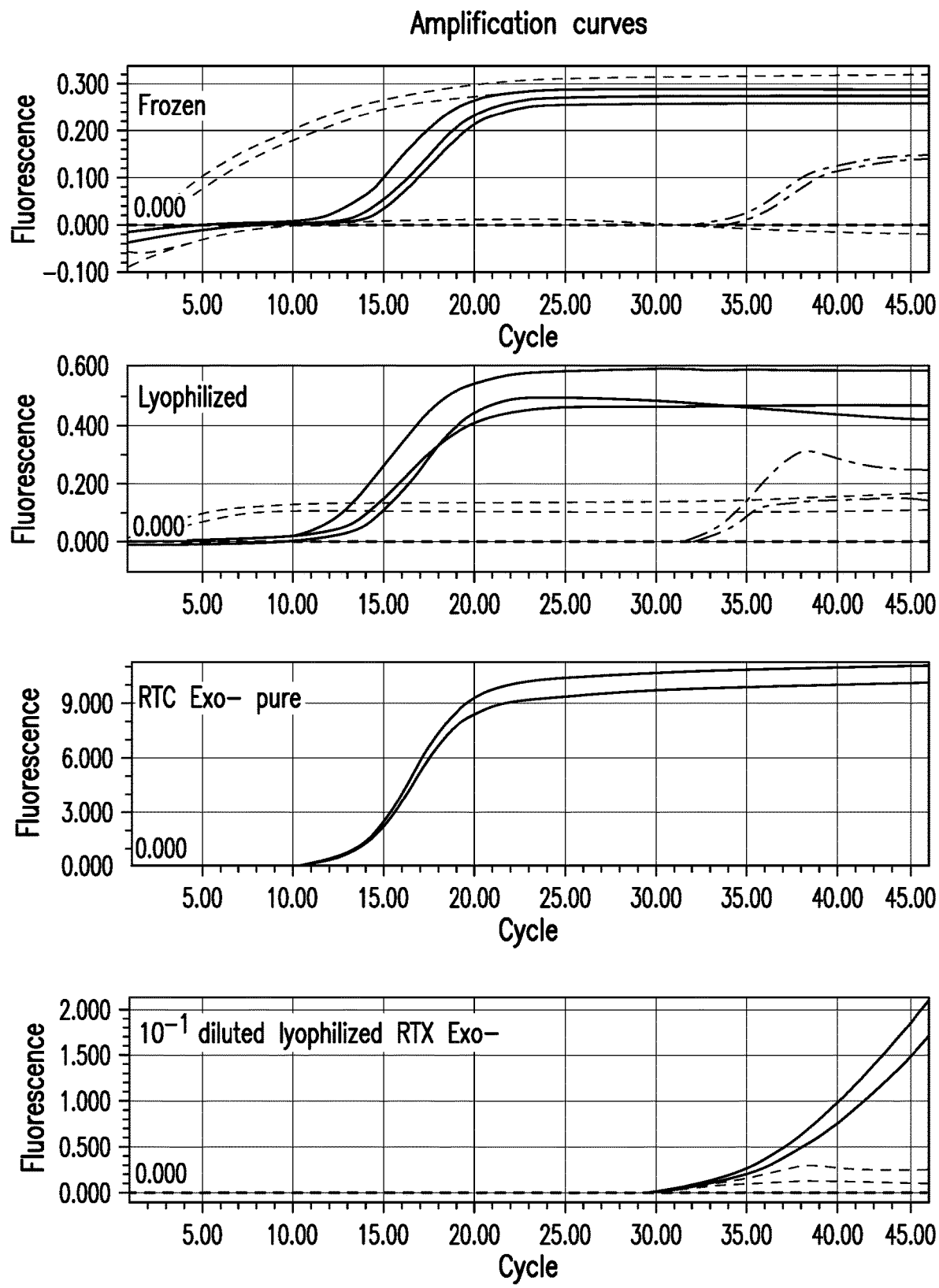
FIG. 9A-B shows PCR amplification efficiencies of lyophilized or frozen RTX Exo-polymerase expressing cellular reagents and purified RTX Exo-polymerase. Synthetic DNA templates derived from *Chlamydia trachomatis* 16S rRNA gene were amplified using purified or cellular RTX Exo-reagents. Amplicon accumulation was measured in real time using EvaGreen fluorescent dye intercalation. Amplification curves generated by RTX Exo-DNA polymerase are shown in A. Amplicon melting temperature peaks generated by performing "Tm calling" analysis using the LightCycler 96 software are depicted on the right. Target-derived amplicons can be readily distinguished from non-specific products by their distinct melting peaks. These amplification curves generated by the "Abs quant" protocol in the LightCycler 96 software depict the rate of change of the rate of change of fluorescence. BL21 DE3 cells that do not express RTX polymerase only yield background fluorescence with or without template as evident from the raw fluorescence curves depicted in B. The difference in the background level of fluorescence of frozen versus lyophilized cells might be a reflection of the lyophilization-induced alterations in bacterial cells.
Figure 9A:
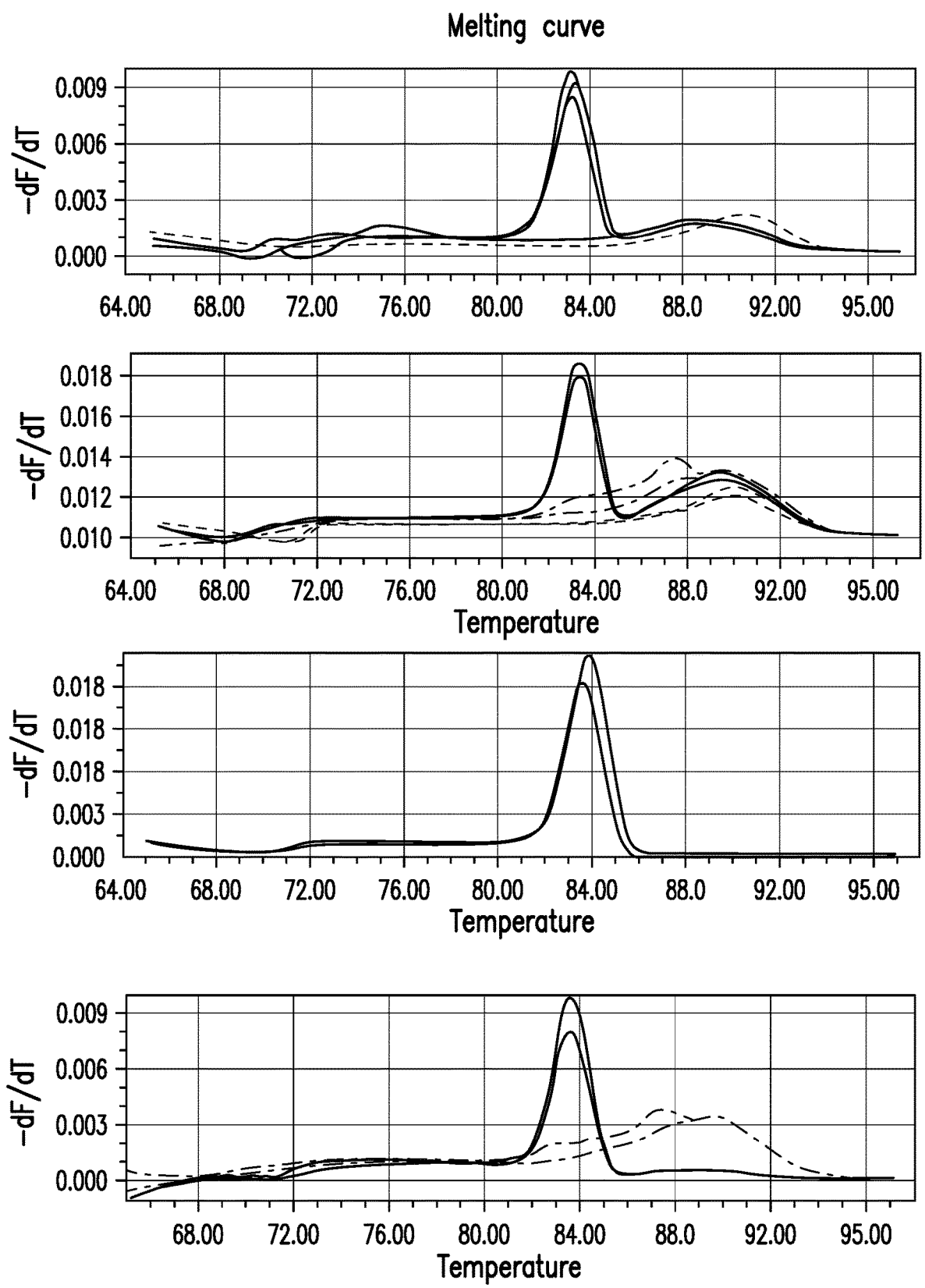
Figure 9B:
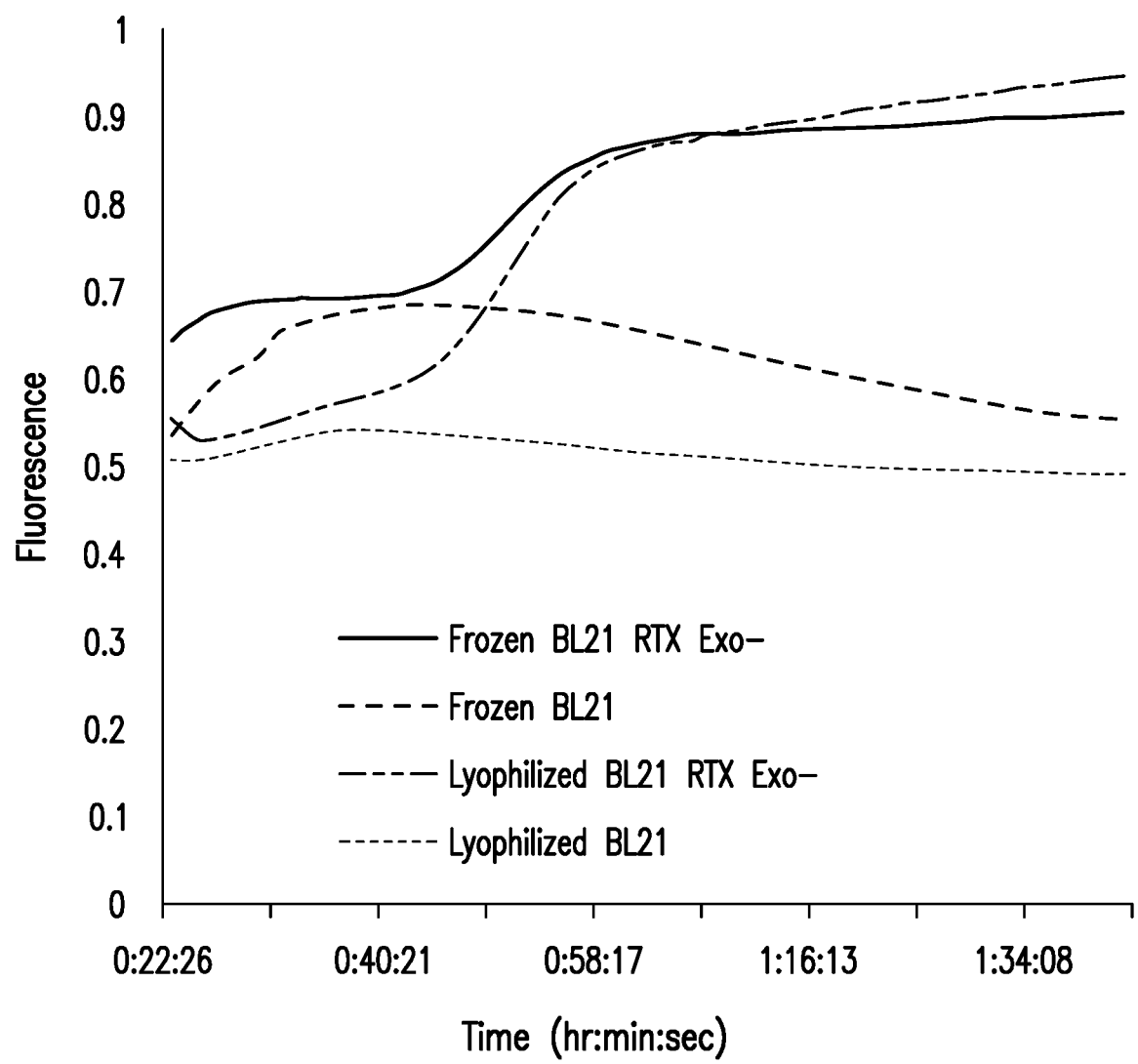
Figure 10A:
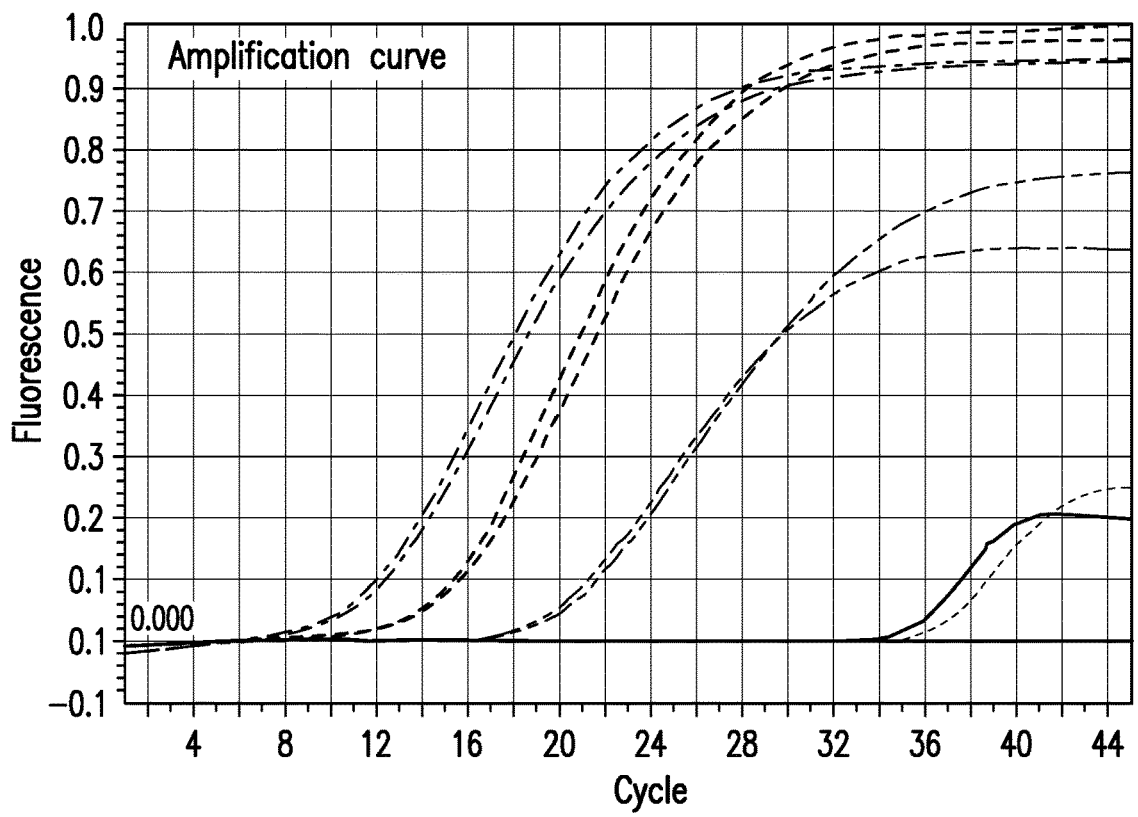
FIG. 10A-D shows qPCR analysis using lyophilized RTX Exo-expressing cellular reagents stored at room temperature for ~80 days. Amplicon accumulation was measured as increase in fluorescence of the intercalating dye EvaGreen. Melting curve analysis of amplicons was performed using the "Tm calling" protocol in the LightCycler 96 software (panel b). This analysis allows identification and distinction of target-derived amplicons whose Tm peak is distinct from the melting temperature of non-specific amplicons. Color coding of the melting peaks is the same as that of the amplification curves. Cq of detecting different template copies is plotted as a bar graph in panel c. Standard curve analysis performed using the "Abs quant" protocol in the LightCycler 96 software is depicted in panel d.
Figure 10B:
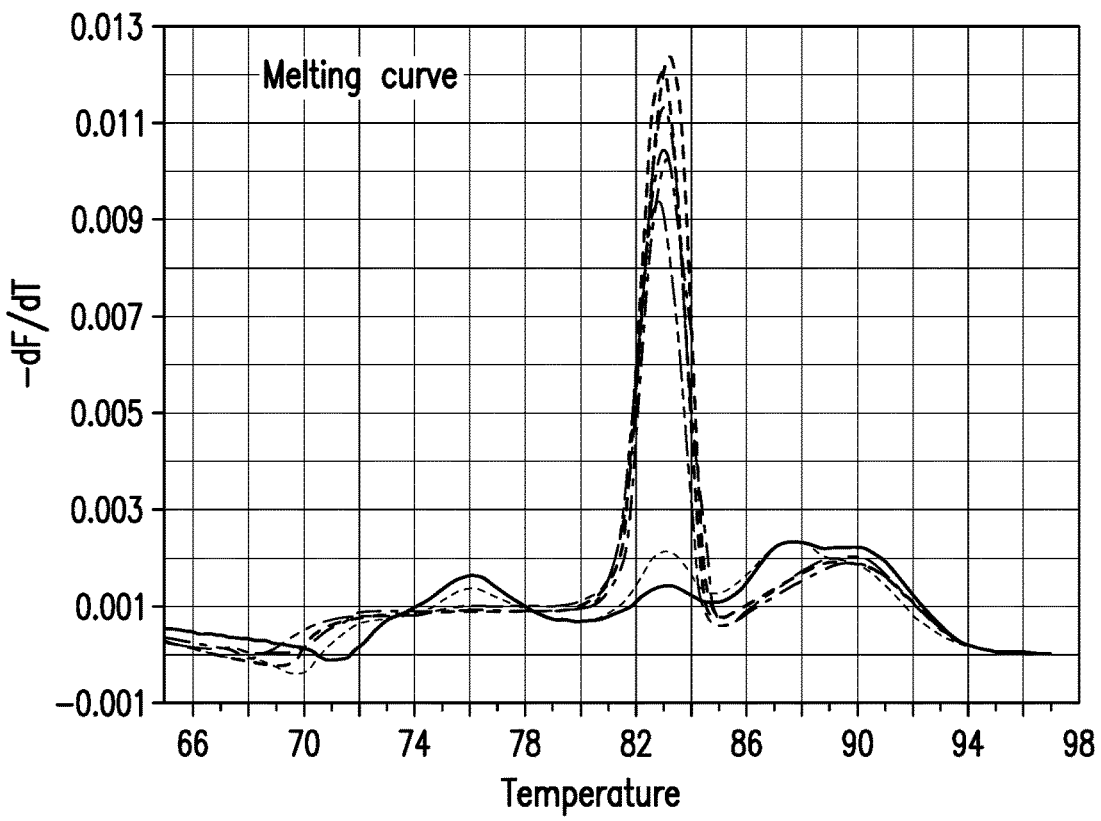
Figure 10C:
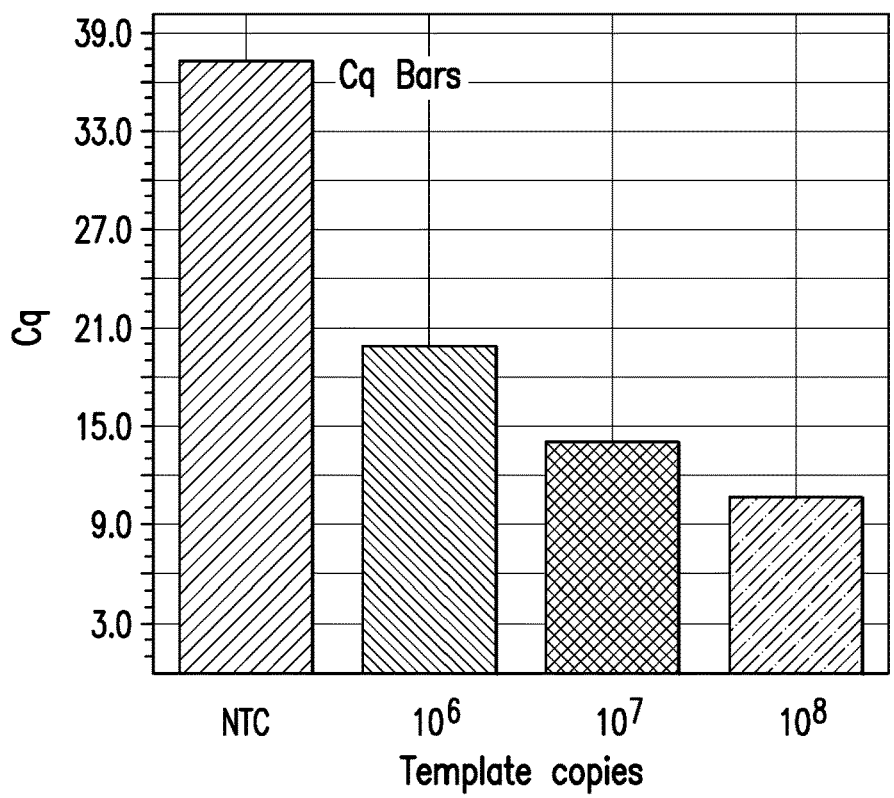
Figure 10D:
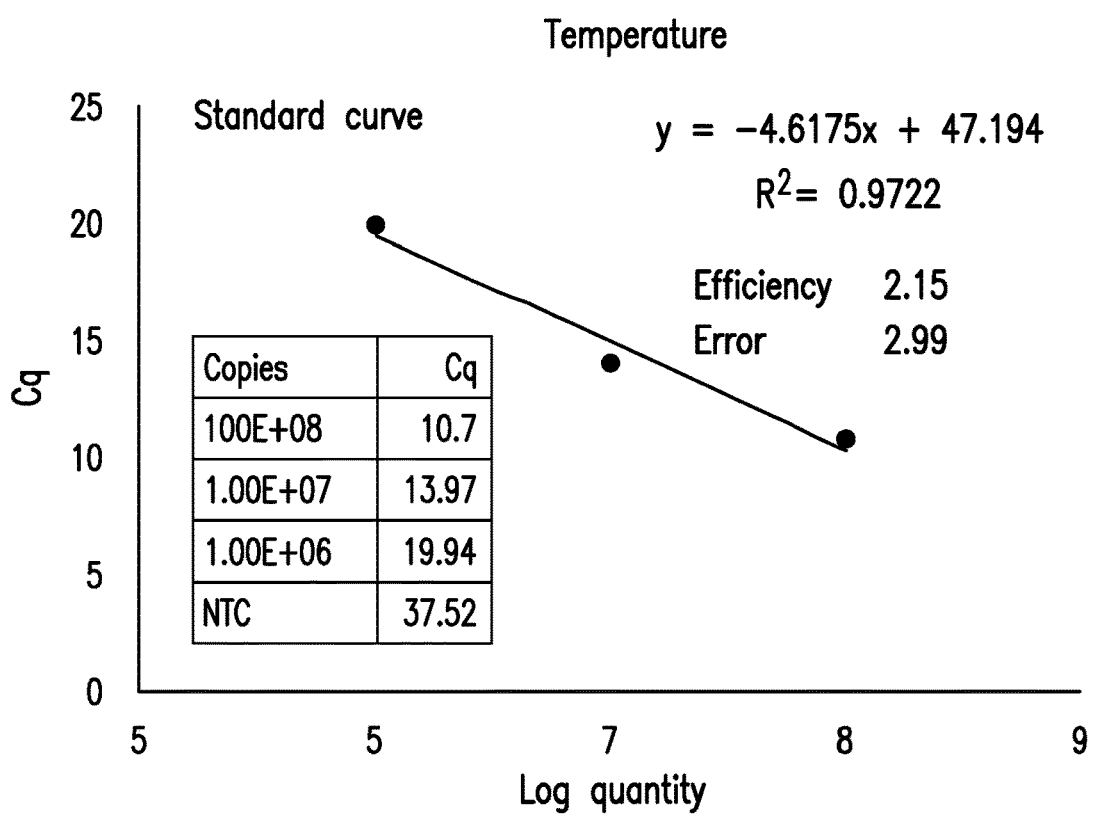

It was also demonstrated that cellular reagents can be stored and used. Overexpressing bacteria were either stored at −80° C. or lyophilized, prior to functional comparison with pure enzymes in qPCR reactions. Enzyme activities of cellular reagents versus corresponding pure enzymes were compared by measuring the Cq values (time to detection) for the same number of template copies. Since there are typically yield losses during protein purification, it is difficult to accurately measure the physical amount of enzyme present in cellular reagents. Therefore, the enzyme activity of defined numbers of RTX Exo-bacterial cellular reagents were compared with the activity of corresponding pure RTX enzymes used at an experimentally determined optima of 80 ng per reaction. Similar Cq values for target detection were obtained irrespective of whether $2 \times 10^6$ lyophilized cells/reaction or 80 ng of purified polymerases were used (FIG. 9). Frozen cellular reagents or $2 \times 10^5$ lyophilized cells/reaction yielded somewhat higher (less sensitive) $C_q$ values (FIG. 9).

Figure 11:
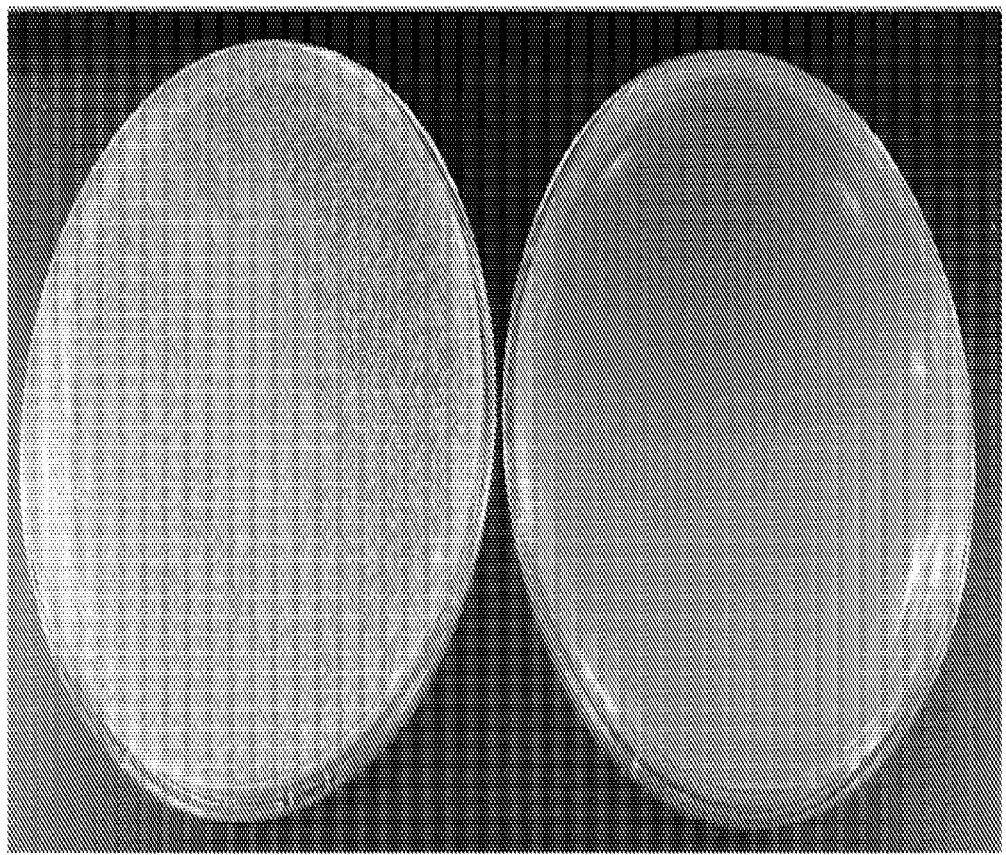
FIG. 11 shows an assessment of bacterial viability in cellular reagents. BL21 $E.$ $coli$ expressing Taq DNA polymerase were lyophilized in either 1×PBS or in 1×PBS supplemented with 0.1M trehalose. After 3 days of storage at ambient temperature, the lyophilized cellular reagents were rehydrated in 30 μL water and half of the material was spread plated on Luria Bertani agar plates. Images of these plates were taken after overnight incubation at 37° C. Only bacteria that were lyophilized in the presence of trehalose retained viability. Cellular reagents lyophilized without trehalose do not remain viable.

Given that conventional wisdom would have suggested that the addition of a highly complex mixture of enzymes and metabolites (i.e., a cell, lyophilized or lysed) to a reaction might have resulted in significant background amplification, an examination of additional negative controls was especially important. While purified enzyme did not generate spurious amplicons, frozen or lyophilized bacteria expressing RTX Exo-polymerase generated a small amount of non-specific signal in the absence of templates. These non-specific signals, however, are readily distinguished from specific amplicons by performing melt curve analysis. Lyophilized BL21 DE3 bacteria that do not harbor the RTX Exo-polymerase generated linear background curves without measurable Cq values when presented with $1 \times 10^8$ templates. Since lyophilized cellular reagents demonstrated comparable qPCR performance as pure enzymes and were stable at room temperature storage for at least 80 days (FIG. 10) the focus was on the development of lyophilized cellular reagent toolkits for potential diagnostic and molecular biology applications. Lyophilized cellular reagents have the added advantage of biosafety; *E. coli* lyophilized without excipients (such as trehalose) do not retain viability (FIG. 11) (Seetharam 2009; Wessman 2013), and therefore are safer for distribution and use.

Figure 12:
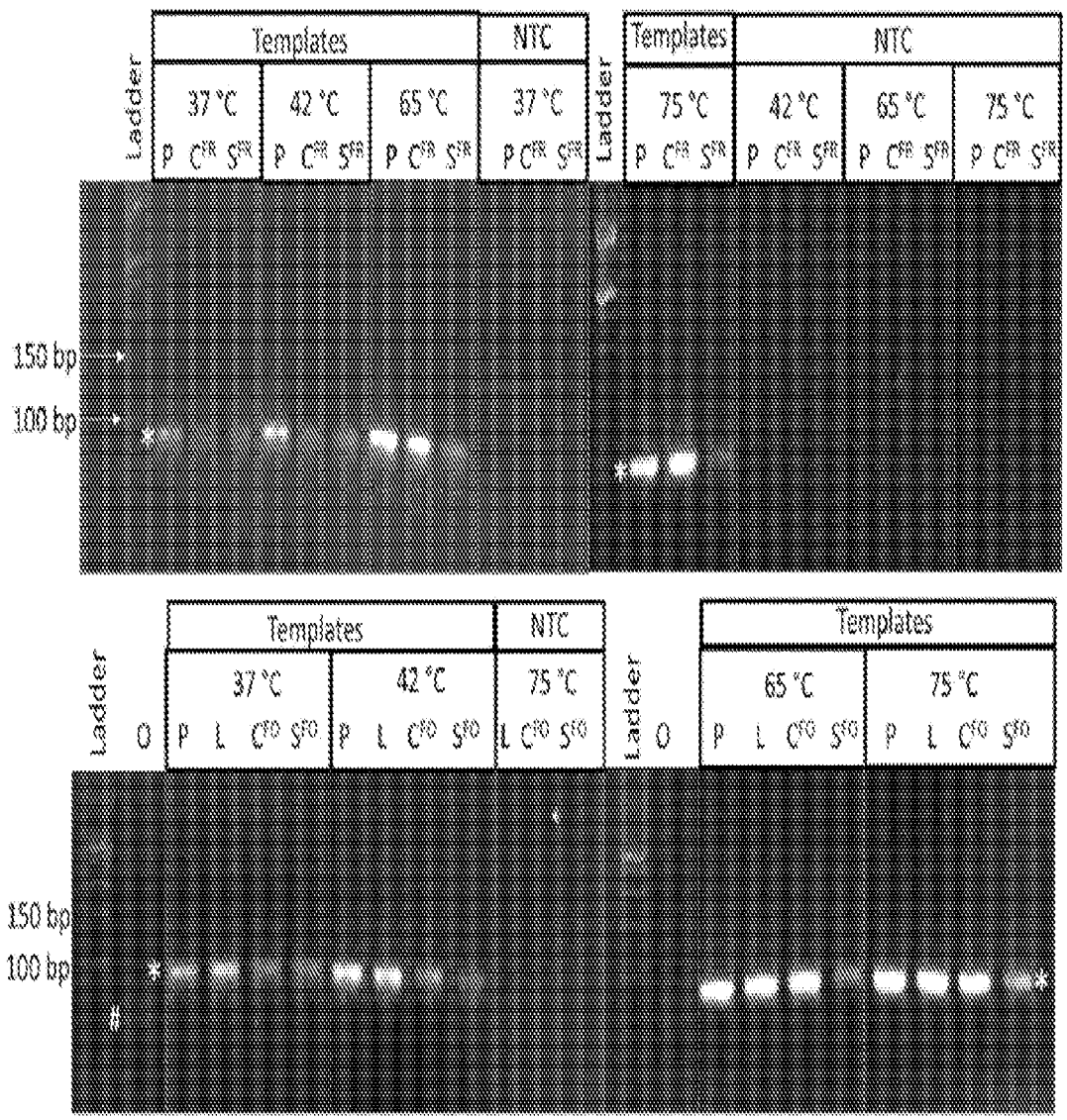
FIG. 12 shows overlap extension assays to evaluate enzyme accessibility in cellular reagents. BL21 $E.$ $coli$ cells overexpressing Taq DNA polymerase were washed in PBS and assessed for enzyme activity in three different conditions: fresh cells (FR), cells frozen at −80° C. (FO), or lyophilized (L) cells. Cells (C) were tested isothermally by single step overlap extension assays at four different temperatures—37° C., 42° C., 65° C., and 75° C. The PBS supernatants (S) leftover after pelleting fresh (SFR) or frozen (SFO) cells were also tested for polymerase activity. Overlap extension performed using pure (P) commercial Taq DNA polymerase served as the positive control. Reactions performed in the presence of oligonucleotide templates are labeled 'Templates'. Negative controls lacking templates are denoted as 'NTC'. All overlap extension products (indicated by '*') were analyzed by agarose gel electrophoresis. Overlap extension template oligonucleotides (O; indicated with '#') were analyzed as controls.

Next, it was determined if other enzymes commonly used for PCR could be similarly repackaged as simpler ready-to-use cellular reagents. *E. coli* cells overexpressing Taq DNA polymerase were washed in PBS and assessed for enzyme activity in three different conditions: fresh cells, cells frozen at −80° C., or lyophilized cells. Cells were tested isothermally by single step overlap extension assays at four different temperatures—37° C., 42° C., 65° C., and 75° C.—to evaluate accessibility. The PBS supernatants leftover after pelleting fresh or frozen cells were also tested for polymerase activity. Rehydrated lyophilized bacteria could not be separated from supernatant under similar centrifugation conditions. The results demonstrated that most of the Taq DNA polymerase activity is associated with bacterial cells (FIG. 12). Small amounts of activity evident in the supernatants is likely due to contaminating cells and/or cellular components that were not removed by centrifugation. Amplicon output of fresh and frozen cells was similar to that of pure Taq DNA polymerase only at temperatures ≥65° C., showing that these cells likely have intact cell walls that restrict enzyme accessibility and hence observable activity at more mesophilic temperatures. In contrast, the yield of amplicons generated by rehydrated lyophilized cellular reagents was similar to pure enzyme at all temperatures, suggesting unhindered access to the enzyme payload of cellular reagents. It seems osmotic shock can have the same effect as heat treatment for lyophilized cells.

Figure 13:
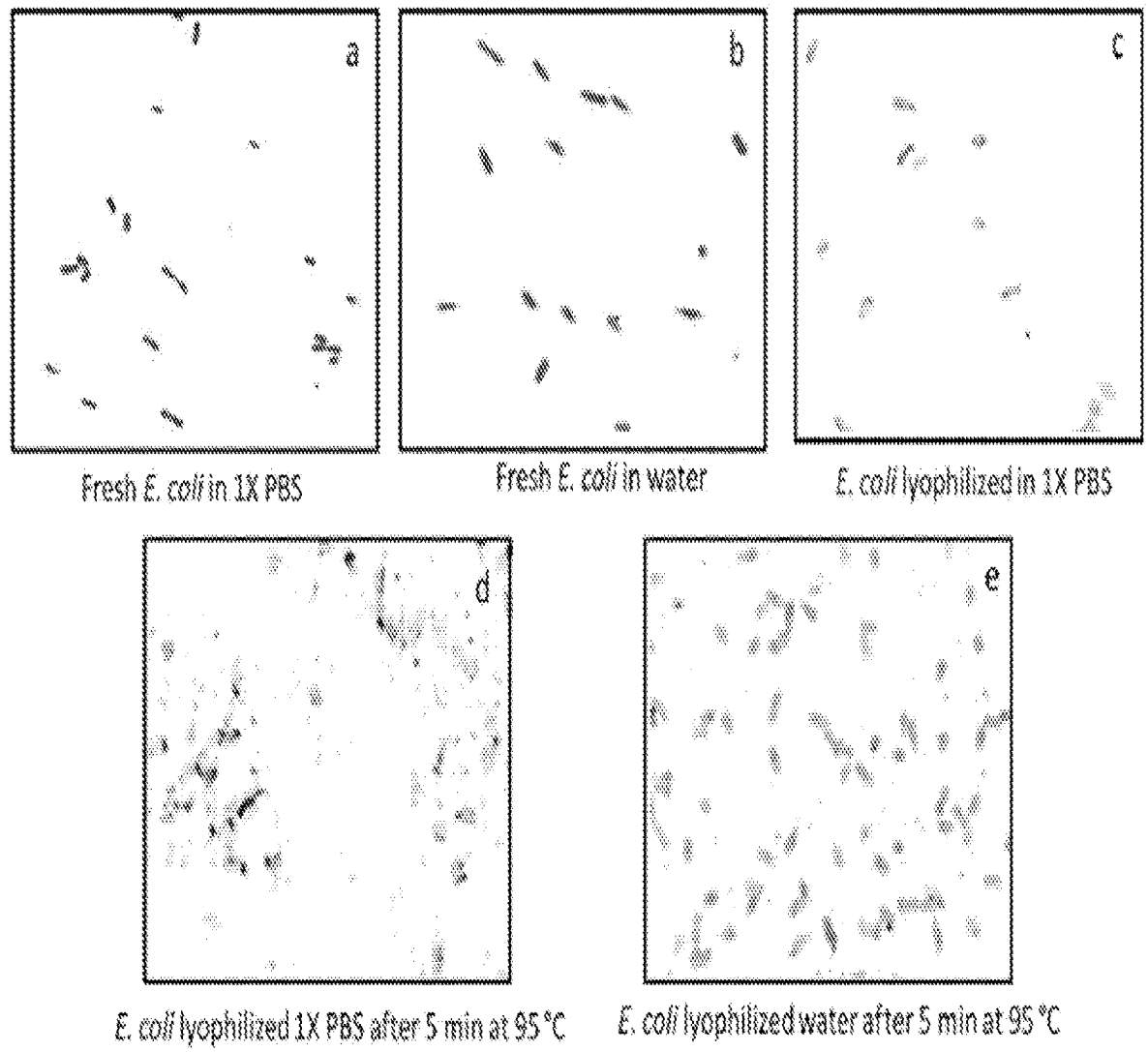
FIG. 13A-E shows microscopic examination of cellular reagents. Freshly cultured $E.$ $coli$ cells overexpressing RTX DNA polymerase were washed and resuspended either in 1×PBS (a) or in water (b) prior to Gram staining and microscopic imaging under oil immersion and a 100× objective lens. Aliquots of these cells were also lyophilized and then rehydrated with water prior to microscopy. Cells lyophilized in 1×PBS are depicted in panel c while lyophilized cells examined after heat treatment are depicted in panels d (cells lyophilized in 1×PBS) and e (cells lyophilized in water).

Microscopic examination of Gram-stained rehydrated cellular reagents revealed that most *E. coli* cells lyophilized in 1×PBS were not dispersed but appeared hollow, unlike similarly stained fresh cells or cells lyophilized in water (FIG. 13). In contrast, upon heating for 5 min at 95° C. rehydrated cells that had been lyophilized in 1×PBS were found to disintegrate while, most rehydrated cells that had been lyophilized in water retained their shape even after heat treatment. These observations suggests that *E. coli* freeze-dried in 1×PBS might have porous walls that allow intermingling of cellular and external reaction contents upon rehydration.

Figure 14:
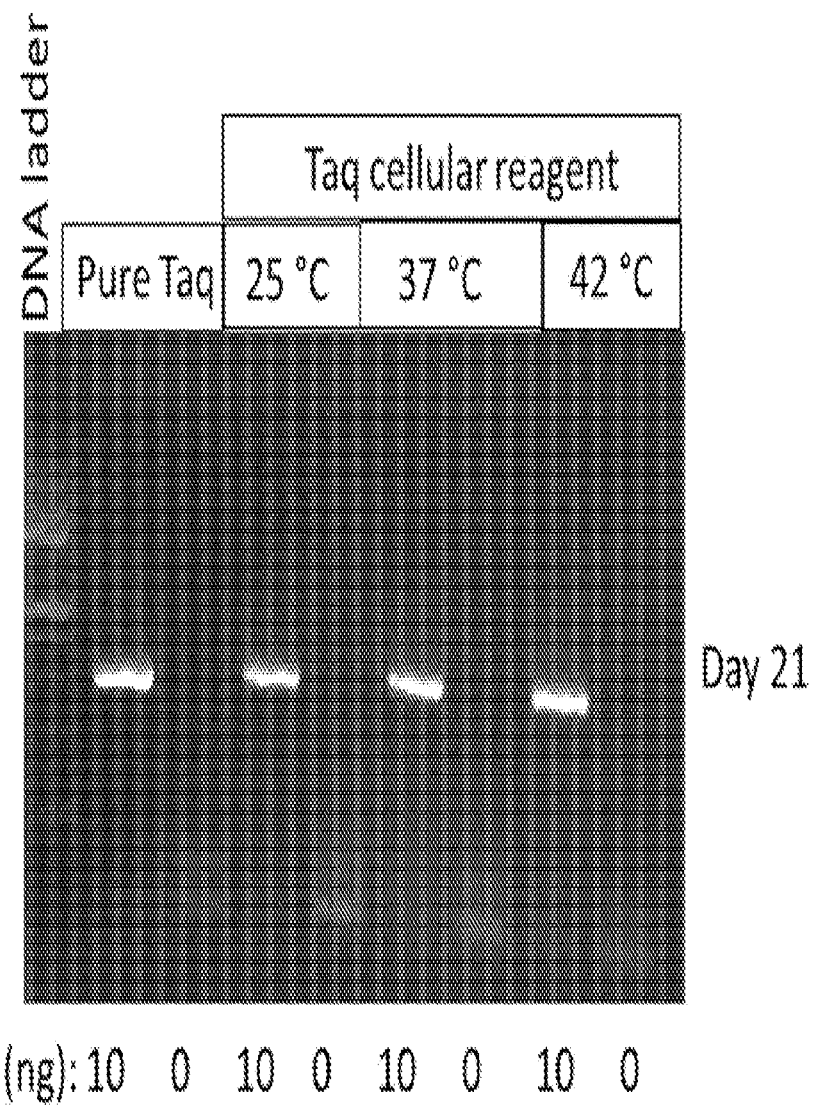
FIG. 14 shows storage stability of Taq DNA polymerase cellular reagents at elevated temperatures. Taq DNA polymerase expressing cellular reagents stored with desiccant at 25° C., 37° C., or 42° C. were tested for activity by using $2×10^7$ cells per reaction in endpoint PCR. Products were analyzed by gel electrophoresis and compared to PCR performed using 2.5 units of pure commercial Taq DNA polymerase. Activity of cellular reagents after 21 days of storage are depicted.
Figure 15A:
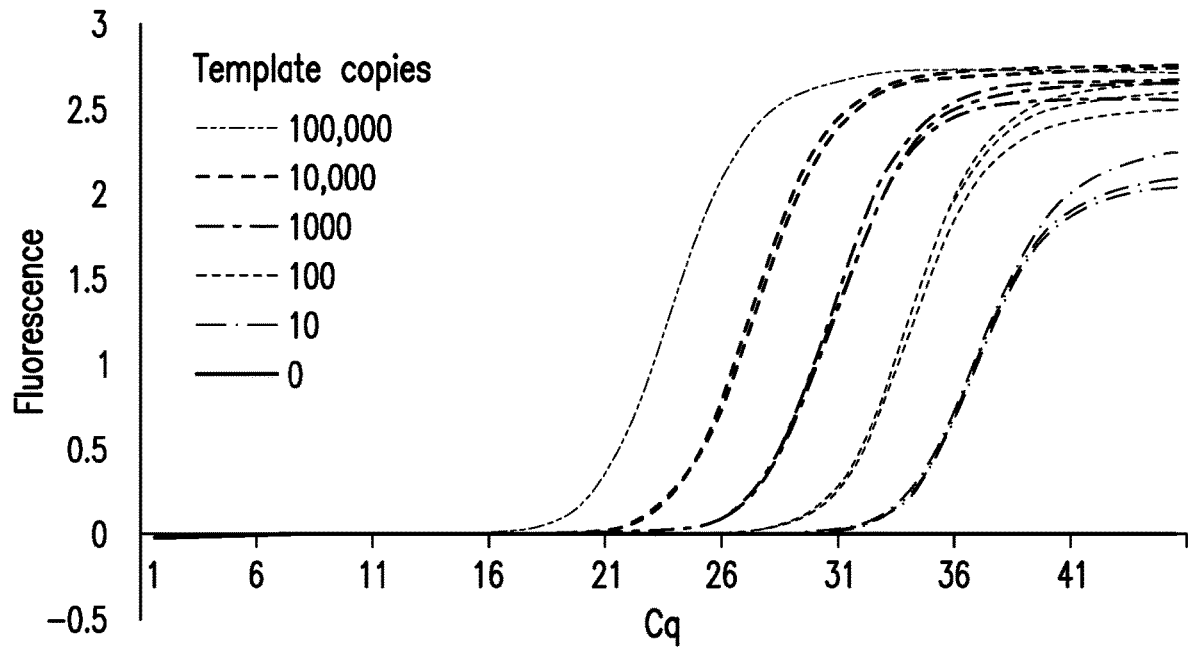
FIG. 15A-B shows standard curve analysis of Zika virus RNA using commercial one-pot qRT-PCR master mix. A. Zika virus derived synthetic RNA template was analyzed by one-pot qRT-PCR using the Evoscript RNA Probes Master mix (Roche) according to the manufacturer's instructions. Briefly, indicated RNA template copies were added to 1×qRT-PCR master mix supplemented with 800 nM each of Zika 4481_F and Zika 4552c forward and reverse primers, and 200 nM of Zika 4507c-FAM TaqMan probe. PCR reactions were first incubated at 60° C. for 30 min to allow reverse transcription. The reactions were then incubated at 95° C. for 10 min prior to executing 45 cycles of 15 sec at 95° C. and 30 sec at 55° C. Amplicon accumulation was measured as increase in TaqMan probe fluorescence Amplification curves obtained using indicated copies of template RNA are depicted. These curves were generated using "Abs quant" analysis protocol in the LightCycler 96 software. B. Standard curve analysis of real-time amplification data shown in panel A.
Figure 15B:
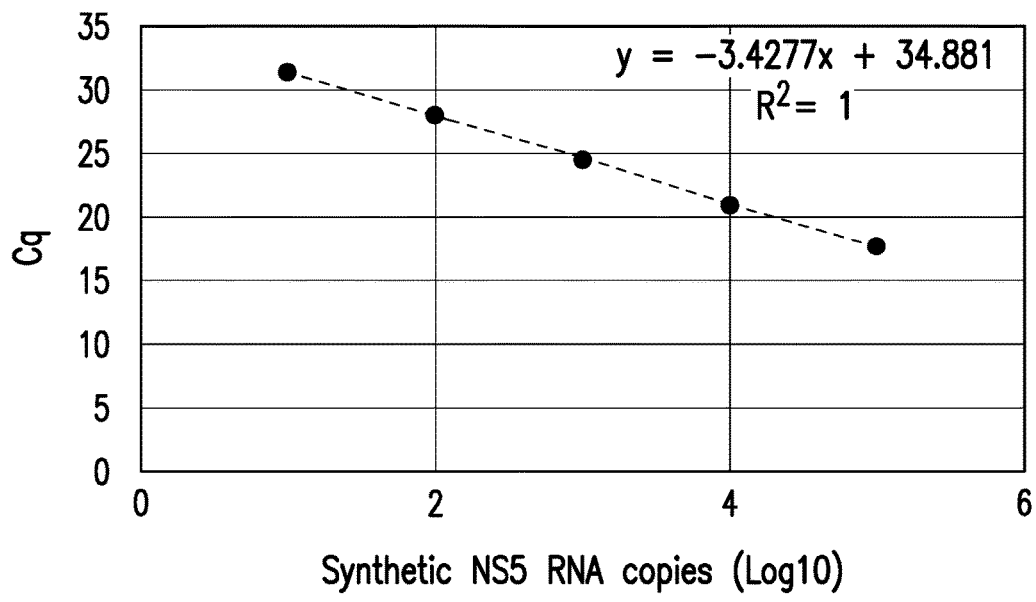

Enzymes other than RTX reverse transcriptase should be compatible with a cellular reagent format, especially since bacterial lyophilization in the presence of PBS is sufficient for enzyme access and additional bacterial lysis procedures are not required. In support of this hypothesis, Taq DNA polymerase cellular reagents also do not require cold storage; at the time of this publication these reagents remained functional even after 3 weeks at temperatures as high as 42° C. (FIG. 14). Indeed, Taq DNA polymerase cellular reagents could replace pure commercial enzymes in the TaqMan qPCR assay, one of the most commonly used gold standards for molecular diagnostic procedures. A previously described molecular diagnostic assay for Zika virus detection (Waggoner 2016) was used as an exemplar, albeit with synthetic DNA, instead of RNA, templates. Defined numbers of Taq DNA polymerase cellular reagents or standard amounts (2.5 units according to the manufacturer) of commercial Taq DNA polymerase were used to amplify the same number of template copies. Polymerase activities were compared by measuring the respective Cq values for the same number of templates. Some $2 \times 10^7$ bacteria bearing Taq DNA polymerase demonstrated similar amplification efficiencies, detection limits, $C_q$ values (time to detection), signal amplitudes, and absence of non-specific signals as added, 2.5 units of purified commercial Taq DNA polymerase (FIG. 1). Most importantly, nucleic acid degradation was not evident in assays carried out with cellular reagents, likely due to inhibition and/or degradation of endogenous nucleases upon thermal cycling. Just as the preparation of thermostable enzymes in mesophilic cells is often abetted by the denaturation or aggregation of non-thermostable proteins (Patchett 1989), the same phenomenon can assist with molecular diagnostics.

Figures 2A, 2B:
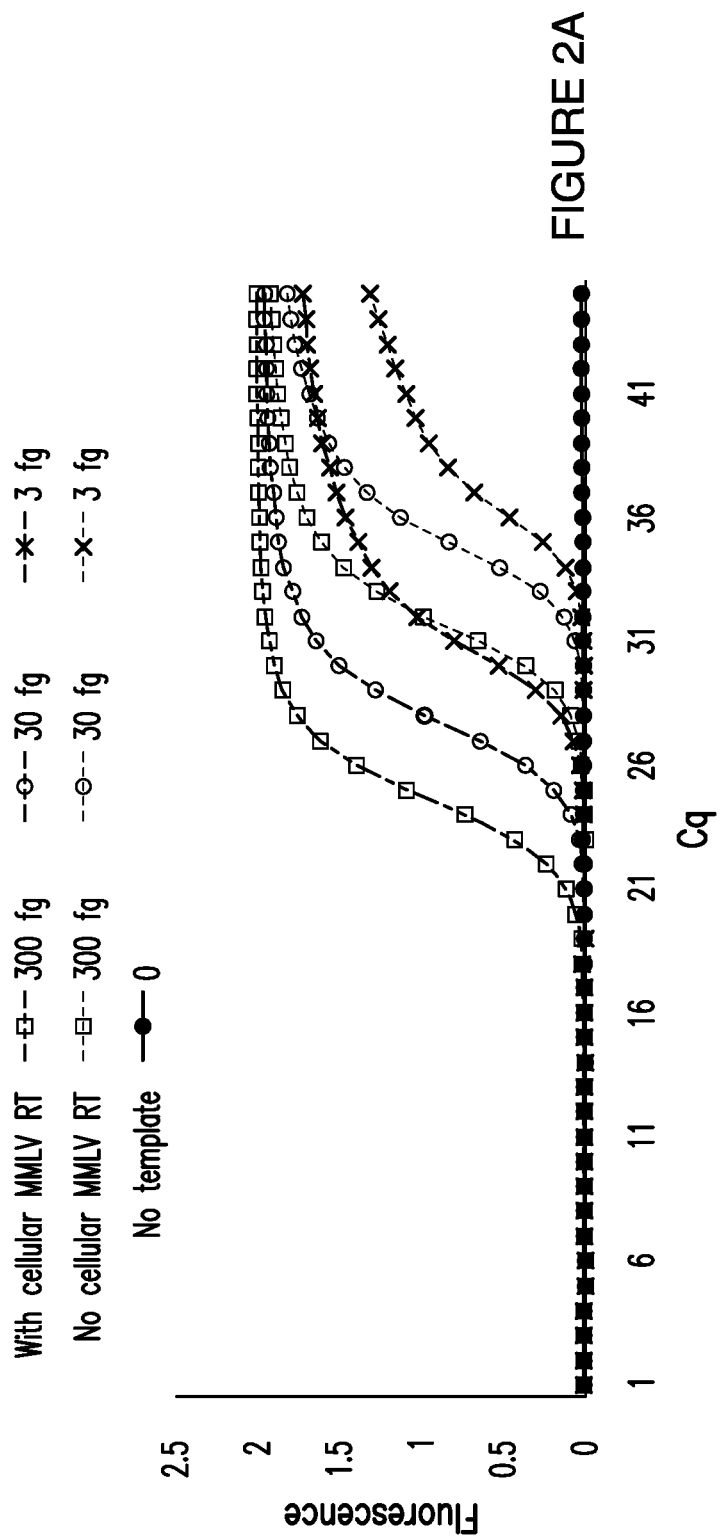
FIG. 2A-B shows RNA detection by two-step reverse transcription TaqMan qPCR using cellular reagents for MMLV RT and Taq DNA polymerase. Indicated copies of synthetic RNA template derived from Zika virus genomic sequence were tested using $2 \times 10^7$ cells each of MMLV RT and Taq DNA polymerase lyophilized cellular reagents. Amplification was assessed in real-time by measuring increase in TaqMan probe fluorescence over time. Representative amplification curves generated using the "Abs quant" analysis in the LightCycler 96 software are presented (A). The corresponding derivation of template copies from Cq analyses are tabulated (B). Cq values were converted to template copies using standard curve analyses of the same RNA samples with commercial qRT-PCR master mix.
Figure 3B:
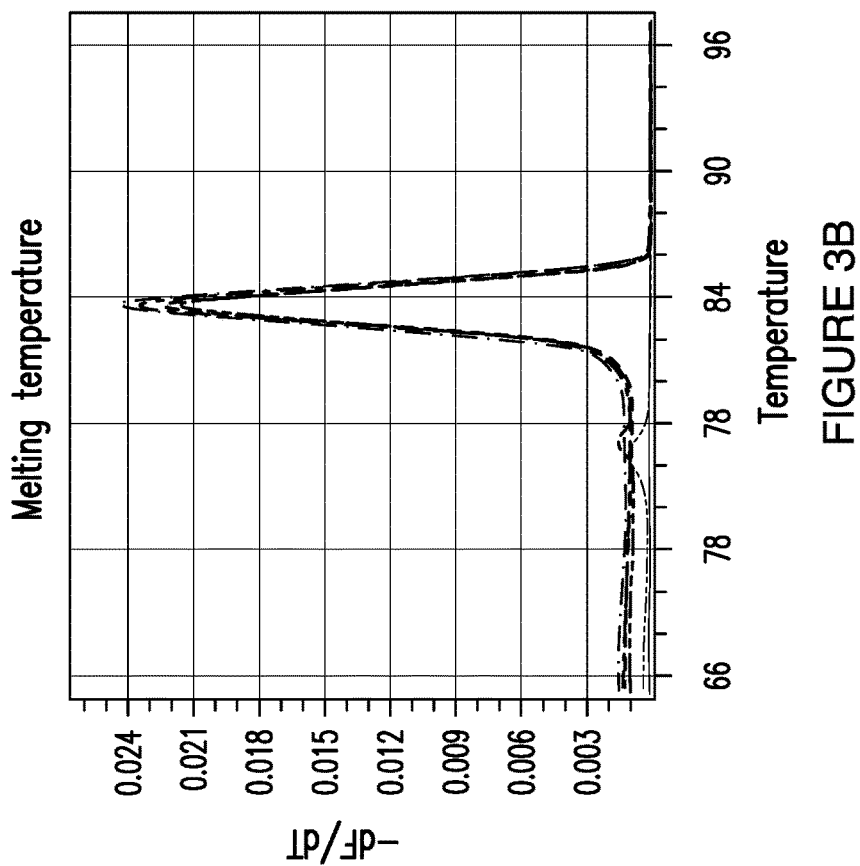
FIG. 3A-F shows EvaGreen qPCR analysis using KlenTaq DNA polymerase expressing cellular reagents. Indicated copies of synthetic *Chlamydia trachomatis* DNA template were amplified by PCR using 0.2 µL of pure commercial KlenTaq DNA polymerase (panels a, b, and c) or $2\times10^7$ cells of KlenTaq cellular reagents (panels d, e, and f). Amplicon accumulation was assessed in real time by measuring increase in EvaGreen fluorescence. Panels a and d depict representative amplification curves generated using the "Abs quant" analysis in the LightCycler 96 software. Taken together, these curves demonstrate the real-time kinetics of PCR amplification. Since EvaGreen is a non-specific DNA intercalating dye, the fidelity of amplicon generation was verified by determining their melting temperatures (panels b and e) using the "Tm calling" analysis protocol in the LightCycler 96 software. Color coding of the curves is the same as in panels a and d. The overlapping melting temperature peaks of amplicons generated from $6\times10^6$ to 60 copies of templates are indicative of correctly amplified PCR products. Amplification curves observed in the presence of 0 to 6 template copies are non-specific as evident from their different melting temperatures peaks of these amplicons. Standard curve analyses performed using the "Abs quant" protocol in the LightCycler 96 software are depicted in panels c and f, respectively, and data for amplification efficiency, linearity, and error are tabulated as insets.
Figure 3A:
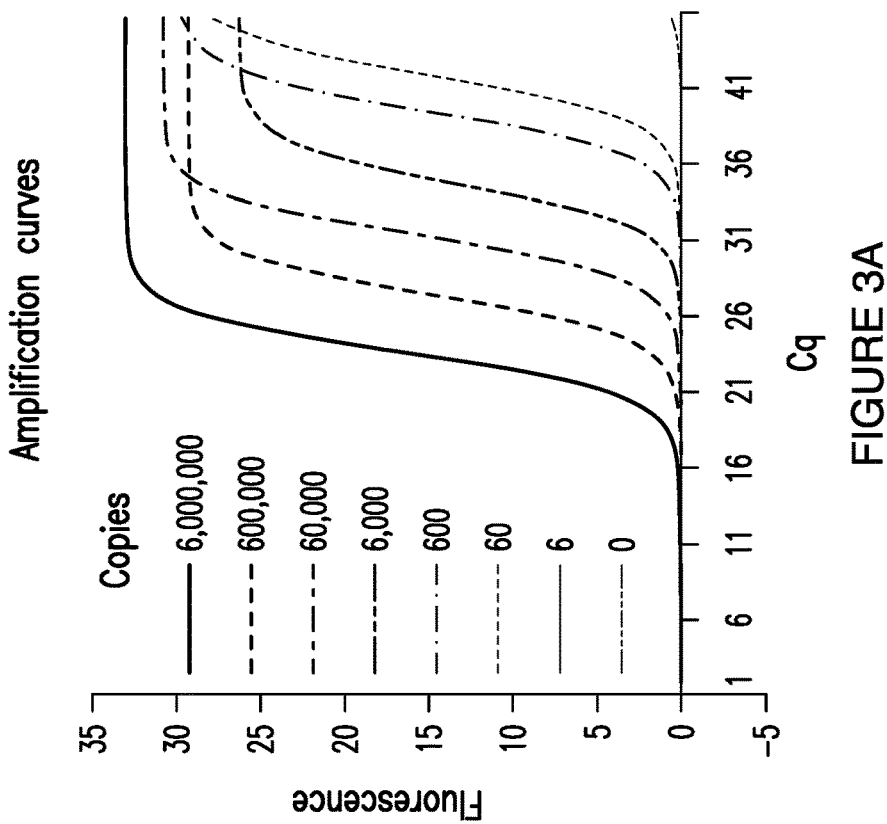
Figure 3D:
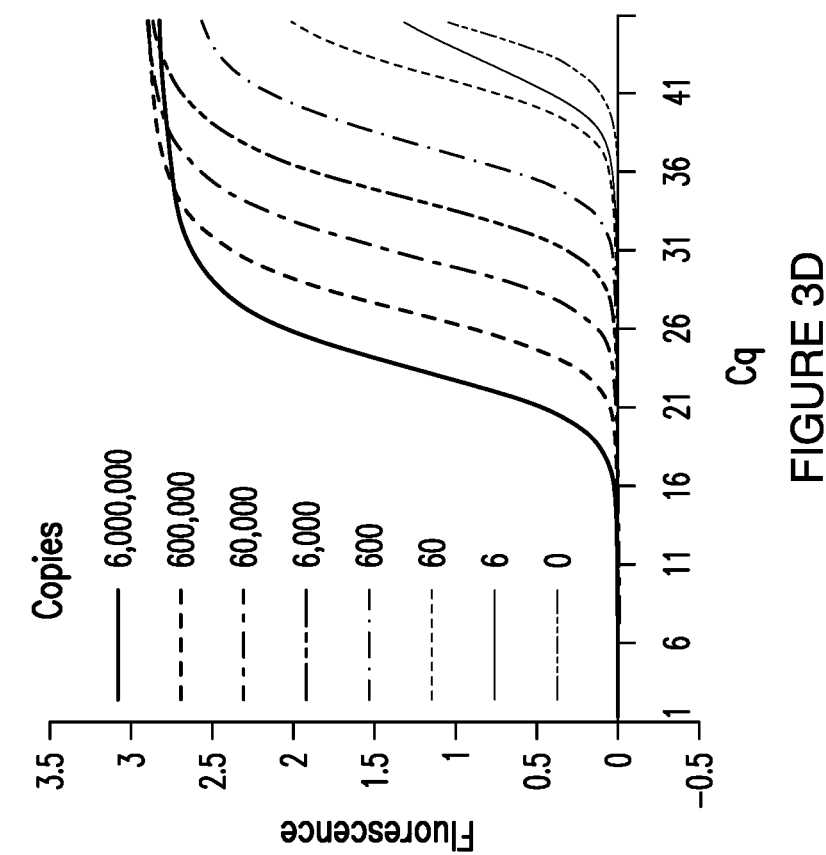
Figure 3C:
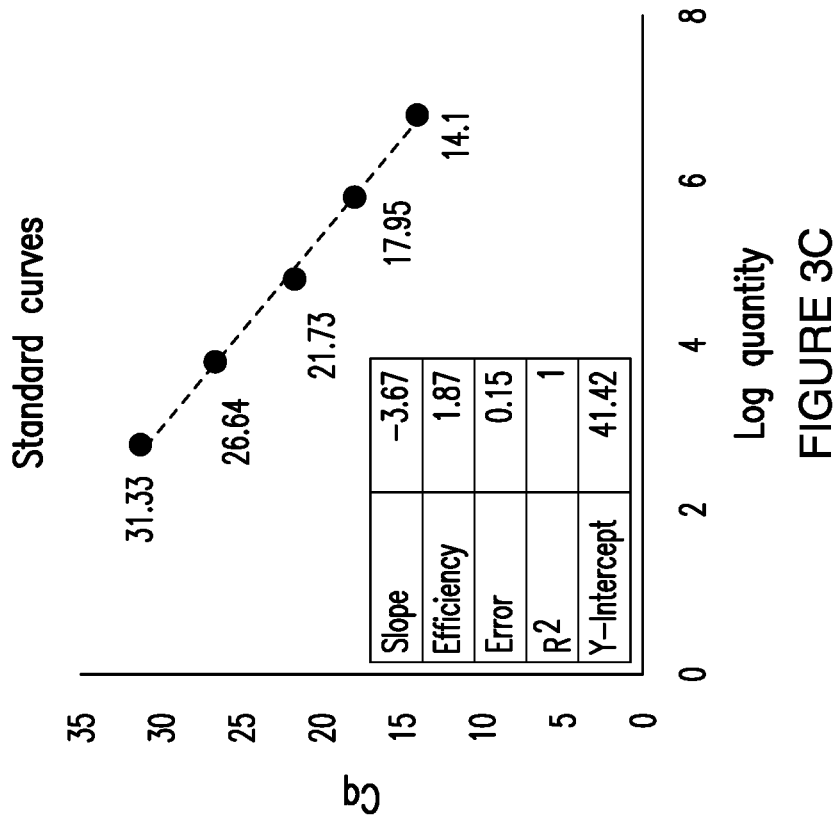
Figure 3F:
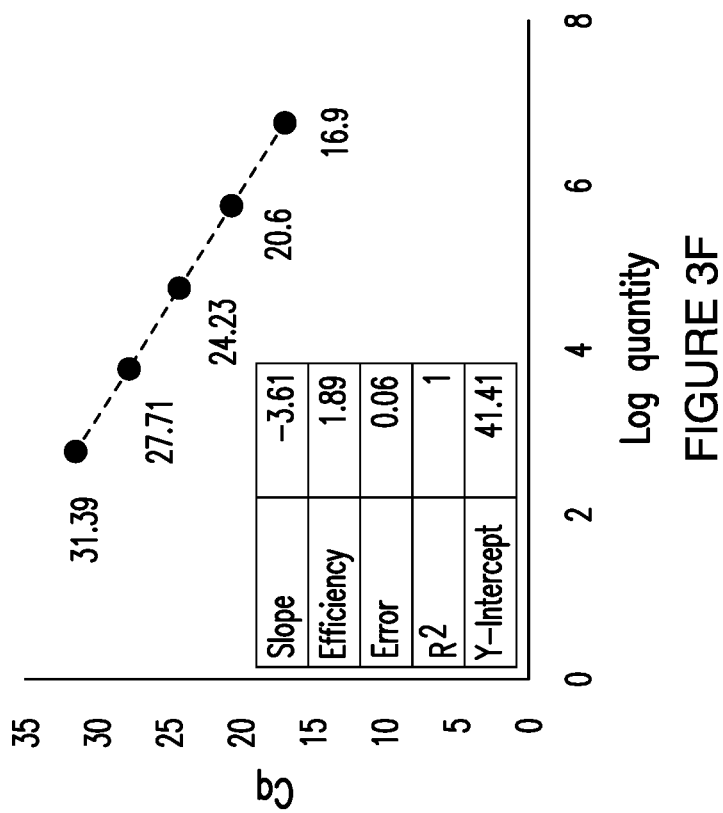
Figure 3E:
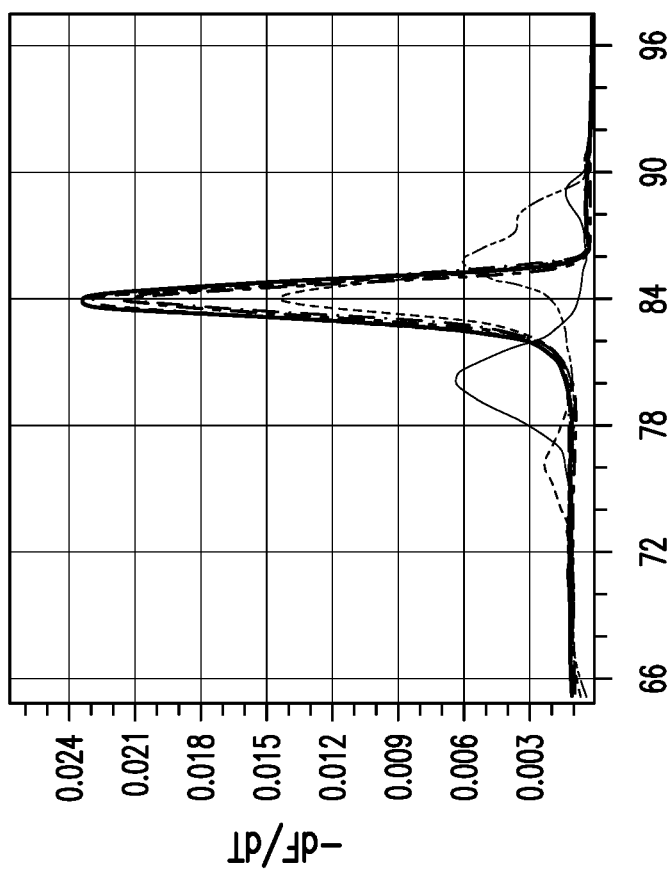
Figure 4B:
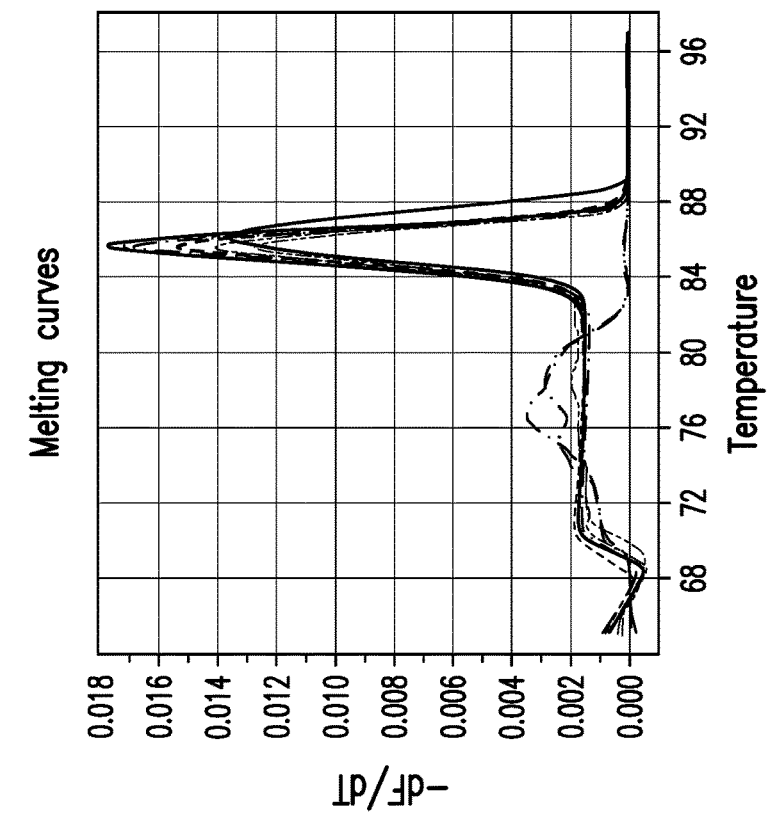
FIG. 4A-F shows EvaGreen qPCR analysis using RTX Exo-DNA polymerase expressing cellular reagents. Indicated copies of synthetic Zika virus derived DNA template were amplified by PCR using 80 ng of pure RTX Exo-DNA polymerase (panels a, b, and c) or $2\times10^6$ cells of RTX Exo-cellular reagents (panels d, e, and f) Amplicon accumulation was assessed in real time by measuring increase in EvaGreen fluorescence. Representative amplification curves using $10^8$, $10^7$, $10^6$, $10^5$, $10^4$, $10^3$, $10^2$, 10 and 0 template DNA copies are shown in panels a and d. 'NTC' refers to no template control. These curves were generated using the "Abs quant" analysis protocol in the LightCycler 96 software. The corresponding amplicon melting temperature analyses performed using the "Tm calling" protocol in the LightCycler 96 software are shown in panels b and e. The melting temperature peaks of target-derived amplicons are distinct from those of non-specific amplicons generated in the absence of templates. Standard curve analyses performed using the "Abs quant" protocol in the LightCycler 96 software are depicted in panels c and f. Standard curve analyses data for comparing amplification efficiency, linearity, and error are tabulated as insets.
Figure 4A:
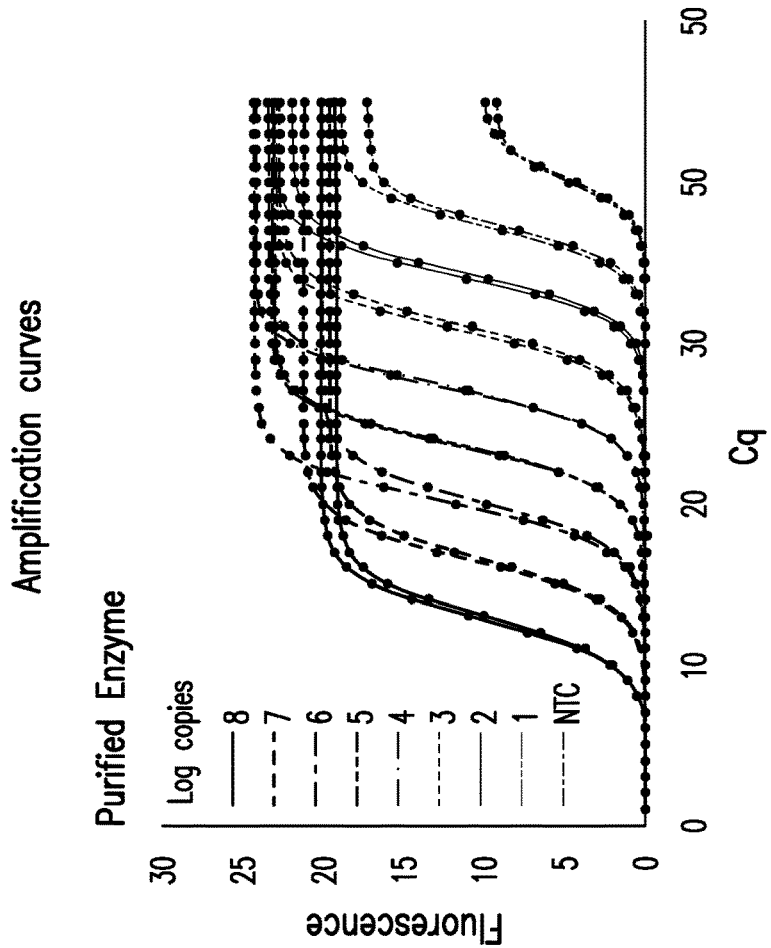
Figure 4C:
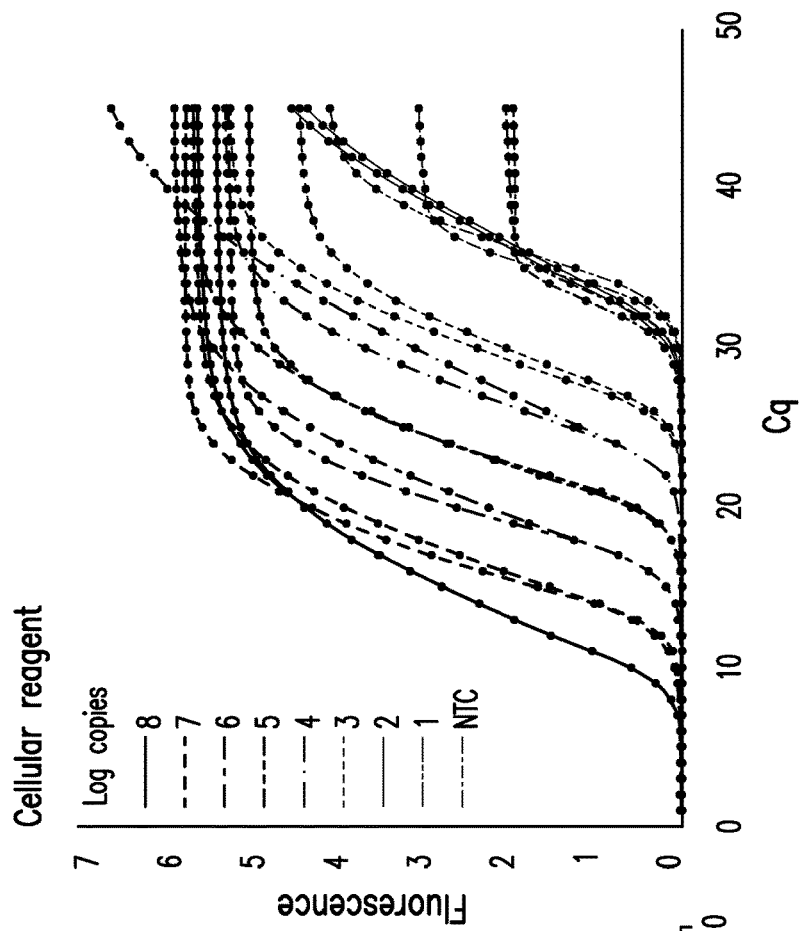
Figure 4D:
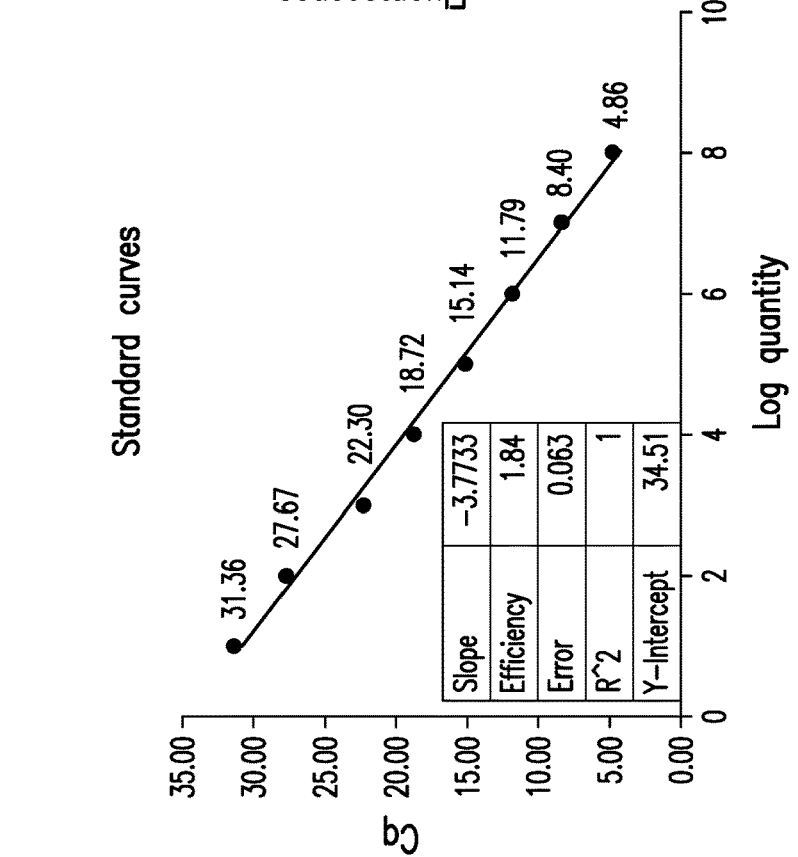
Figure 4F:
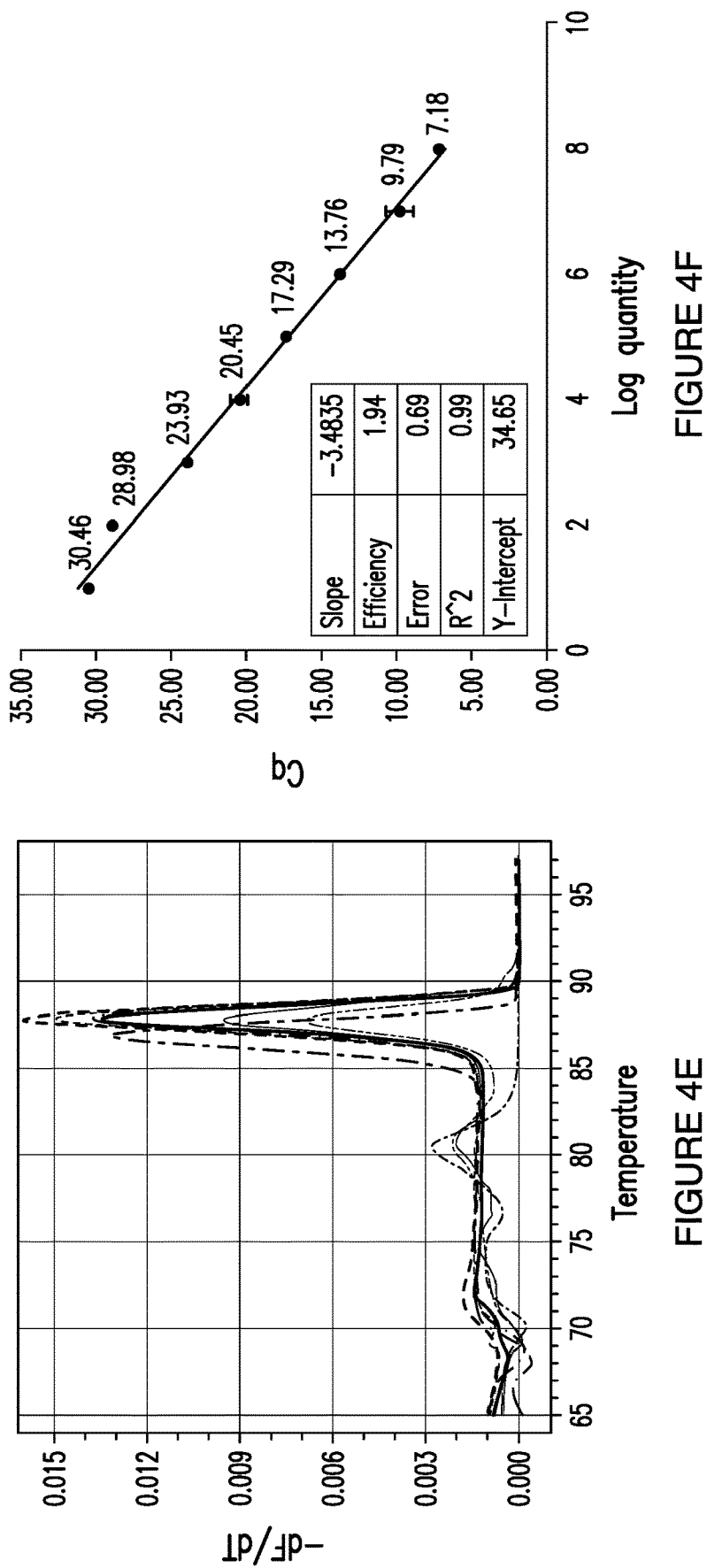
Figure 4E:
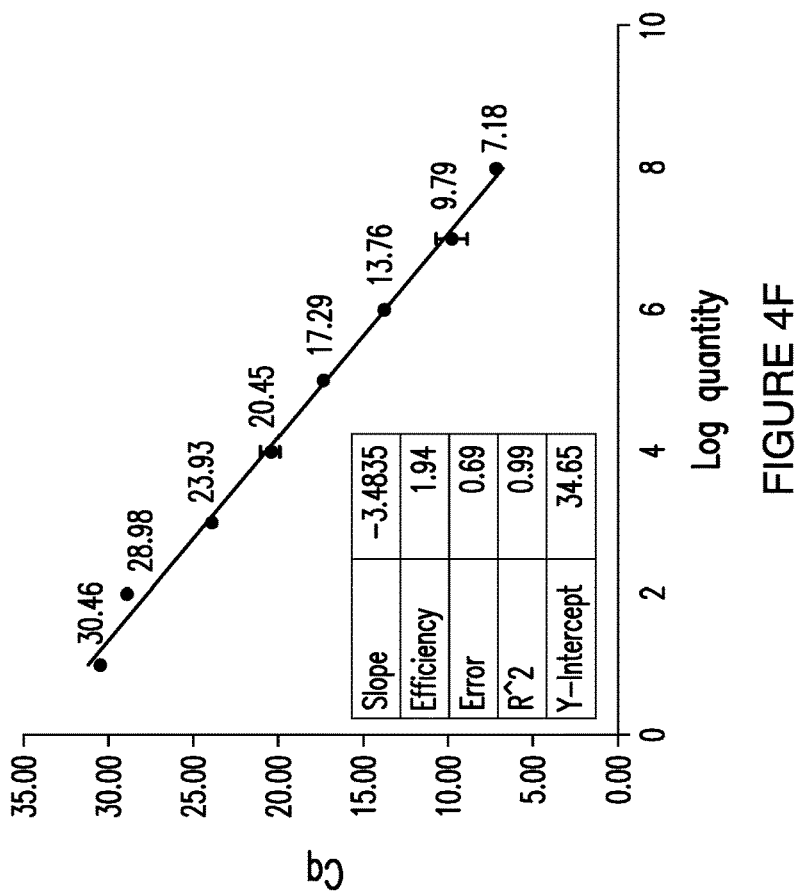
Figures 5A, 5B:
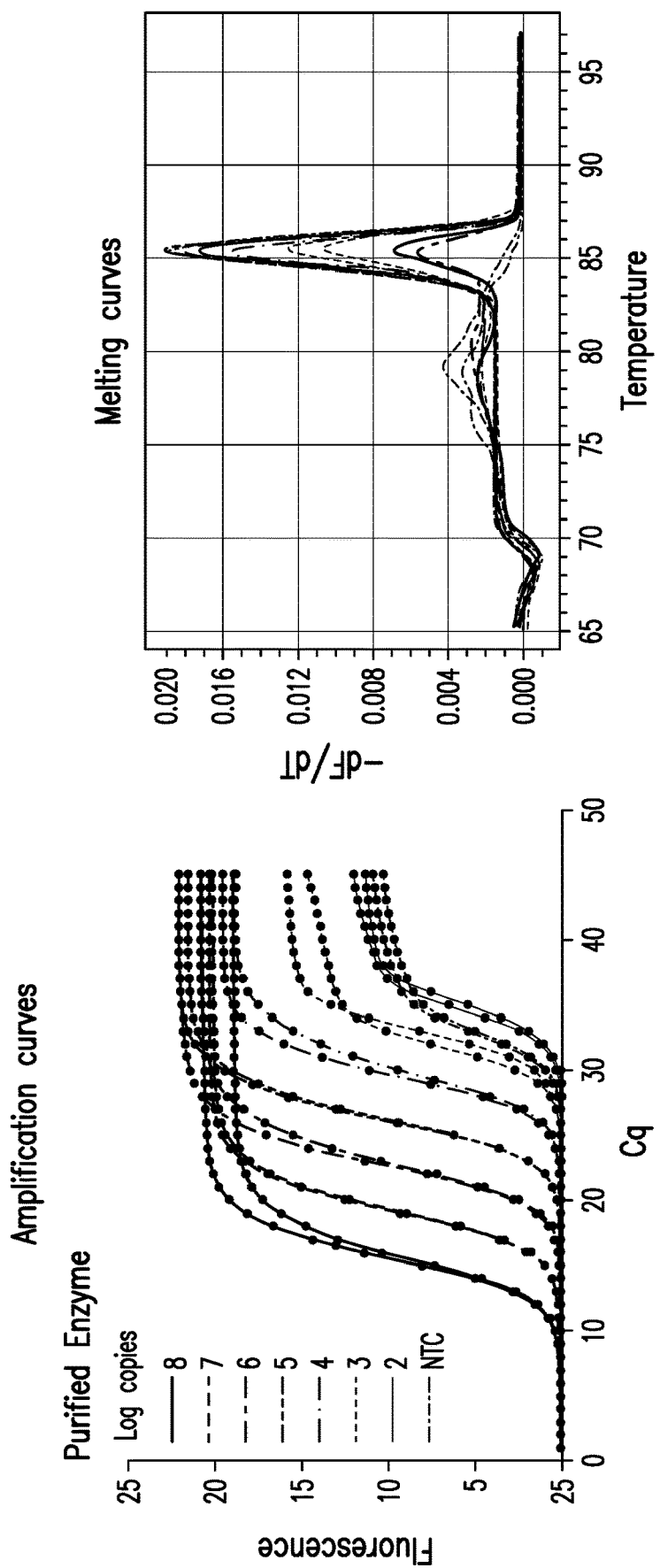
FIG. 5A-F shows EvaGreen qRT-PCR analysis using RTX Exo-DNA polymerase expressing cellular reagents. Indicated copies of synthetic Zika virus derived RNA template were amplified by RT-PCR using 80 ng of pure RTX Exo-DNA polymerase (panels a, b, and c) or $2\times10^6$ cells of RTX Exo-cellular reagents (panels d, e, and f). Amplicon accumulation was assessed in real time by measuring increase in EvaGreen fluorescence. Representative amplification curves using $10^8$, $10^7$, $10^6$, $10^5$, $10^4$, $10^3$, $10^2$, 10 and 0 template RNA copies are shown in panels a and d. These curves were generated using the "Abs quant" analysis protocol in the LightCycler 96 software. 'NTC' refers to no template control. The corresponding amplicon melting temperature analyses performed using the "Tm calling" protocol in the LightCycler 96 software are shown in panels b and e. The melting temperature of non-specific amplicons generated in the absence of templates is distinct from target-derived amplicons. Standard curve analyses performed using the "Abs quant" protocol in the LightCycler 96 software are depicted in panels c and f. Standard curve analyses data for comparing amplification efficiency, linearity, and error are tabulated as insets.
Figure 5C:
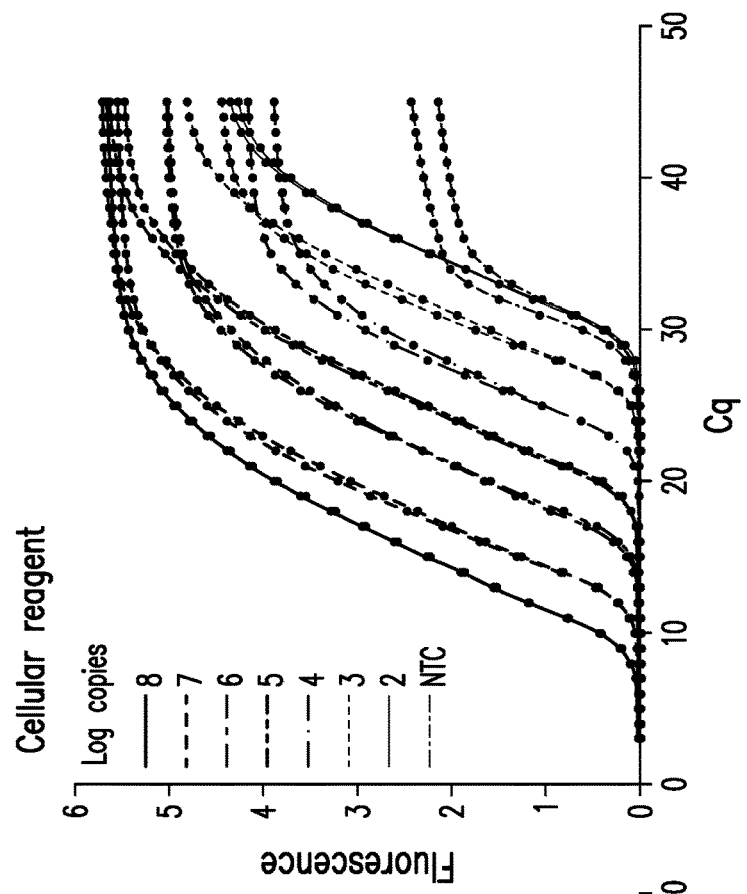
Figure 5D:
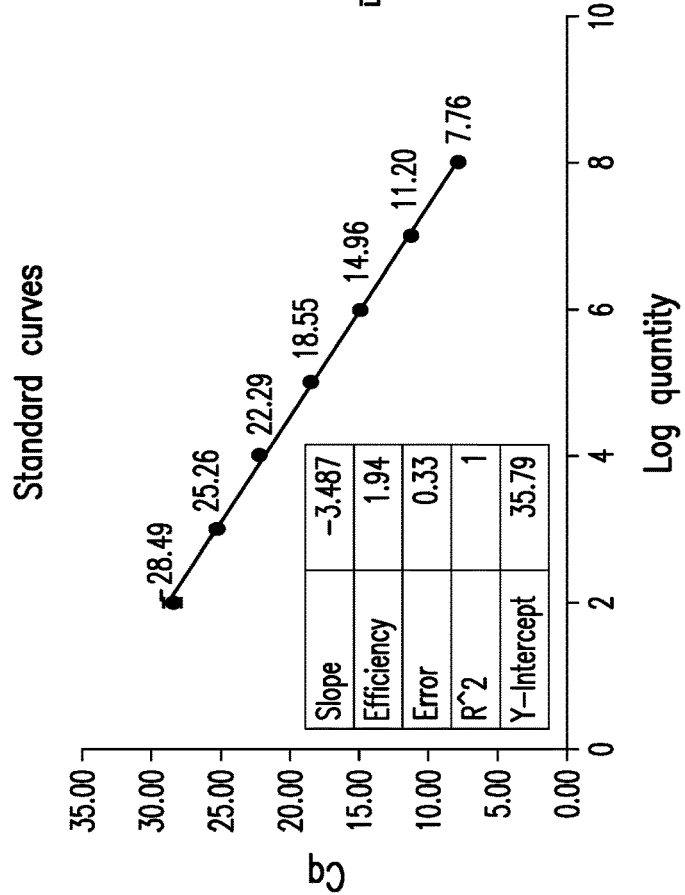
Figures 5E, 5F:
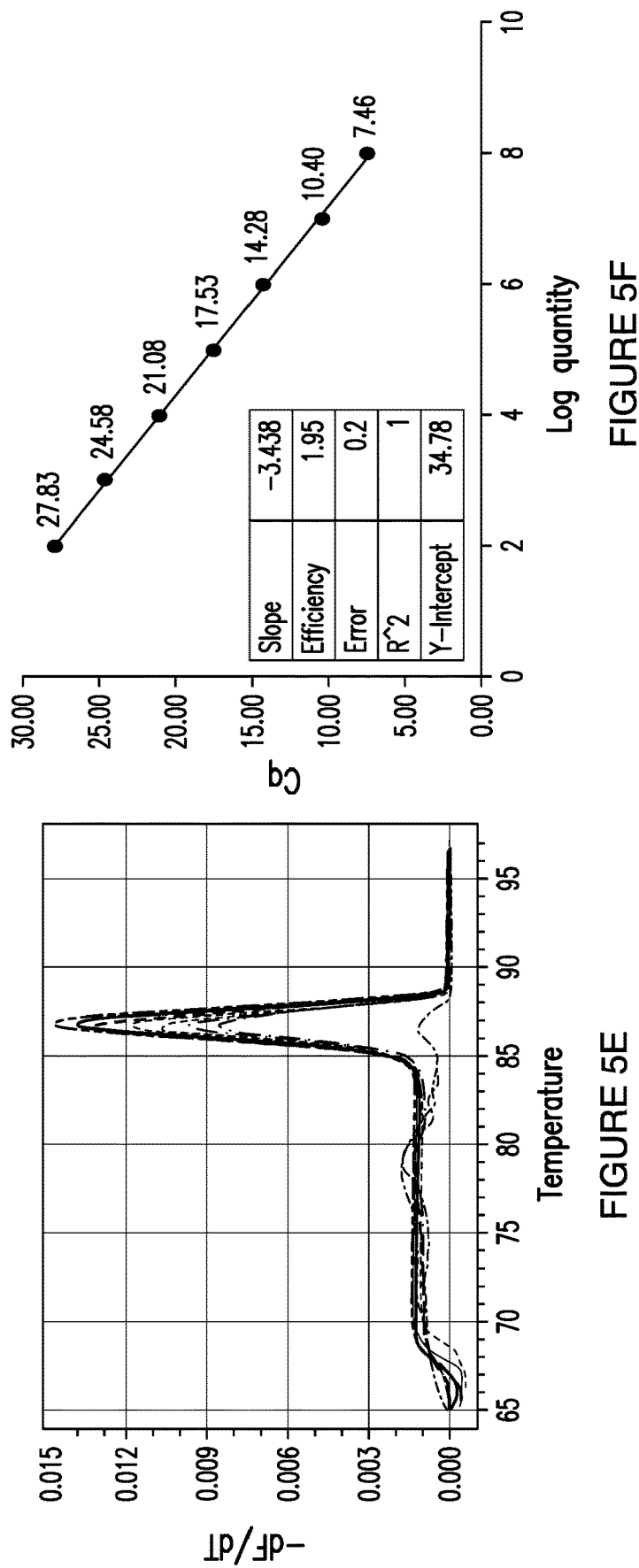

Single enzyme cellular reagents clearly were able to be used as molecular diagnostics, raising the possibility that multiple enzymes that worked in parallel could be delivered via cells. A TaqMan qPCR assay starting with RNA templates and cellular reagents was set up. RNA templates were first reverse transcribed into complementary DNA (cDNA) using MMLV reverse transcriptase-expressing lyophilized bacteria, and then without further purification TaqMan qPCR was carried out using Taq DNA polymerase cellular reagents. The two-step cellular reagent protocol could unambiguously detect templates bearing portions of the Zika virus with $C_q$ values that correlated closely with the expected 10-fold differences between various samples (FIG. 2). RNA samples that were not subjected to reverse transcription also yielded detectable $C_q$ values but these were 6.5 to 7.5 units higher than the $C_q$ values obtained with the cDNA samples, as was expected in the absence of any explicit DNase treatment. Non-specific signal in the absence of templates was not observed.

Finally, since many diagnostic protocols use DNA intercalating fluorophores for measuring amplicon accumulation we developed EvaGreen qPCR mixes containing lyophilized BL21 cellular reagents expressing KlenTaq or RTX Exo-DNA polymerase. In standard curve analyses of *Chlamydia trachomatis* DNA templates, $2 \times 10^7$ cells of KlenTaq polymerase-expressing cellular reagents demonstrated similar amplification efficiencies, Cq values, and detection limits as the standard pure enzyme amount of 0.2 μL per reaction suggested by the manufacturer. Similarly, $2 \times 10^6$ RTX Exo-cellular reagents demonstrated similar amplification efficiencies, $C_q$ values, and detection limits with Zika virus-derived DNA templates, as optimal amount of 80 ng/reaction of the pure enzyme (FIGS. 3, 4). In fact, a one-step qRT-PCR mix built using cellular reagents expressing the RTX thermostable reverse transcriptase could accurately quantify Zika virus-derived RNA templates in a one-pot reaction (FIG. 5). Despite the fact that a TaqMan probe was not involved, negligible non-specific signal was observed with either of these approaches. Moreover, target-derived amplicons could be readily identified by their characteristic melting temperatures. The slight increase in amplicon melting temperature observed in reactions containing cellular reagents can be due to an accompanying increase in ionic concentration and molecular crowding (Harve 2010; Markarian 2012).

ii. Isothermal Nucleic Acid Amplification Using Cellular Reagents

Figure 6A:
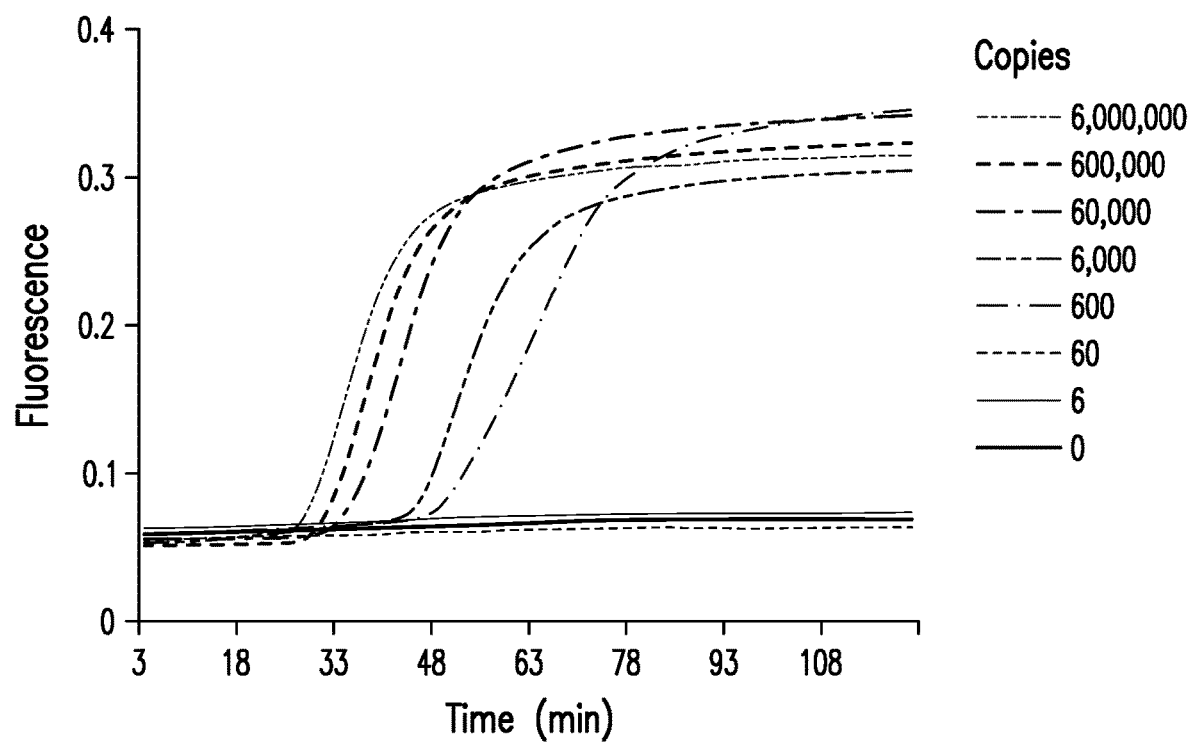
FIG. 6A-D shows isothermal nucleic acid amplification using Bst DNA polymerase cellular reagents. Indicated copies of synthetic DNA templates derived from human glyceraldehyde 3-phosphate dehydrogenase gene were amplified in LAMP-OSD reactions using 16 units of pure Bst-LF (panel a), 16 units of pure Bst 2.0 (panel b), or $2\times10^7$ cells of Bst-LF cellular reagents (panel c). Amplicon accumulation was assessed in real time by measuring increase in OSD fluorescence. Cq values obtained using pure commercial Bst-LF (panel a), pure commercial Bst 2.0 (panel b), and Bst-LF cellular reagent (CR) (panel c) are tabulated. Unlike PCR, LAMP is a complex continuous amplification process in which Cq does not always correlate linearly with template copies (panel d).
Figure 6B:
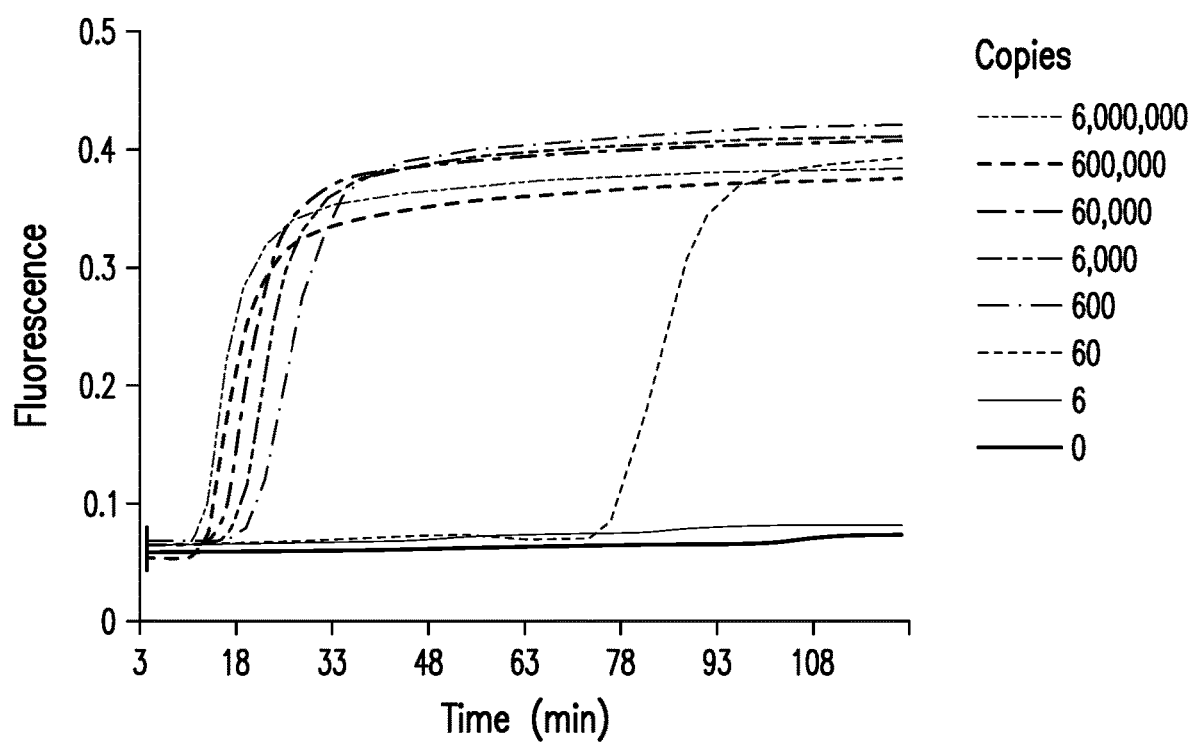
Figures 6C, 6D:
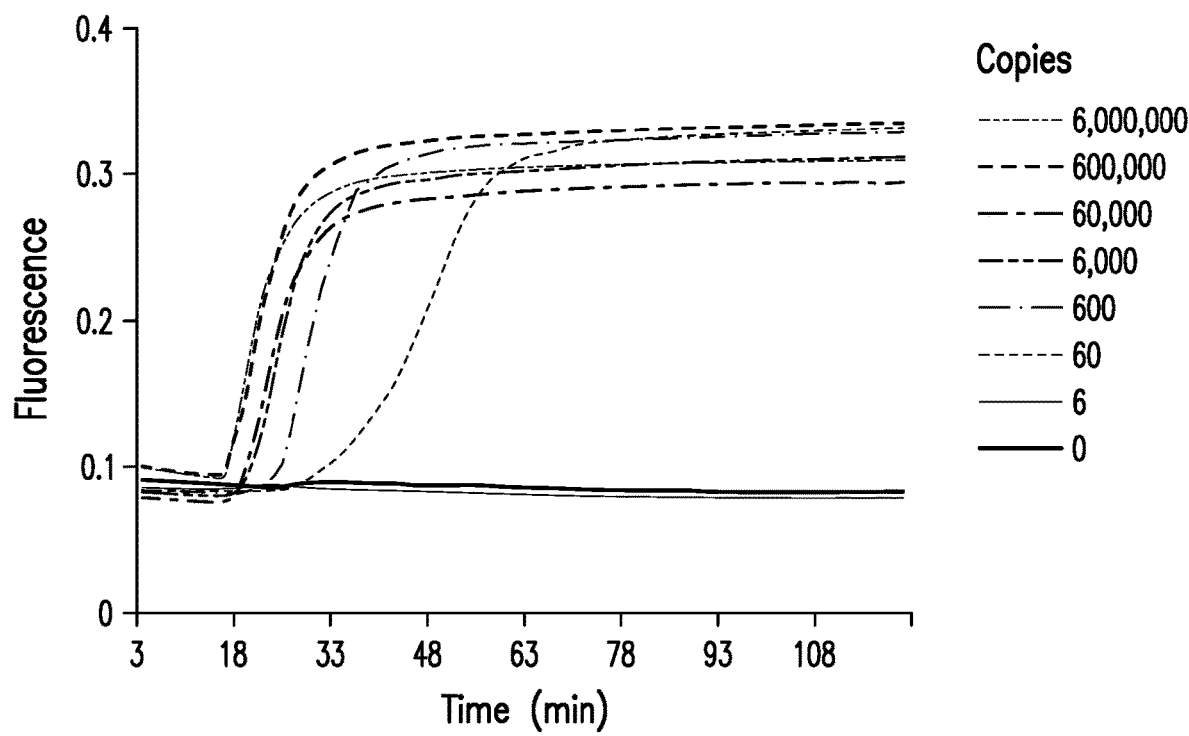
Figure 16:
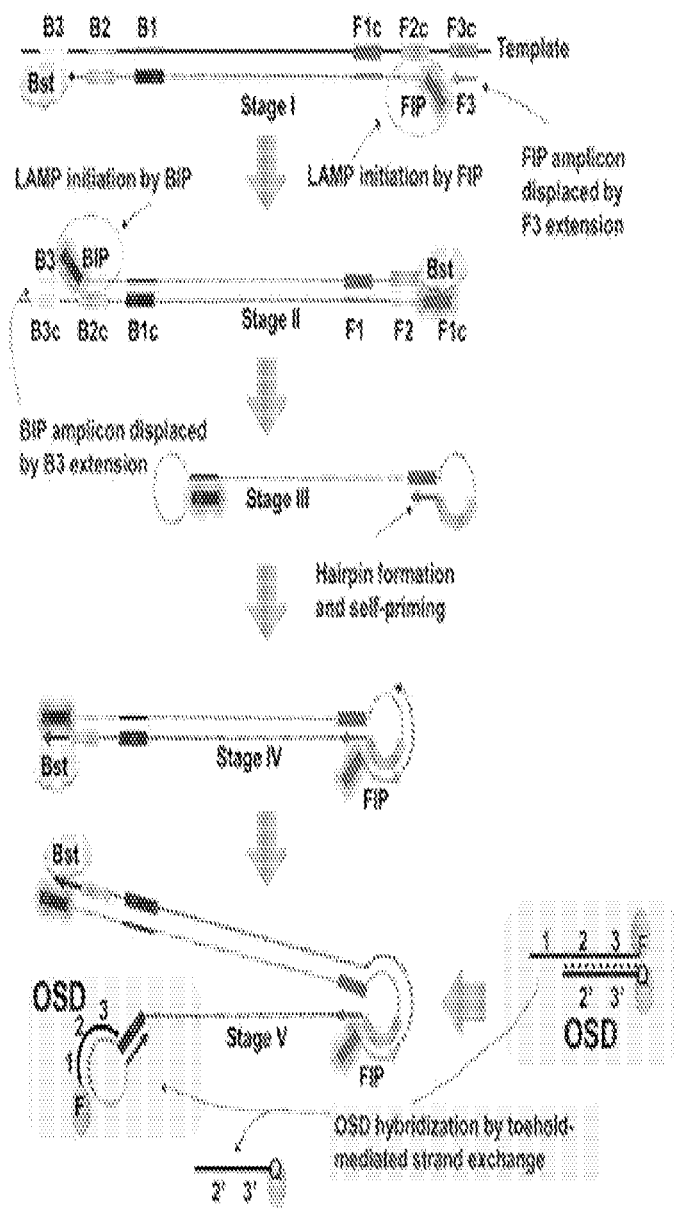
FIG. 16 shows a LAMP-OSD schematic. LAMP uses 2 inner (FIP and BIP) and 2 outer (F3 and B3) primers specific to 6 blocks of target sequences designated as B3, B2, B1, F1c, F2c and F3c. F2 sequence in FIP (F1c-F2) initiates amplification by Bst DNA polymerase (Stage I). F1c sequence in FIP self-primes subsequent amplification. Similarly, BIP (B1c-B2) initiates DNA synthesis by binding to B2c. F3 and B3 primer-initiated DNA synthesis displaces preceding inner primer-initiated strands, which serve as templates for primer-initiated strand displacement DNA synthesis (Stage II). 3'-ends of the resulting single-stranded, dumbbell-shaped amplicons (Stage III) are extended by Bst polymerase to form hairpins (Stage IV). Inner primers hybridize to the single-stranded loops and initiate another round of strand displacement synthesis that opens the original hairpin to form a concatemerized amplicon containing a self-priming 3'-end hairpin (Stage V). The ensuing continuous amplification (initiated both by new inner primers and by self-priming) generates increasingly complex, double-stranded concatameric amplicons containing self-priming hairpins and single-stranded loops to which the OSD probe hybridizes. "c": denotes complementary target sequences. F and Q on the OSD denote fluorophore and quencher, respectively. OSD probe is denoted in terms of numbered domains, each of which represents a short fragment (usually <12 nt) of DNA sequence in an otherwise continuous oligonucleotide strand. Single stranded toeholds are numbered in red. Complementarity between numbered OSD domains is denoted by a single prime symbol.
Figure 17A:
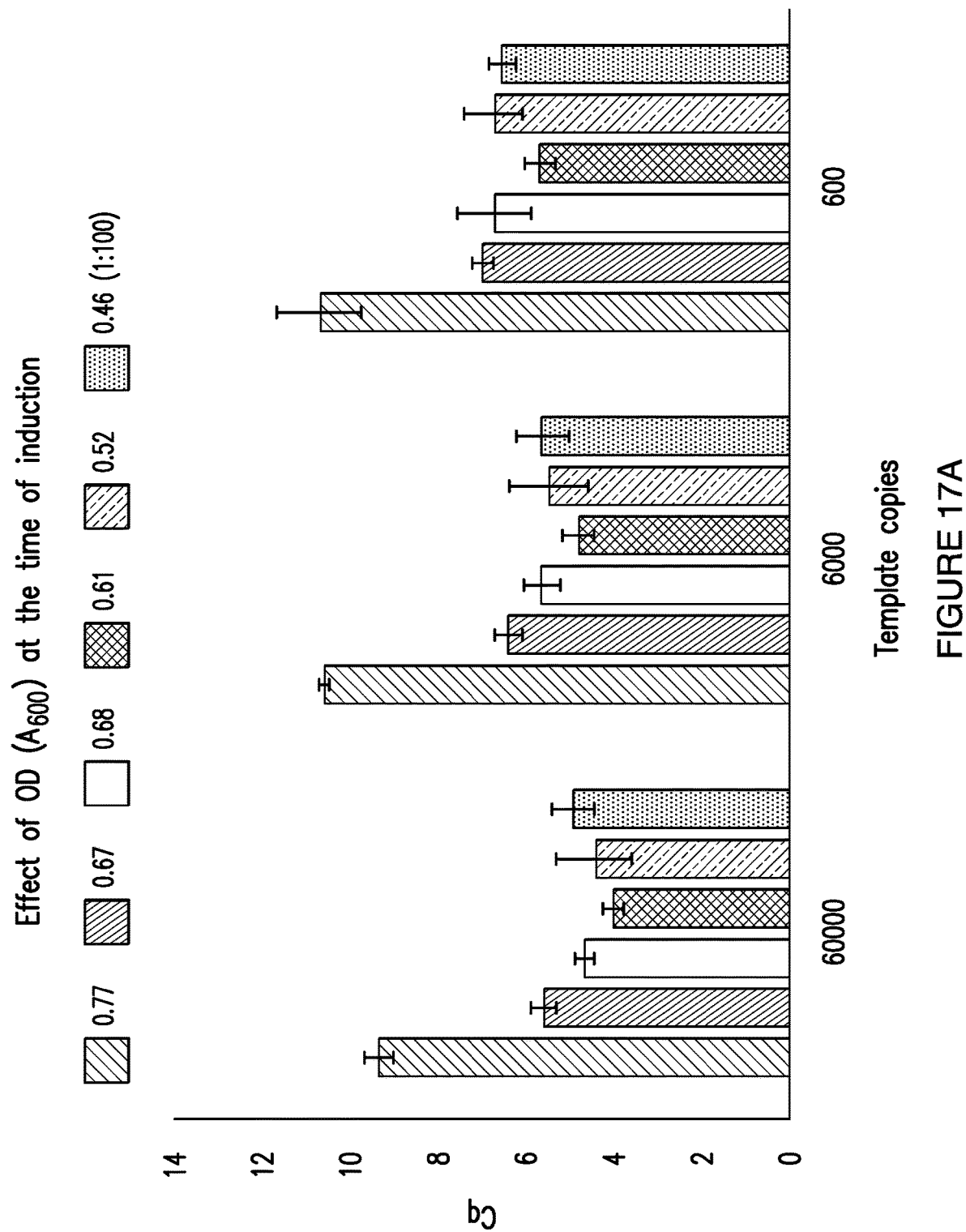
FIG. 17A-B shows the effect of culture conditions on performance of cellular reagents. Amplification efficiencies of lyophilized cellular reagents expressing Bst-LF DNA polymerase were tested in LAMP-OSD assays using indicated template copies. LAMP amplicon accumulation was measured in real-time using fluorogenic OSD probes. Cq values (time-to-signal) at different template copies determined using the "Abs quant" analysis protocol in the LightCycler 96 software are depicted.
Figure 17B:
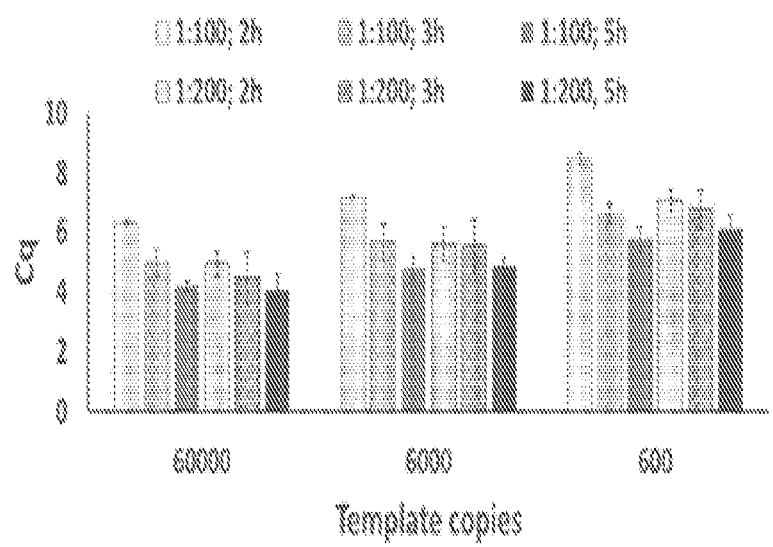
Figure 18:
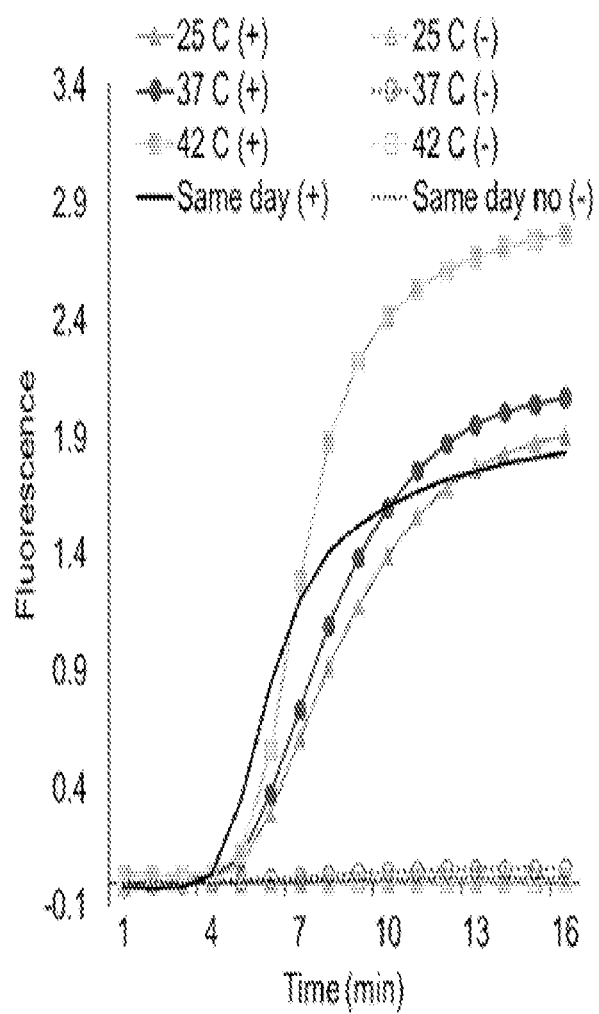
FIG. 18 shows the storage stability of Bst-LF cellular reagents at elevated temperatures. Amplification efficiencies of lyophilized cellular reagents expressing Bst-LF DNA polymerase were tested in LAMP-OSD assays using indicated template copies. LAMP amplicon accumulation was measured in real-time using fluorogenic OSD probes. Amplification curves obtained with either 60,000 (full traces labeled "(+)") or 0 (dashed traces labeled "(−)") copies of gapd templates are depicted. Amplification curves were generated using the "Abs quant" analysis protocol in the LightCycler 96 software. Bst-LF cellular reagents were either tested immediately after lyophilization (black traces labeled "Same day") or after storage with desiccants for 21 days at 25° C. (green traces labeled "25 C"), 37° C. (pink traces labeled "37 C"), or 42° C. (blue traces labeled "42 C").
Figure 19:
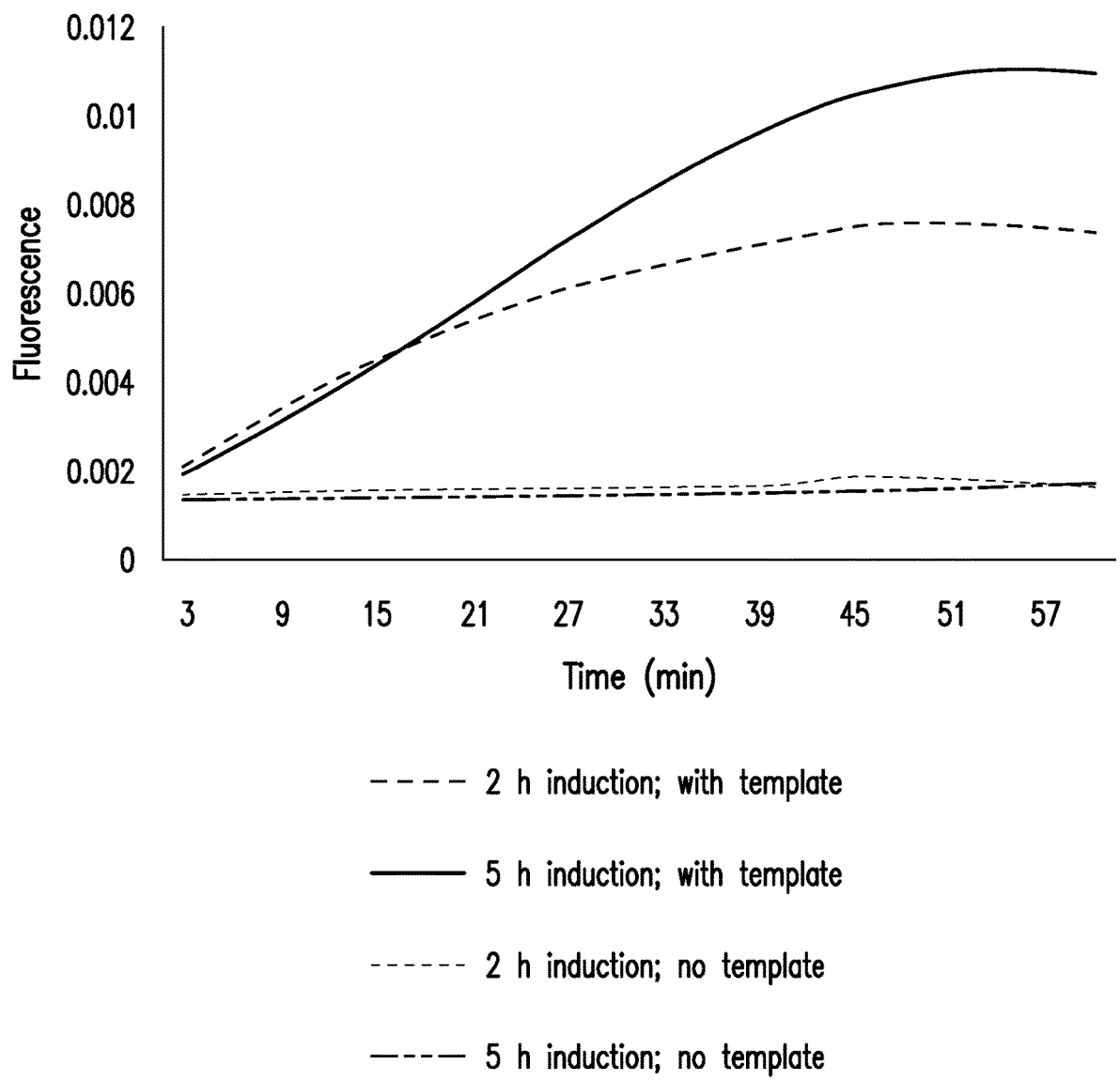
FIG. 19 shows in vitro transcription using lyophilized BL21 bacteria expressing T7 RNA polymerase. Protein production in bacterial reagents was induced for the indicated duration. Accumulation of malachite green aptamer transcripts is depicted as real-time increase in malachite green fluorescence.

Beyond PCR, it should be possible to carry out other reactions using cellular reagents. To demonstrate the general utility of the concept, cellular reagents expressing Bst-LF, the *Bacillus stearothermophilus* strand displacing DNA polymerase (large fragment) commonly used for isothermal nucleic acid amplification reactions were assayed for their ability to carry out LAMP-OSD (FIG. 16). Similar to 16 units of pure commercial Bst 2.0 enzyme, $2 \times 10^7$ Bst-LF cellular reagents could amplify as few as 60 copies of human glyceraldehyde-3-phosphate dehydrogenase gene target, within 60 min (FIG. 6). Although, Bst 2.0 is an in silico designed polymerase engineered for greater amplification speed and yield than Bst-LF (NEB), $2 \times 10^7$ cellular Bst-LF reagents were only ~2 Cq slower than 16 units of commercial Bst 2.0. This level of performance by Bst-LF cellular reagents is especially impressive considering the fact that most users typically apply only 8 units of Bst 2.0 per reaction to reduce reaction cost (Tomita 2008). As long as a sufficient number of bacteria were added, the production process for the creation of lyophilized cellular reagents was robust to perturbations such as bacterial sub-culture initiation density, optical density at logarithm phase induction of protein expression, alteration of expression platform, and induction duration (FIG. 17). Furthermore, similar to Taq DNA polymerase, Bst DNA polymerase cellular reagents were stable for at least 3 weeks when stored at temperatures as high as 42° C. (FIG. 18).

iii. Cellular Reagents for Molecular and Synthetic Biology

Given that cellular reagents were robust in various amplification reactions and formats, it was next determined to what extent they could be used in other contexts. Molecular and synthetic biology techniques are currently heavily reliant on the activity of pure enzymes. To demonstrate the possibilities for facile, multi-enzyme cloning procedures with cellular reagents, a set of cells were created that would contain either enzymes or templates as input for one of the most commonly used methods for cloning, Gibson assembly of DNA fragments (Gibson 2009). Gibson assembly can be used to create vectors from two or more DNA fragments in a one-pot reaction by relying on complementary overlaps created by T5 exonuclease degradation. Once complementary strands have come together, DNA polymerase is used to fill gaps, and Taq DNA ligase seals the remaining nicks to create the new vector.

When DNA parts were mixed with treated cellular reagents comprising $2 \times 10^7$ Taq DNA ligase cells, $10^6$ Taq DNA polymerase cells, and $10^5$ T5 exonuclease cells (Table 2) the Gibson cloning procedure was successful, producing 48-60% of the number of colonies observed with a commercial enzyme master mix containing 0.08 units of T5 exonuclease, 0.5 units of Phusion DNA polymerase, and 80 units of Taq DNA ligase. Background assembly was similar for both cellular and commercial reagents.

Cellular Gibson assembly is a highly enabling technology that stands to significantly reduce costs for and increase accessibility to a core tool for synthetic biology. To further bolster the appeal and utility of cellular Gibson assembly it was sought to combine amplification and assembly with cellular reagents. As a first step, cellular Phusion reagents were used to amplify linear vector and insert fragments directly from two different bacterial strains (FIG. 7). The kanamycin resistance cassette from the donor plasmid pJLsfGFP and the entire vector backbone of ampicillin-resistant pATetO 6xHis plasmid were amplified with the inclusion of 30 bp overlaps. Following agarose gel purification of the DNAs produced by amplification with cellular reagents, Gibson assembly with either cellular or purified reagents yielded 61 and 884 clones, respectively, that were jointly resistant to both ampicillin and kanamycin; all were verified by sequencing to be correctly assembled (FIG. 7). A three-part assembly was attempted with DNAs amplified by cellular reagents by dividing pUC19 into two linear fragments with 30 bp overlaps prior to purification and assembly. The three part assembly yielded 28 clones, all of which were correctly assembled (FIG. 7). The improvement in the fraction of correctly assembled vectors in this example (100%) is likely due to the fact that correctly assembled vectors can be directly selected via antibiotic resistance.

Finally, the same assemblies were carried out without DNA purification, using only cellular Gibson reagents. Eight and two colonies, respectively, were obtained, all of which proved to be the correct assembly (FIG. 7).

4) Discussion

Compared to current technologies for the production and distribution of purified protein reagents, cellular reagents present several advantages. These include: (i) lower production time and cost due to the elimination of protein purification; (ii) simplified quality control during production in which optimized culture density (measured as A600) is a convenient metric for ensuring uniformity of performance; (iii) favorable yield for many small to medium scale applications (1 ml culture=150 qPCR or isothermal amplification reactions); (iv) cheaper storage and transport without a cold chain; (v) seamless integration of cellular reagents into many different molecular biology technologies due to easy access to the enzyme payload without additional bacterial lysis steps; and (vi) negligible declines in assay performance or outcomes when using cellular reagents. Overall, these advantages make cellular reagents significantly cheaper to produce, store, distribute, and use. Furthermore, since the cellular reagent production process involves considerably fewer procedures and equipment it should be easier to adopt by scientists, clinicians, or companies in a small region. It is also conceivable that the aforementioned advantages in cost and process frugality offered by cellular reagents could provide benefits for niche applications such as research at remote terrestrial or extraterrestrial stations (Parra 2017) where transport of elaborate purification equipment or liquid reagents can be difficult and expensive.

There has recently been a surge of interest in 'in vitro biology' (Liu 2008; Hodgman 2012; Hunt 2017), with in vitro transcription and translation (IVTT) reactions being used for diagnostic applications (Pardee 2016) and for the production of many new proteins (Jewett 2008; Gan 2014; Chong 2014). Simplification of the traditionally labor and cost intensive procedures for preparation and storage of *E. coli* IVTT extracts is key to wider and newer applications (Kwon 2015). For instance, lyophilization of lysed *E. coli* extracts has allowed high-density storage and improved shelf-life (Smith 2014). IVTT procedures can be further simplified by eliminating lysis and basal purification. The interest in in vitro biology overlaps significantly with the continuing adoption of synthetic biology methods for both research and education (Si 2016; Kelwick 2015), and the demonstration that cellular reagents can be used for Gibson assembly points the way to a new paradigm for making constructs in which a variety of 'cellular templates' can be distributed along with cellular reagents to create entirely new constructs. The cellular reagent platform can be expanded to offer additional enzymatic activities as well as alternate cellular environments such as those offered by eukaryotes like *Pichia pastoris* and *Saccharomyces cerevisiae* (Mattanovich 2012).

Figure 20:
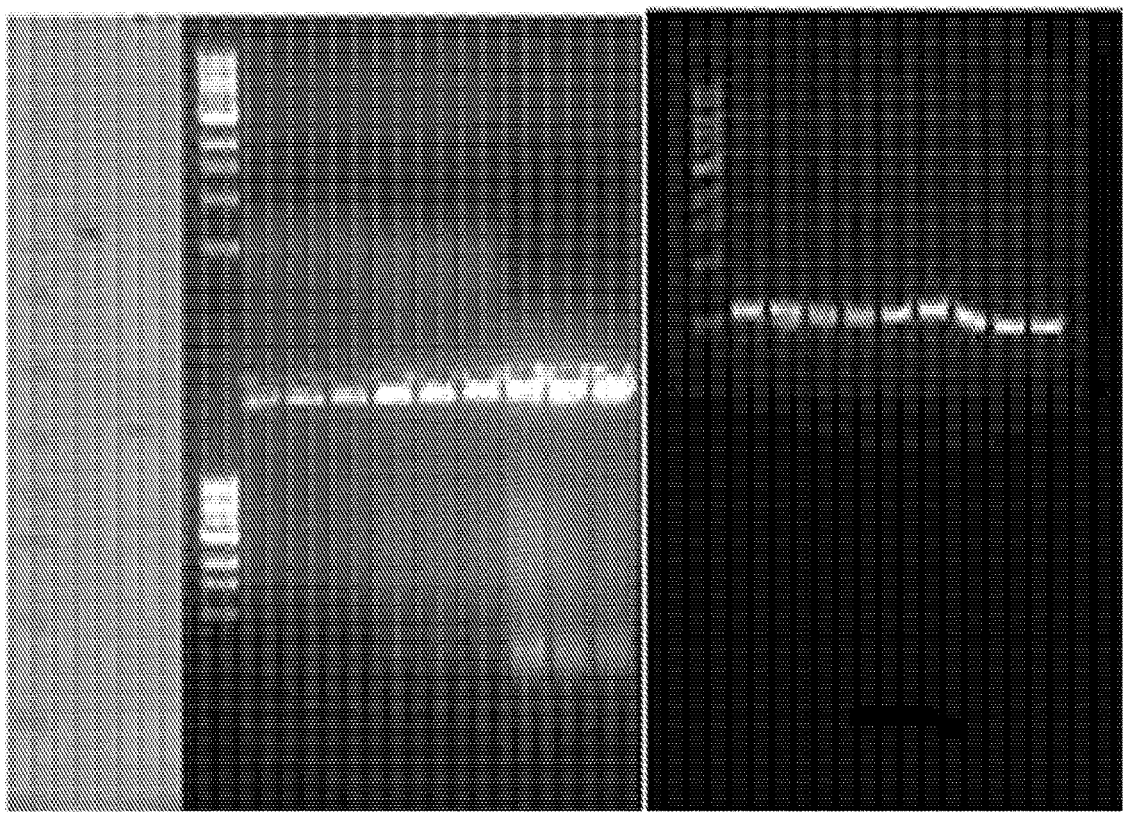
FIG. 20 shows a change in expression and activity in pET vector. Left, 25 mL cultures of KOD were induced for 4 hours and purified by Ni-NTA chromatography. Lane 1 is a protein standard. Lane 2 shows production in pET28. Lane 3 is the pAK vector. No visible amount of polymerase could be seen when induced from pAK. Middle, varying amounts of cells (0.5-20 μL) were used in a 30 μL reaction using the original pAK selection vector for expression. Amplicons could not be seen in any of the lanes. Right, 1 μL of induced cells harboring the pET vector (biological replicates).
Figure 21:
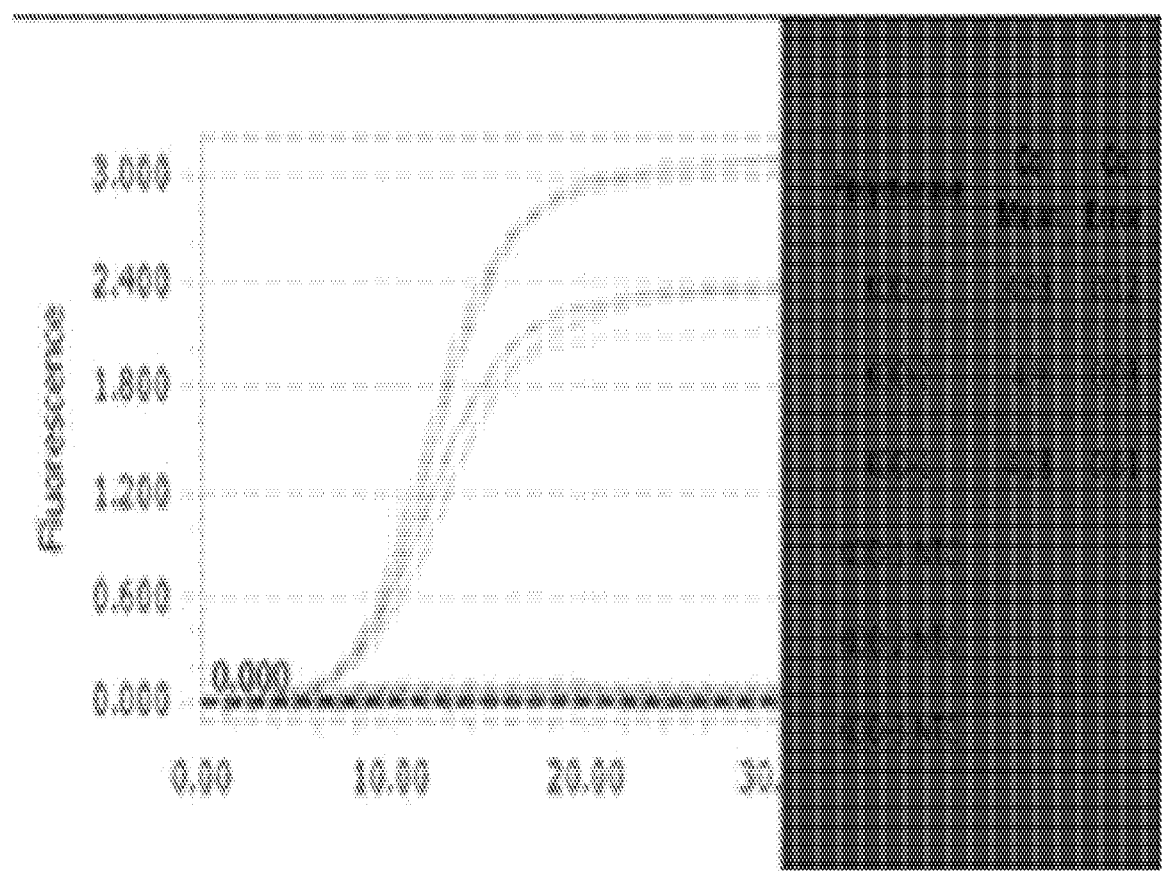
FIG. 21 shows qPCR-based screen proof-of-concept. 1 μL of induced cells harboring the polymerase in a pET vector was used to detect 2.5 ng of an exogenous plasmid (pUC19). Three independent clones were tested in triplicate (9 total). Cq values were all within error.

Example 2: Development of Screening Technologies for Engineered DNA Polymerase Selection Procedures It was found that it took up to two weeks before a particular polymerase variant could be assayed after the selection was completed. The variant needed to be isolated and cloned into a suitable expression vector and then sequenced before purifying the enzyme using standard methods. The original pAK vector used for CSR selections did not produce enough polymerase for bulk assays using manageable volumes of culture (Ghadessy and Holliger, 2007). In fact, it required at least 500 mL of culture to produce enough enzyme to properly purify. For example, 25 mL of culture was not enough to reliably purify using NiNTA resin. However, once a variant was moved into a T7-based pET vector, 25 mL of culture was more than enough to purify usable quantities of polymerase (FIG. 20). While this greatly reduced the cost and time of assaying a variant, this methodology was still slow. Fortunately, once a variant was cloned into the expression vector, it was found that 0.5 µL of induced cells was enough to use in a typical PCR reaction (FIG. 20). Further, cells could be stored as pellets at −20° C. or −80° C. before resuspension and testing. This allowed for the growth of sub-milliliter quantities of cells in 96-well grow blocks. Further, cells could be screened in bulk using qPCR (FIG. 21). This would allow for screening of up to 96 variants at once without having to run gels. Rounds could also be assayed within a day, rather than 6-8 variants over the course of two weeks.

Small Scale Purification for Screening

Overnight cultures of BL21 DE3 harboring polymerase variants in a pET21-derived expression vector were diluted 1:20 into 25 mL of 2XYT growth medium. Cells were grown for an additional 2 hours before inducing expression with 1 mM IPTG for 4 hours. Cells were then collected by centrifugation, washed in TBS, and resuspended in 2 mL of B-PER II cell lysis buffer (Thermo). The cells were then incubated at 80° C. for 20 minutes on a thermal block with light agitation. Debris was cleared by centrifugation (20,000×g) for 15 minutes. Lysate was then incubated with 25 uL NiNTA resin and step eluted with imidazole. Purified protein was dialyzed into 50 mM Tris-HCl, 50 mM KCl, 0.1% Tween20, pH 8.0.

Whole-Cell PCR and qPCR Screening

Overnight cultures of BL21 DE3 harboring polymerase variants in a pET21-derived expression vector were diluted 1:20 into 500 µL or 4 mL of superior growth medium. Cells were grown for an additional 2 hours before inducing expression with IPTG (1 mM) for 4 hours. Cells were then collected by centrifugation, washed in TBS, and resuspended in 1×PCR buffer (Accuprime). Next, 0.5-10 µL cells were incubated with primers specific to a 550 bp piece of the pET21 vector. For qPCR screening, pUC19 was added to the master mix, and EvaGreen intercalating dye was used to monitor fluorescence in standard 30 µL reactions using a LightCycler96.

Lastly, it should be understood that while the present disclosure has been provided in detail with respect to certain illustrative and specific aspects thereof, it should not be considered limited to such, as numerous modifications are possible without departing from the broad spirit and scope of the present disclosure as defined in the appended claims.

Example 3: Freeze-Drying Cellular Reagents on Paper

To demonstrate the feasibility of paper-based format of cellular reagents, $2 \times 10^7$ BL21 *E. coli* cells, induced to express Bst-LF or Taq DNA polymerase for 3 h, were resuspended in 1×PBS buffer and dotted on a 2 mm×3 mm piece of glass fiber paper (MDI Membrane Technologies, India). The paper pieces saturated with cellular reagents were then individually placed inside 0.2 ml tubes and subjected to lyophilization for 3 h. Subsequently, these paper-based reagents were stored at room temperature in the presence of desiccants until use.

Figure 22:
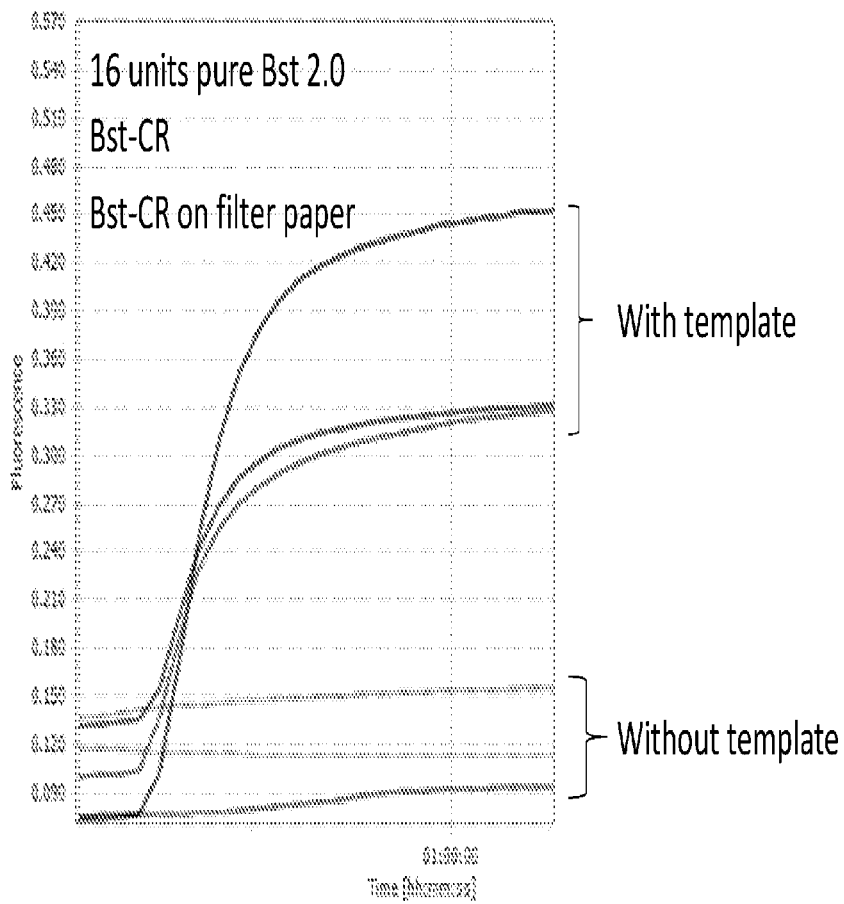
FIG. 22 shows human gapd gene sequences were amplified by LAMP-OSD using 16 units of pure Bst 2.0 DNA polymerase from New England Biolabs (black trace). In duplicate reactions, amplification was performed using rehydrated Bst-LF cellular reagents prepared by either freeze drying cellular reagents in bulk directly in tubes (Bst-CR; red trace) or in individual reaction aliquots on small pieces of glass fiber filter papers that were subsequently added directly to reactions (Bst-CR on filter paper; blue trace).
Figure 23:
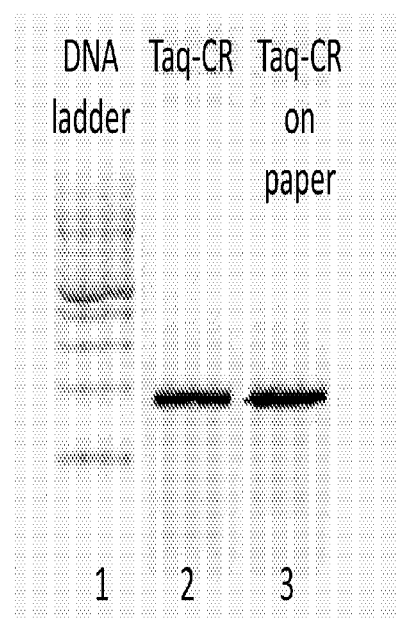
FIG. 23 shows an exemplary insert sequence amplified from pcr2.1-TOPO plasmid using rehydrated Taq DNA polymerase cellular reagents (Taq-CR; lane 2) that had been freeze-dried in bulk in tubes. In a duplicate reaction, amplification was performed using Taq DNA polymerase cellular reagents that were freeze-dried in individual reaction aliquots on small pieces of glass fiber filter papers that were subsequently added directly to the PCR reaction (Taq-CR on filter paper; lane 3).

Enzyme activity in these paper-based cellular reagents was assessed using standard LAMP-OSD assay (for Bst-LF) or PCR assay (Taq DNA polymerase) for the paper-free powder-form of cellular reagents. (FIGS. 22 and 23). The procedure was modified by eliminating the step of cellular reagent rehydration and portioning into individual reactions. Instead, single 2 mm by 3 mm pieces of freeze-dried cellular reagent paper was directly dropped into a 50 µl PCR or 25 µl LAMP-OSD reaction. The LAMP-OSD reactions were then incubated on a LightCycler 96 PCR machine held at 65° C. where amplicon generation was measured as accumulation of FAM-labeled OSD fluorescence. The PCR reactions containing paper-cellular reagents were cycled through 98° C. for 30 sec, followed by 20 cycles of 10 sec at 98° C., 15 sec at 55° C., and 30 sec at 72° C. Subsequently, 5 ul of the PCR reactions were separated using agarose gel electrophoresis and amplicons were visualized using ethidium bromide staining.

Tables

TABLE 1

Oligonucleotide and template sequences used in Example 1

| Name | Sequence | Use |
|---|---|---|
| CT-F | TAGTGGCGGAAGGGTTAG (SEQ ID NO: 1) | *Chlamydia trachomatis* qPCR |
| CT-R | CGTCATAGCCTTGGTAGG (SEQ ID NO: 2) | |
| *Chlamydia trachomatis* template | CGCCAAGCTTGGTACCGAGCTCGGATCCACTAGTAACGGCC GCCAGTGTGCTGGAATTCTAATACGACTCACTATAGGGCAAT TGTTTAGTGGCGGAAGGGTTAGTAATGCATAGATAATTTGTC CTTAACTTGGGAATAACGGTTGGAAACGGCCGCTAATACCG AATGTGGCGATATTTGGGCATCCGAGTAACGTTAAAGAAGG GGATCTTAGGACCTTTCGGTTAAGGGAGAGTCTATGTGATAT CAGCTAGTTGGTGGGTAAAGGCCTACCAAGGCTATGACGT CTAGGCGGATTGAGAGATTGGCCGCCAACACTGGGACTGAG | |

TABLE 1-continued

Oligonucleotide and template sequences used in Example 1

| Name | Sequence | Use |
|---|---|---|
| | ACACTGCCCAGACTCCTACGGGAGGCTGCAGTCGAGAATCTT TCGCAATGGACGGAAGTCTGACGAAGCGACGCCGCGTGTGT GATGAAGGCTCTAGGGTTGTAAAGGAATTCTGCAGATATCC ATCACACTGGCGGCCGCTCGAGCATGCATCTAGAGGGCCCA ATT (SEQ ID NO: 3) | |
| Zika-255-F | GGTAGATCCATTGTGGTCCCTTGCC (SEQ ID NO: 4) | Zika |
| Zika-256-R | CCACACCATGAGCATGTCCTCAGTAGTC (SEQ ID NO: 5) | Evagreen |
| Zika virus template | CTAGTAACGGCCGCCAGTGTGCTGGAATTCGGTAGATCCATT GTGGTCCCTTGCCGCCACCAAGATGAATTGATTGGCCGAGCC CGTGTATCACCAGGGGCAGGATGGAGCATTCGGGAGACTGC CTGTCTAGCAAAATCATATGCACAGATGTGGCAGCTTCTTTA CTTCCACAGAAGAGACCTTCGACTGATGGCCAATGCTATTTG TTCGGCTGTGCCAGTTGACTGGGTACCAACCGGGAGAACCA CCTGGTCAATCCACGGAAAGGGAGAATGGATGACTACTGAG GACATGCTCATGGTGTGGAATAGAGTGTGGATTGAGGAGGA ATTCTGCAGATATCCATCACACTGGCGGCCGCTCGAGC (SEQ ID NO: 6) | q(RT)PCR |
| gapdLAMP.F3 | GCCACCCAGAAGACTGTG (SEQ ID NO: 7) | gapd |
| gapdLAMP.B3 | TGGCAGGTTTTTCTAGACGG (SEQ ID NO: 8) | LAMP-OSD |
| gapdLAMP.FIP | CGCCAGTAGAGGCAGGGATGAGGGAAACTGTGGCGTGAT (SEQ ID NO: 9) | |
| gapdLAMP.BIP | GGTCATCCCTGAGCTGAACGGTCAGGTCCACCACTGACAC (SEQ ID NO: 10) | |
| gapdLAMP.LR | TGTTCTGGAGAGCCCCGCGGCC (SEQ ID NO: 11) | |
| gapdOSD.F | /56-FAM/ CTCACTGGCATGGCCTTCCGTGTCCCCACTGCCAAC/3In vdT/ (SEQ ID NO: 12) | |
| gapdOSD.Q | GGACACGGAAGGCCATGCCAGTGAG/3IABkFQ/ (SEQ ID NO: 13) | |
| gapd template | CTAGTAACGGCCGCCAGTGTGCTGGAATTCCCACAGTCCATG CCATCACTGCCACCCAGAAGACTGTGGATGGCCCCTCCGGG AAACTGTGGCGTGATGGCCGCGGGGCTCTCCAGAACATCAT CCCTGCCTCTACTGGCGCTGCCAAGGCTGTGGGCAAGGTCAT CCCTGAGCTGAACGGGAAGCTCACTGGCATGGCCTTCCGTGT CCCCACTGCCAACGTGTCAGTGGTGGACCTGACCTGCCGTCT AGAAAAACCTGCCAAATATGATGACATCAAGAAGGTGGTGA AGCAGGCGTCGGAGGGCCCCCTCAAGGGCATCCTGGGCTAC ACTGAGCACCAGGTGGTCTCCTCTGACTTCAACAGCGACACC CACTCCTCCACCTTTGACGCTGGGGCTGGCATTGCCCTCAAC GACCACTTTGTCAAGCTCATTTCCTGGAATTCTGCAGATATC CATCACACTGGCGGCCGCTCGAGC (SEQ ID NO: 14) | |
| Zika 4481_F | CTGTGGCATGAACCCAATAG (SEQ ID NO: 15) | Zika |
| Zika 4552c | ATCCCATAGAGCACCACTCC (SEQ ID NO: 16) | TaqMan |
| Zika 4507c-FAM | /56-FAM/CCACGCTCCAGCTGCAAAGG/3IABkFQ/ (SEQ ID NO: 17) | q(RT)PCR |
| Zika TaqMan template | GGGAC CATCTGTGGCATGAACCCAA TAGCCCATACC CTTTGCAGCT GGAGCGTGGT ACGTGTATGT GAAGACTGGAAAAAGGAGTG GTGCTCTATG GGATGTGCCT (SEQ ID NO: 18) | |
| SB.pATetO.R | GCG CCC TTC GAT GTG ATG GTG ATG GTG ATG CGA TCC TCT G (SEQ ID NO: 19) | Cellular PCR |
| SB.pATetO.F | TGATAATTGCCTCTGCCAAAATTCTGTCCTCAAGCGTTTTAGT TCG (SEQ ID NO: 20) | primers for pATetO 6XHis |
| SB.Kan.ptet.F | GATCGCATCACCATCACCATCACATCGAAGGGCGC GCTGAAAGCCAATTCTGATTAGAAAAACTC (SEQ ID NO: 21) | Cellular PCR |
| SB.Kan.ptet.R | GAGGACAGAATTTTGGCAGAGGCAATTATCA GATCCTTTGATCTCACGTTGTGTCTC (SEQ ID NO: 22) | primers for kan[r] insert for pATetO 6XHis |
| SB.puc19FL.F | GAT CCC CGG GTA CCG AGC TCG AAT TCA CTG G (SEQ ID NO: 23) | Cellular PCR |
| SB.puc19.FL.R | CTC TAG AGT CGA CCT GCA GGC ATG CAA GCT TG (SEQ ID NO: 24) | primers for pUC19 |
| SB.puc19sm.R | GAC AGT TAC CAA TGC TTA ATC AGT GAG GCA CC (SEQ ID NO: 25) | fragments 1 and 2 |
| SB.puc19sm.F | GGTGCCTCACTGATTAAGCATTGGTAACTGTC (SEQ ID NO: 26) | |

TABLE 1-continued

Oligonucleotide and template sequences used in Example 1

| Name | Sequence | Use |
|---|---|---|
| SB.Kan.puc19.F | CAAGCTTGCATGCCTGCAGGTCGACTCTAGAGGCTGAAAGC CAATTCTGATTAGAAAAACTC (SEQ ID NO: 27) | Cellular PCR primers for kan$^r$ insert for pUC19 |
| SB.Kan.puc19.R | CCAGTGAATTCGAGCTCGGTACCCGGGGATC GATCCTTTGATCTCACGTTGTGTCTC (SEQ ID NO: 28) | |
| OE.FWD | TAATACGACTCACTATAGGGTGGTTTCTGGGGTGACCGGGTT GATTCTCAGCCCTTCGCA (SEQ ID NO: 29) | Overlap extension assay |
| OE.REV | AGGGGTTGGTTGGATGAATATAGGGGATTGCGAAGGGCTGA GAATCAACCCGGTCACCCC (SEQ ID NO: 30) | |
| pCR2.1.FluB template | CTAGTAACGGCCGCCAGTGTGCTGGAATTCTAATACGACTCA CTATAGGGATGTCGCTGTTTGGAGACACAATTGCCTACTTGC TTTCATTAACAGAAGATGGAGAAGGCAAAGCAGAACTAGCA GAAAAGTTACACTGTTGGTTTGGTGGGAAAGAATTTGACCTA GACTCAGCCTTGGAATGGATAAAAAACAAAAGATGCTTAAC TGATATACAAAAAGCACTAATTGGTGCCTCTATATGCTTTTT AAAACCCAAAGACCAGGAAAGAAAAAGAAGATTCATCACA GAATTCTGCAGATATCCATCACACTGGCGGCCGCTCGAGC (SEQ ID NO: 31) | Taq DNA polymerase endpoint PCR |
| pCR.FWD | CTAGTAACGGCCGCCAGTGTGCTGGAATTC (SEQ ID NO: 32) | |
| pCR.REV | CCGCCAGTGTGATGGATATCTGCAGAATTC (SEQ ID NO: 33) | |

TABLE 2

Cellular reagent Gibson assembly with or without heat treatment of cellular reagents.

| Gibson assembly type | Number of colonies |
|---|---|
| Gel purified pCR2.1 linearized vector + *Aedes albopictus* S7 gBlock | |
| Cellular reagent Gibson with heat-treated Taq DNA polymerase and Taq DNA Ligase | 111[a] |
| Cellular reagent Gibson with no heat treatment of cellular reagents | 12 |
| Gibson with pure enzymes (positive control) | 183 |
| Assembly with no enzymes (negative control) | 1 |
| Gel purified pCR2.1 linearized vector + *E. coli* yaiO gBlock | |
| Cellular reagent Gibson with heat-treated Taq DNA polymerase and Taq DNA Ligase | 173 |
| Gibson with pure enzymes (positive control) | 360 |
| Assembly with no enzymes (negative control) | 1 |

[a]All tested positive control clones had the correct sequence. 50% of the cellular reagent Gibson assembled plasmids had the correct sequence. Remaining recovered colonies contained re-circularized vector.

REFERENCES

1. Rittie L and Perbal B (2008) Enzymes used in molecular biology: a useful guide. J Cell Commun Signal 2: 25-45.
2. Treacy D J, Sankaran S M, Gordon-Messer S, Saly D, Miller R, et al. (2011) Implementation of a Project-Based Molecular Biology Laboratory Emphasizing Protein Structure-Function Relationships in a Large Introductory Biology Laboratory Course. Cbe-Life Sciences Education 10: 18-24.
3. Garibyan L and Avashia N (2013) Polymerase chain reaction. J Invest Dermatol 133: 1-4.
4. Zhao Y X, Chen F, Li Q, Wang L H and Fan C H (2015) Isothermal Amplification of Nucleic Acids. Chem Rev 115: 12491-12545.
5. Casini A, Storch M, Baldwin G S and Ellis T (2015) Bricks and blueprints: methods and standards for DNA assembly. Nature Reviews Molecular Cell Biology 16: 568-576.
6. Buchan B W and Ledeboer N A (2014) Emerging technologies for the clinical microbiology laboratory. Clin Microbiol Rev 27: 783-822.
7. Smanski M J, Zhou H, Claesen J, Shen B, Fischbach M A, et al. (2016) Synthetic biology to access and expand nature's chemical diversity. Nat Rev Microbiol 14: 135-149.
8. Ersson B, Ryden L and Janson J-C (2011) Protein Purification: Principles, High Resolution Methods, and Applications. New Jersey: John Wiley & Sons, Inc.
9. Scopes R K (1994) Protein Purification: Principles and Practice. New York: Springer-Verlag New York.
10. Ward W (2012) The Art of Protein Purification, Protein Purification. InTech.
11. Burden D W and Whitney D B (1995) Protein Purification by Column Chromatography. BiotechnologyProteins to PCR: A Course in Strategies and Lab Techniques. Boston, Mass.: Birkhauser Boston. pp. 93-124.
12. Arnau J, Lauritzen C, Petersen F E and Pedersen J (2006) Current strategies for the use of affinity tags and tag removal for the purification of recombinant proteins. Protein Expr Purif 48: 1-13.
13. Goh H C, Sobota R M, Ghadessy F J and Nirantar S (2017) Going native: Complete removal of protein purification affinity tags by simple modification of existing tags and proteases. Protein Expr Purif 129: 18-24.
14. Guan D L and Chen Z L (2014) Challenges and recent advances in affinity purification of tag-free proteins. Biotechnol Lett 36: 1391-1406.
15. Zhang H L, Omondi M W, Musyoka A M, Afwamba I A, Swai R P, et al. (2016) Challenges of Maintaining Good Clinical Laboratory Practices in Low-Resource Settings: A Health Program Evaluation Framework Case Study From East Africa. Am J Clin Pathol 146: 199-206.
16. Lianidou E, Ahmad-Nejad P, Ferreira-Gonzalez A, Izuhara K, Cremonesi L, et al. (2014) Advancing the education in molecular diagnostics: The IFCC-Initiative "Clinical Molecular Biology Curriculum" (C-CMBC); A ten-year experience. Clin Chim Acta 436: 5-8.
17. Barnes W M (1994) PCR amplification of up to 35-kb DNA with high fidelity and high yield from lambda bacteriophage templates. Proceedings of the National Academy of Sciences of the United States of America 91: 2216-2220.
18. Chien A, Edgar D B and Trela J M (1976) Deoxyribonucleic acid polymerase from the extreme thermophile *Thermus aquaticus*. J Bacteriol 127: 1550-1557.
19. Phang S M, Teo C Y, Lo E and Wong V W (1995) Cloning and complete sequence of the DNA polymerase-encoding gene (Bstpoll) and characterisation of the Klenow-like fragment from *Bacillus stearothermophilus*. Gene 163: 65-68.
20. Wang Y, Prosen D E, Mei L, Sullivan J C, Finney M, et al. (2004) A novel strategy to engineer DNA polymerases for enhanced processivity and improved performance in vitro. Nucleic Acids Res 32: 1197-1207.
21. Uemori T, Ishino Y, Toh H, Asada K and Kato I (1993) Organization and Nucleotide-Sequence of the DNA-Polymerase Gene from the Archaeon *Pyrococcus-furiosus*. Nucleic Acids Res 21: 259-265.
22. Ellefson J W, Gollihar J, Shroff R, Shivram H, Iyer V R, et al. (2016) Synthetic evolutionary origin of a proofreading reverse transcriptase. Science 352: 1590-1593.
23. Jiang Y S, Bhadra S, Li B, Wu Y R, Milligan J N, et al. (2015) Robust strand exchange reactions for the sequence-specific, real-time detection of nucleic acid amplicons. Anal Chem 87: 3314-3320.
24. Gibson D G, Young L, Chuang R Y, Venter J C, Hutchison C A, et al. (2009) Enzymatic assembly of DNA molecules up to several hundred kilobases. Nat Methods 6: 343-345.
25. Milligan J N, Shroff R, Garry D J and Ellington A D (2018) Evolution of a Thermophilic Strand-Displacing Polymerase Using High-Temperature Isothermal Compartmentalized Self-Replication. Biochemistry.
26. Lawyer F C, Stoffel S, Saiki R K, Myambo K, Drummond R, et al. (1989) Isolation, Characterization, and Expression in *Escherichia-coli* of the DNA-Polymerase Gene from *Thermus-aquaticus*. J Biol Chem 264: 6427-6437.
27. Waggoner J J and Pinsky B A (2016) Zika Virus: Diagnostics for an Emerging Pandemic Threat. Journal of clinical microbiology 54: 860-867.
28. Green R and Rogers E J (2013) Transformation of chemically competent *E. coli*. Methods Enzymol 529: 329-336.
29. Seetharam C, Soundarajan S, Udas A C, Rao A S and Apte S K (2009) Lyophilized, non-viable, recombinant *E. coli* cells for cadmium bioprecipitation and recovery. Process Biochem 44: 246-250.
30. Wessman P, Hakansson S, Leifer K and Rubino S (2013) Formulations for Freeze-drying of Bacteria and Their Influence on Cell Survival. Jove-Journal of Visualized Experiments.
31. Mackey B M, Miles C A, Parsons S E and Seymour D A (1991) Thermal-Denaturation of Whole Cells and Cell Components of *Escherichia-coli* Examined by Differential Scanning calorimetry. J Gen Microbiol 137: 2361-2374.
32. Patchett M L, Neal T L, Schofield L R, Strange R C, Daniel R M, et al. (1989) Heat-Treatment Purification of Thermostable Cellulase and Hemicellulase Enzymes Expressed in *Escherichia-coli*. Enzyme Microb Technol 11: 113-115.
33. Harve K S, Lareu R, Rajagopalan R and Raghunath M (2010) Understanding how the crowded interior of cells stabilizes DNA/DNA and DNA/RNA hybrids-in silico predictions and in vitro evidence. Nucleic Acids Res 38: 172-181.
34. Markarian M Z and Schlenoff J B (2010) Effect of molecular crowding and ionic strength on the isothermal hybridization of oligonucleotides. J Phys Chem B 114: 10620-10627.
35. Tomita N, Mori Y, Kanda H and Notomi T (2008) Loop-mediated isothermal amplification (LAMP) of gene sequences and simple visual detection of products. Nature Protocols 3: 877-882.
36. Schofield D A, Sharp N J and Westwater C (2012) Phage-based platforms for the clinical detection of human bacterial pathogens. Bacteriophage 2: 105-283.
37. Parra M, Jung J, Boone T D, Tran L, Blaber E A, et al. (2017) Microgravity validation of a novel system for RNA isolation and multiplex quantitative real time PCR analysis of gene expression on the International Space Station. PLoS One 12: e0183480.
38. Liu A P and Fletcher D A (2009) Biology under construction: in vitro reconstitution of cellular function. Nature Reviews Molecular Cell Biology 10: 644-650.
39. Hodgman C E and Jewett M C (2012) Cell-free synthetic biology Thinking outside the cell. Metab Eng 14: 261-269.
40. Hunt J P, Yang S O, Wilding K M and Bundy B C (2017) The growing impact of lyophilized cell-free protein expression systems. Bioengineered 8: 325-330.
41. Pardee K, Green A A, Takahashi M K, Braff D, Lambert G, et al. (2016) Rapid, Low-Cost Detection of Zika Virus Using Programmable Biomolecular Components. Cell 165: 1255-1266.
42. Jewett M C, Calhoun K A, Voloshin A, Wuu J J and Swartz J R (2008) An integrated cell-free metabolic platform for protein production and synthetic biology. Mol Syst Biol 4.
43. Gan R and Jewett M C (2014) A combined cell-free transcription-translation system from *Saccharomyces cerevisiae* for rapid and robust protein synthe. Biotechnology journal 9: 641-651.
44. Chong S (2014) Overview of cell-free protein synthesis: historic landmarks, commercial systems, and expanding applications. Current protocols in molecular biology/edited by Frederick M Ausubel [et al] 108: 16 30 11-11.
45. Ogonah O W, Polizzi K M and Bracewell D G (2017) Cell free protein synthesis: a viable option for stratified medicines manufacturing? Current Opinion in Chemical Engineering 18: 77-83.
46. Kwon Y C and Jewett M C (2015) High-throughput preparation methods of crude extract for robust cell-free protein synthesis. Sci Rep 5: 8663.
47. Smith M T, Berkheimer S D, Werner C J and Bundy B C (2014) Lyophilized *Escherichia coli*-based cell-free systems for robust, high-density, long-term storage. BioTechniques 56: 186-193.
48. Si T and Zhao H (2016) A brief overview of synthetic biology research programs and roadmap studies in the United States. Synth Syst Biotechnol 1: 258-264.
49. Kelwick R, Bowater L, Yeoman K H and Bowater R P (2015) Promoting microbiology education through the iGEM synthetic biology competition. FEMS Microbiol Lett 362.
50. Mattanovich D, Branduardi P, Dato L, Gasser B, Sauer M, et al. (2012) Recombinant protein production in yeasts. Methods Mol Biol 824: 329-358.

What is claimed is:

1. A method of utilizing an enzyme in a nucleic acid manipulation process, the method comprising:
   a. transforming a microorganism with a non-native enzyme;
   b. inducing expression of the enzyme in the microorganism, thereby producing the non-native enzyme;
   c. dehydrating or freeze-drying the microorganism without using an excipient;
   d. rehydrating the microorganism of step c);
   e. adding the microorganism of step d) directly to a non-naturally occurring nucleic acid manipulation process, thereby obtaining a non-purified cellular reagent, including the non-native enzyme, wherein the non-native enzyme is not purified from the microorganism prior to addition to the nucleic acid manipulation process;
   f. carrying out the nucleic acid manipulation process using the enzyme.

2. The method of claim 1, wherein the enzyme is necessary for the nucleic acid manipulation process.

3. The method of claim 1, wherein the enzyme comprises polymerase, reverse transcriptase, methylase, nuclease, cleavase, phosphatase, kinase, nickase, pyrophosphatase, DNA glycosylase, recombinase, helicase, topoisomerase, methyltransferase, capping enzyme, deadenylase, or ligase.

4. The method of claim 1, wherein the process is nucleic acid amplification.

5. The method of claim 4, wherein the nucleic acid amplification is thermostable amplification.

6. The method of claim 4, wherein the nucleic acid amplification is isothermal amplification.

7. The method of claim 1, wherein more than one enzyme is transformed into the microorganism.

8. The method of claim 1, wherein multiple enzymes are transformed into multiple microorganisms, and multiple microorganisms are added to the non-naturally occurring molecular process.

9. The method of claim 1, wherein the nucleic acid manipulation process comprises further components needed to carry out the nucleic acid manipulation process.

10. The method of claim 9, wherein the further components are provided exogenously during the nucleic acid manipulation process.

11. The method of claim 9, wherein the further components are naturally occurring products produced by the microorganism.

12. The method of claim 1, wherein the microorganism is prokaryotic.

\* \* \* \* \*